(12) United States Patent
Dorrestein et al.

(10) Patent No.: US 11,980,645 B2
(45) Date of Patent: May 14, 2024

(54) BILE ACIDS AND USE IN DISEASE TREATMENT

(71) Applicant: The Regents of the University of California, Oakland, CA (US)

(72) Inventors: Pieter Dorrestein, La Jolla, CA (US); Alexey Melnik, La Jolla, CA (US); Alexander Aksenov, La Jolla, CA (US); Robert Quinn, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 309 days.

(21) Appl. No.: 17/422,868

(22) PCT Filed: Jan. 22, 2020

(86) PCT No.: PCT/US2020/014603
§ 371 (c)(1),
(2) Date: Jul. 14, 2021

(87) PCT Pub. No.: WO2020/154397
PCT Pub. Date: Jul. 30, 2020

(65) Prior Publication Data
US 2022/0202881 A1    Jun. 30, 2022

Related U.S. Application Data

(60) Provisional application No. 62/795,244, filed on Jan. 22, 2019.

(51) Int. Cl.
| | | |
|---|---|---|
| *A61K 35/742* | (2015.01) | |
| *A61K 31/575* | (2006.01) | |
| *A61P 1/14* | (2006.01) | |

(52) U.S. Cl.
CPC .......... *A61K 35/742* (2013.01); *A61K 31/575* (2013.01); *A61P 1/14* (2018.01)

(58) Field of Classification Search
None
See application file for complete search history.

(56) References Cited

U.S. PATENT DOCUMENTS

| | | |
|---|---|---|
| 2016/0030494 A1 | 2/2016 | Henn et al. |
| 2018/0296516 A1 | 10/2018 | Hamill et al. |
| 2020/0164005 A1* | 5/2020 | Wu .............. A61K 35/742 |

FOREIGN PATENT DOCUMENTS

WO    2018/195097 A1    10/2018

OTHER PUBLICATIONS

PCT International Search Report and Written Opinion for PCT Application No. PCT/US2020/014603 dated Apr. 2, 2020 (8 pages).
Tripathi et al., "Enhancement of Solubility and Dissolution of Indomethacin and Phylbutazone by Cholic and Deoxycholic Acid Conjugates," Drug Development and Industrial Pharmacy, 1992, vol. 18, abstract.

* cited by examiner

*Primary Examiner* — Michelle F. Paguio Frising
(74) *Attorney, Agent, or Firm* — Eversheds Sutherland (US) LLP

(57) ABSTRACT

Compositions and methods of use for modulating bile acids, including phenylalanocholic acid, tyrosocholic acid and leucocholic acid, to treat diseases, such as inflammatory bowel disease. In embodiments, the invention provides pharmaceutical compositions that modulate levels of a bile acid conjugate in a subject. In embodiments, the invention provides pharmaceutical compositions that modulate levels of a bile acid conjugate in a particular organ or bodily region of the subject.

14 Claims, 49 Drawing Sheets

1. Glycocholic Acid

Chemical Formula: $C_{26}H_{43}NO_6$
Exact Mass: 465.3090

2. Phenylalanocholic Acid

Chemical Formula: $C_{33}H_{49}NO_6$
Exact Mass: 555.3560

3. Tyrosocholic Acid

Chemical Formula: $C_{33}H_{49}NO_7$
Exact Mass: 571.3509

4. Leucocholic Acid

Chemical Formula: $C_{30}H_{51}NO_6$
Exact Mass: 521.3716

3. Soyasaponin III m/z796.469

1b. Dehydrosoyasaponin I m/z941.493

1. Soyasaponin I m/z943.526

1a. Deoxysoyasaponin I m/z925.493

BILE ACIDS AND USE IN DISEASE TREATMENT

CROSS REFERENCE TO RELATED APPLICATIONS

This application claims the priority benefit of PCT/US2020/014603 filed on Jan. 22, 2020 which claims the priority benefit to U.S. Provisional Patent Application No. 62/795,244, filed Jan. 22, 2019, the entire contents of which are incorporated herein by reference.

TECHNICAL FIELD

The present invention relates to bile acids and the use thereof in research and in treating diseases.

BACKGROUND

A mosaic of cross-phylum chemical interactions occurs between all metazoans and their microbiomes. A number of molecular families known to be produced by the microbiome have a profound impact on the balance between health and disease[1-9]. Considering the diversity of the human microbiome, numbering over 40,000 operational taxonomic units[10], the impact of the microbiome on the chemistry of an entire animal remains underexplored.

SUMMARY OF THE INVENTION

In this invention, mass spectrometry informatics and data visualization approaches[11-13] were used to provide an assessment of the impacts of the microbiome on the chemistry of an entire mammal by comparing metabolomics data from germ-free (GF) and specific pathogen free (SPF) mice. The invention shows that the microbiota affected the chemistry of all organs. This included amino acid conjugations of host bile acids that have evaded characterization despite the extensive research on bile acid chemistry[14]. These bile acid conjugates are also found in humans, where they are enriched in states of disease. These compounds agonized the farnesoid X receptor (FXR) in vitro and a gavage of mice resulted in reduced expression of bile acid synthesis genes in vivo.

In embodiments, the invention provides methods of treating a subject in need comprising administering to the subject a treatment effective amount of a pharmaceutical composition that modulates levels of a bile acid conjugate.

In embodiments, the invention provides methods of regulating bile acid levels in a subject in need comprising administering to the subject an effective amount of a pharmaceutical composition that modulates levels of a bile acid conjugate.

In embodiments, the invention provides methods of regulating acylcarnitine levels in a subject in need comprising administering to the subject an effective amount of a pharmaceutical composition that modulates levels of a bile acid conjugate.

In embodiments, the modulation of levels of bile acid conjugates in a subject can be an increase or a decrease in bile acid conjugates in the subject, depending upon the disease and condition of the subject.

In embodiments, the invention provides pharmaceutical compositions that modulate levels of a bile acid conjugate in a subject. In embodiments, the invention provides pharmaceutical compositions that modulate levels of a bile acid conjugate in a particular organ or bodily region of the subject.

In embodiments, the bile acid conjugate is selected from phenylalanocholic acid, tyrosocholic acid, leucocholic acid and combinations thereof. In embodiments, the bile acid conjugate is acyl conjugated with amino acids other than glycine or taurine.

In embodiments, the pharmaceutical composition comprises microbes that increase levels of the bile acid conjugate in vivo. In embodiments, the invention provides that the microbes are Clostridia.

In embodiments, the invention provides that the subject has inflammatory bowel disease (IBD), Chrone's disease (CD), ulcerative colitis (UC), cystic fibrosis (CF), liver cancer, colorectal cancer, diabetes, non-alcoholic fatty liver disease or atherosclerosis.

In embodiments, the invention provides that the pharmaceutical composition stimulates farnesoid X receptor (FXR) in the subject.

DETAILED DESCRIPTION

Figure 1A:
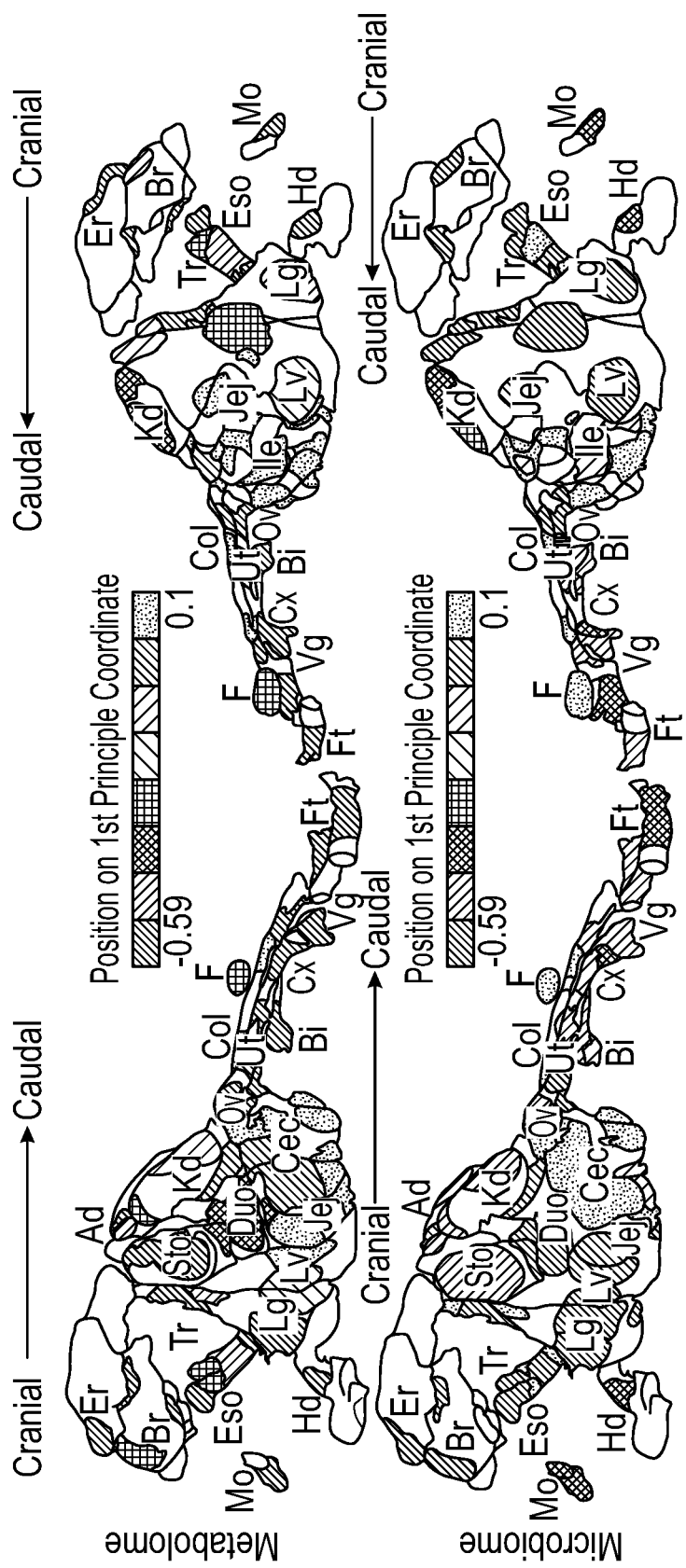
FIGS. 1a-1e show global impacts of the microbiome on the chemistry of an entire mammal.

All publications, patents, and patent applications mentioned in this specification are incorporated herein by reference to the same extent as if each individual publication, patent, or patent application was specifically and individually indicated to be incorporated by reference.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, 2$^{nd}$ ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); Remington, The Science and Practice of Pharmacy, 20$^{th}$ ed., (Lippincott, Williams & Wilkins 2003), and Remington, The Science and Practice of Pharmacy, 22$^{th}$ ed., (Pharmaceutical Press and Philadelphia College of Pharmacy at University of the Sciences 2012).

In embodiments, the invention provides methods of treating a subject in need comprising administering to the subject a treatment effective amount of a pharmaceutical composition that modulates levels of a bile acid conjugate.

In embodiments, the invention provides methods of regulating bile acid levels in a subject in need comprising administering to the subject an effective amount of a pharmaceutical composition that modulates levels of a bile acid conjugate.

In embodiments, the invention provides methods of regulating acylcarnitine levels in a subject in need comprising administering to the subject an effective amount of a pharmaceutical composition that modulates levels of a bile acid conjugate.

In embodiments, the modulation of levels of bile acid conjugates in a subject can be an increase or a decrease in bile acid conjugates in the subject, depending upon the disease and condition of the subject.

In embodiments, the invention provides pharmaceutical compositions that modulate (increase or decrease) levels of a bile acid conjugate in a subject. In embodiments, the invention provides pharmaceutical compositions that modulate levels of a bile acid conjugate in a particular organ or bodily region of the subject.

In embodiments, the bile acid conjugate is an amino acid conjugation of cholic acid. In embodiments, the bile acid conjugate is selected from phenylalanocholic acid, tyrosocholic acid, leucocholic acid and combinations thereof. In embodiments, the bile acid conjugate is acyl conjugated with amino acids other than glycine or taurine.

In embodiments, the pharmaceutical composition comprises microbes that increase levels of the bile acid conjugate in vivo. In embodiments, the invention provides that the microbes are *Clostridia*.

In embodiments, the invention provides that the pharmaceutical composition stimulates farnesoid X receptor (FXR) in the subject.

In embodiments, the invention provides that the subject has inflammatory bowel disease (IBD), Chrone's disease (CD), ulcerative colitis (UC), cystic fibrosis (CF), liver cancer, colorectal cancer, diabetes, non-alcoholic fatty liver disease or atherosclerosis. In embodiments, the invention provides methods for increasing levels of a bile acid conjugate when the subject has inflammatory bowel disease (IBD), Chrone's disease (CD), ulcerative colitis (UC), cystic fibrosis (CF), liver cancer, colorectal cancer, diabetes, or non-alcoholic fatty liver disease. In embodiments, the invention provides methods for decreasing levels of a bile acid conjugate when the subject has atherosclerosis. It will be understood that modulation of bile acid conjugate levels can be modulated to increase or decrease in the subject based on the particular disease or condition.

In embodiments, the invention provides methods of manufacturing bile acid conjugates by the routes of synthesis described herein. In embodiments, the bile acid conjugates synthesized are selected from phenylalanocholic acid, tyrosocholic acid, leucocholic acid.

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

It is understood that aspects and embodiments of the invention described herein include "consisting" and/or "consisting essentially of" aspects and embodiments.

It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Values or ranges may be also be expressed herein as "about," from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value, or within 2% of the recited value.

As used herein, "patient" or "subject" means a human or animal subject to be treated or observed.

As used herein the term "pharmaceutical composition" refers to a pharmaceutical acceptable composition, wherein the composition comprises a pharmaceutically active agent, and in some embodiments further comprises a pharmaceutically acceptable carrier. In some embodiments, the pharmaceutical composition may be a combination of pharmaceutically active agents and carriers.

The term "combination" refers to either a fixed combination in one dosage unit form, or a kit of parts for the combined administration where one or more active compounds and a combination partner (e.g., another drug as explained below, also referred to as "therapeutic agent" or "co-agent") may be administered independently at the same time or separately within time intervals. In some circumstances, the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

As used herein the term "pharmaceutically acceptable" means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

As used herein the term "pharmaceutically acceptable carrier" refers to an excipient, diluent, preservative, solubilizer, emulsifier, adjuvant, and/or vehicle with which demethylation compound(s), is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20th ed., (Lippincott, Williams & Wilkins 2003). Except insofar as any conventional media or agent is incompatible with the active compound, such use in the compositions is contemplated.

As used herein, "therapeutically effective" refers to an amount of a pharmaceutically active compound(s) that is sufficient to treat or ameliorate, or in some manner reduce the symptoms associated with diseases and medical conditions. When used with reference to a method, the method is sufficiently effective to treat or ameliorate, or in some manner reduce the symptoms associated with diseases or conditions. For example, an effective amount in reference to age-related eye diseases is that amount which is sufficient to block or prevent onset; or if disease pathology has begun, to palliate, ameliorate, stabilize, reverse or slow progression of the disease, or otherwise reduce pathological consequences of the disease. In any case, an effective amount may be given in single or divided doses.

As used herein, the terms "treat," "treatment," or "treating" embraces at least an amelioration of the symptoms associated with diseases in the patient, where amelioration is used in a broad sense to refer to at least a reduction in the magnitude of a parameter, e.g. a symptom associated with the disease or condition being treated. As such, "treatment" also includes situations where the disease, disorder, or pathological condition, or at least symptoms associated therewith, are completely inhibited (e.g. prevented from happening) or stopped (e.g. terminated) such that the patient no longer suffers from the condition, or at least the symptoms that characterize the condition.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound or dosage form provided herein, with or without one or more other additional active agent(s), prior to the onset of symptoms, particularly to subjects at risk of disease or disorders provided herein. The terms encompass the inhibition or reduction of a symptom of the particular disease. In certain embodiments, subjects with familial history of a disease are potential candidates for preventive regimens. In certain embodiments, subjects who have a history of recurring symptoms are also potential candidates for prevention. In this regard, the term "prevention" may be interchangeably used with the term "prophylactic treatment."

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, a compound described herein is intended to encompass all possible stereoisomers, unless a particular stereochemistry is specified. Where structural isomers of a compound are interconvertible via a low energy barrier, the compound may exist as a single tautomer or a mixture of tautomers. This can take the form of proton tautomerism; or so-called valence tautomerism in the compound, e.g., that contain an aromatic moiety.

The term "pharmaceutically active" as used herein refers to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug.

The term "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

The term "pharmaceutically acceptable salt" as used herein refers to acid addition salts or base addition salts of the compounds, such as the multi-drug conjugates, in the present disclosure. A pharmaceutically acceptable salt is any salt which retains the activity of the parent agent or compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zurich, 2002; Berge et al., J Pharm. Sci. 66: 1, 1977). In some embodiments, a "pharmaceutically acceptable salt" is intended to mean a salt of a free acid or base of an agent or compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. An agent or compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

The term "pharmaceutically acceptable carrier" as used herein refers to an excipient, diluent, preservative, solubilizer, emulsifier, adjuvant, and/or vehicle with which an agent or compound, such as a multi-drug conjugate, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy. 20$^{m}$ ed., (Lippincott, Williams & Wilkins 2003). Except insofar as any conventional media or agent is incompatible with the active compound, such use in the compositions is contemplated.

EXAMPLES

Figure 1B:
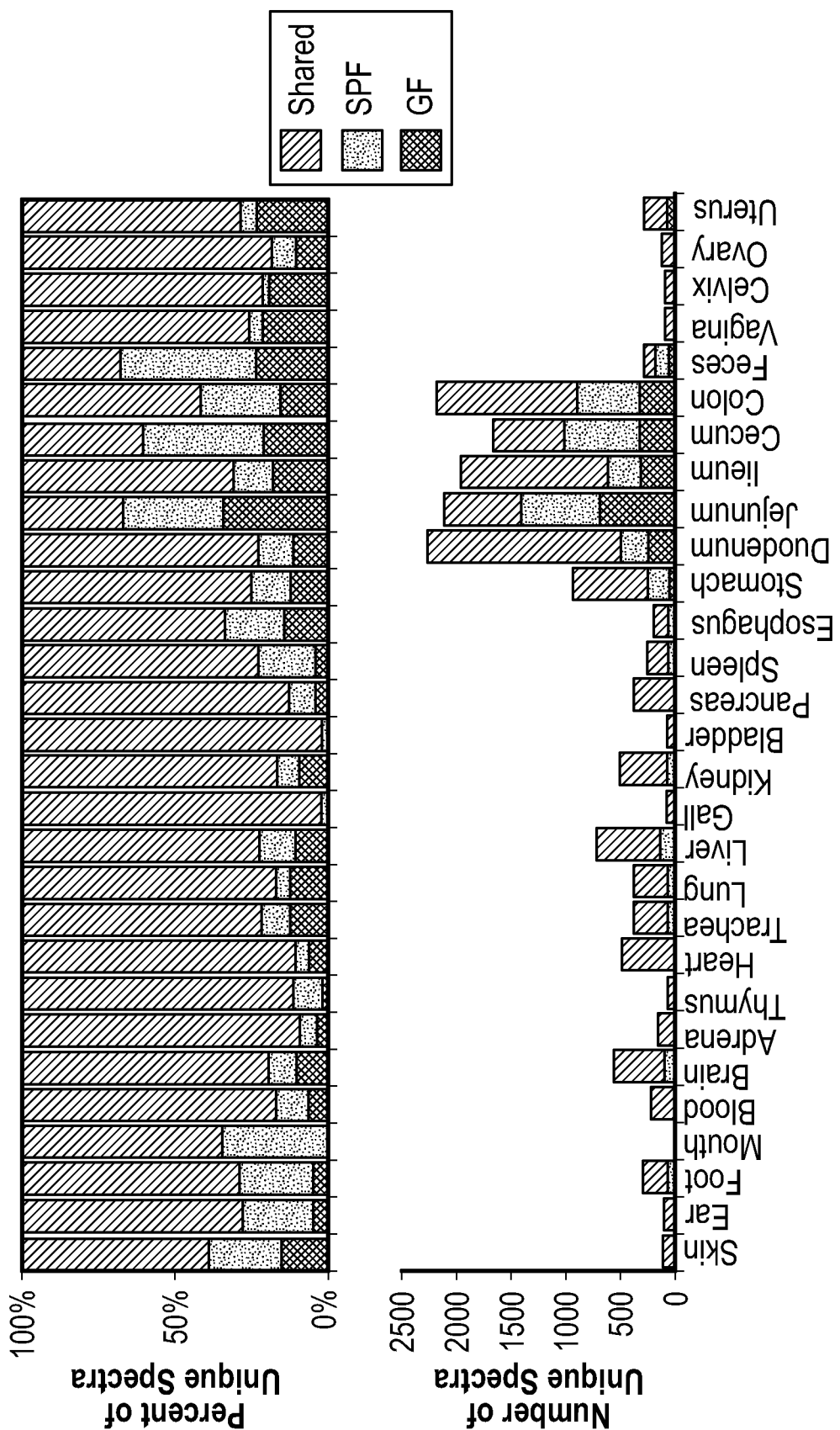
Figures 3A, 3B, 3C, 3D, 3E:
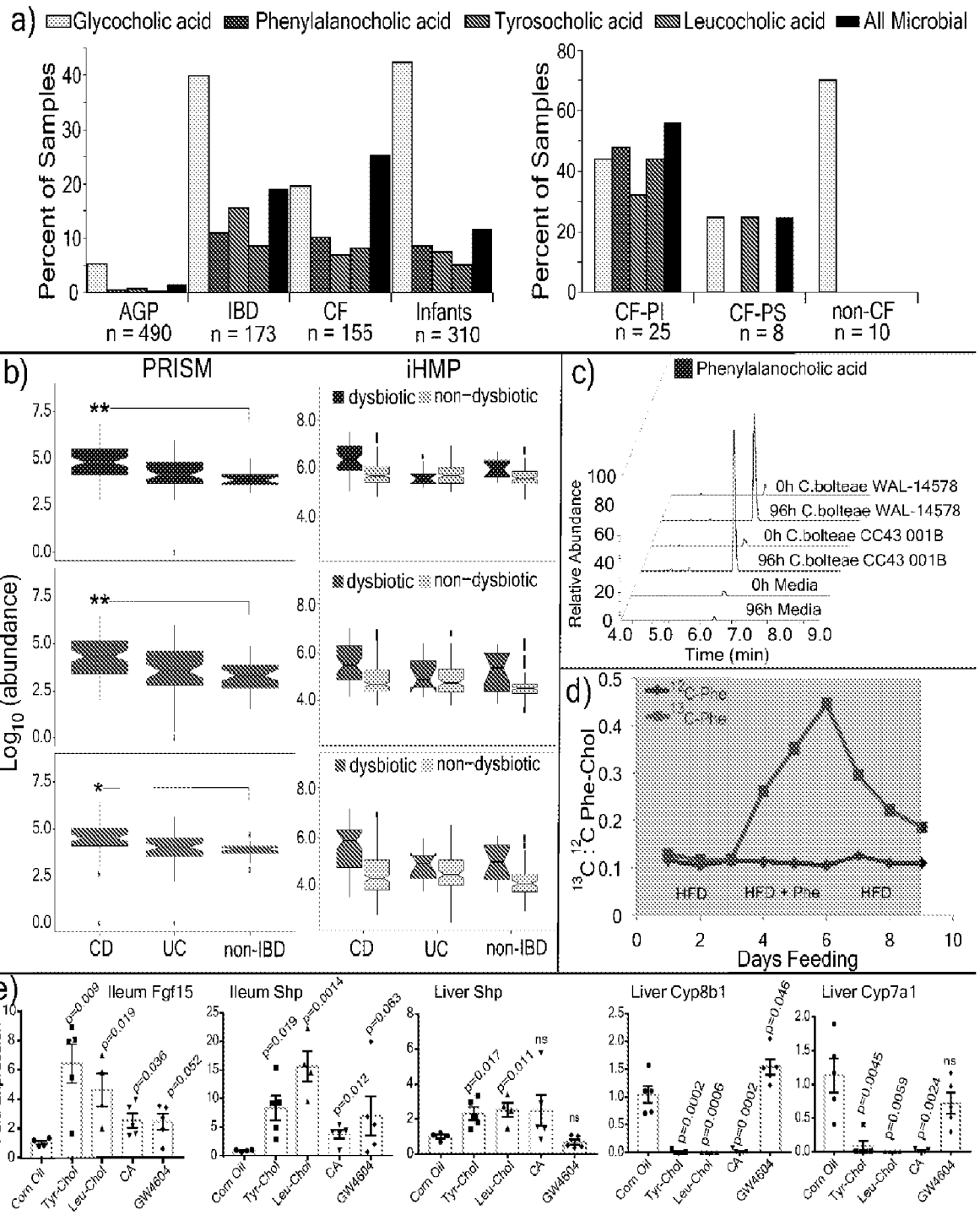
FIGS. 3a-3e show the presence, synthesis and function of microbial bile acid conjugates.

In total, 768 samples from 96 sample sites of 29 different organs were analyzed from four GF and four colonized mice by LC-MS/MS mass spectrometry and 16S rRNA gene sequencing. Mapping the $1^{st}$ principal coordinate position of each sample from SPF mice onto a 3D mouse model[13] enabled visualization of the similarity of the microbiome and metabolome through all organs and organ systems (FIGS. 1a-1b, 3d). Different sections through the GI tract had unique microbiome and metabolome profiles. There was a distinct difference between the similarity of the two data types in murine fecal samples. The metabolome differed between fecal samples and the distal gastrointestinal (GI) tract, whereas the microbiome was more similar between feces and colon/cecum samples.

To characterize the chemical impact of the microbiome, the mass spectrometry data was subjected to molecular networking[12]. The algorithm identified 7,913 spectra of which 14.7+/−2.2% were observed in colonized mice and 10.0+/−0.7% were exclusive to GF (FIG. 1b, FIG. 4). Although the overall profiles showed the strongest differences between GF and SPF were in the GI tract, molecular networking identified unique chemical signatures from the microbiome in all organs, ranging from 2% in the bladder to 44% in stool (FIG. 1b). The metabolome of the cecum, the main site of microbial fermentation of food, was most profoundly affected by the microbiota. Spectral library searching enabled annotation of 8.9% of nodes in the molecular network[11,15] (level two or three according to[16]). Many of the changes attributed to the microbiome were location specific, resulting from the metabolism of plant natural products from food and bile acids (FIG. 1c, FIGS. 5, 6, 7). The Shannon diversity of the GF and SPF mouse metabolome was mirrored in the upper GI tract, both being low in the esophagus and higher in the stomach and duodenum. Upon transition to the cecum, however, the diversity of the two groups of mice began to separate (FIG. 1d). The molecular diversity in the cecum and colon of colonized mice was higher than that of GF mice, but not in the stool samples (FIG. 1d). In the duodenum, the location where the gallbladder adds bile to the intestine, there was a contrast in microbiome and metabolome diversity, where a high metabolome diversity corresponded to a low microbial diversity.

Molecular networking enabled meta-mass shift chemical profiling[17] of the GF and SPF GI tracts, which is an analysis of chemical transformations based on parent mass shifts between related spectra without the requirement of knowing the molecular structures. In colonized animals, there was a signature for water loss in the duodenum and jejunum and the loss of $H_2$, acetyl and methyl groups in latter parts of the GI tract (FIG. 1e). Of all the $H_2$ shifts, 23.1% were associated with bile acids, indicating that colonization resulted in oxidation of bile acids, a known microbial transformation[18]. Deacetylations were also prevalent in colonized animals, though the metabolites upon which this was occurring remain unidentified. GF mice had mass gains corresponding to saccharides in all regions of the GI tract (FIG. 1e), which were primarily associated with plant natural products (e.g. soyasaponins and flavonoids). The absence of these sugars in SPF mice implicates the microbiome in their metabolism (FIGS. 5, 6). A unique mass gain of $C_4H_8$ was detected in the jejunum and ileum of SPF mice (FIG. 1e) and 18.2% of spectra with this mass gain were derived from an unknown molecule related to the conjugated bile acid glycocholic acid (GCA) (FIG. 2a). Overall, both GF and SPF mice had frequent and diverse mass losses between related molecules, but there were fewer molecules in colonized mice that gained a molecular group (FIG. 1e). This indicates that the microbiome contributed more to the catabolic breakdown of molecules and less to anabolism. However, the addition of $C_4H_8$ to GCA is a particularly interesting anabolic reaction that was dependent on the gut microbiome.

Discovery of new conjugated bile acids: Glycine and taurine conjugated bile acids were detected in both GF and SPF mice. The glycine and taurine amino acids were removed as they passed through the GI tract in SPF mice only, which is a known microbial transformation[19] (FIG. 1b, FIG. 7). The conjugated bile acid molecular network had several modified forms of these compounds that were only present in colonized animals, including the $C_4H_8$ addition described above that was related to the MS/MS of GCA (FIG. 2a). Analysis of the MS/MS spectra of three of these SPF nodes (m/z 556.363, 572.358 and 522.379) showed maintenance of the core cholic acid, but with a fragmentation pattern characteristic of the presence of the amino acids phenylalanine, tyrosine and leucine through an amide bond at the conjugation site in place of glycine or taurine (FIG. 8, Table 1).

TABLE 1

Mass spectrometry details and ions of interest for identification of novel conjugated bile acids.

| Compound | Exact Mass | Observed Mass | Charge | Immonium Ion | Amino acid fragment | Other diagnostic fragments |
|---|---|---|---|---|---|---|
| Phenylalanocholic acid | 555.3559 | 556.362 | H+ | 120.0816 | 166.0862 | 337.2525, 319.2420, 227.1398 |
| Tyrosocholic acid | 571.3509 | 572.356 | H+ | 136.0758 | 182.081 | 337.2525, 319.2420, 227.1398 |
| Leucocholic acid | 521.3716 | 522.379 | H+ | 86.0977 | 132.1002 | 337.2525, 319.2420, 227.1398 |

This represents a set of unique amino acid amide conjugations to cholic acid that are mediated by the microbiome creating the novel bile acids phenylalanocholic acid (Phe-chol), tyrosocholic acid (Tyr-chol) and leucocholic acid (Leu-chol). These structures were validated with synthesized standards by retention time and MS/MS matching on several instrument platforms including targeted MS (level one matches[16], FIG. 8,6, Table 1, S5). These molecules were detected in the duodenum, jejunum and ileum of SPF mice only, with 10-fold lower levels found in the cecum and colon after targeted mass spectrometry analysis using isotopically labeled internal standards (Table 2).

TABLE 2 a) Quantification of novel conjugated bile acids in mouse SPF gut samples (n = 4) and standard deviation of the mean across the different organ samples. b) Number of samples that had values above LOD included in the calculations for Table 2a. c) Limit of detection of novel conjugated bile acids with different background matrices.

a)

| | Mean nmol/g tissue | | Standard Deviation | |
|---|---|---|---|---|
| Organ | Tyr | Phe | Tyr | Phe |
| Jejunum | 114.09 | 147 | 79.01 | 99.91 |
| Ileum | 56.03 | 83.56 | 57.85 | 81.33 |
| Cecum | <LOD | 4.74 | 0 | 3.38 |
| Colon | <LOD | 11.61 | 0 | 12.21 | b)

| | Tyr | Leu | Phe |
|---|---|---|---|
| Cecum (n = 24) | 0 | 0 | 11 |
| Colon (n = 24) | 0 | 0 | 9 |
| Ileum (n = 24) | 18 | 16 | 18 |
| Jejunum (n = 24) | 18 | 18 | 18 | c)

| | Limit of Detection (ppb) | | |
|---|---|---|---|
| Organ | Tyr | Ile | Phe |
| Jejunum | 2.70 | 3.12 | 1.74 |
| Ileum | 2.73 | 1.89 | 3.01 |
| Cecum | 3.30 | 2.45 | 1.78 |
| Colon | 7.25 | 5.00 | 1.19 |

Figure 2A:
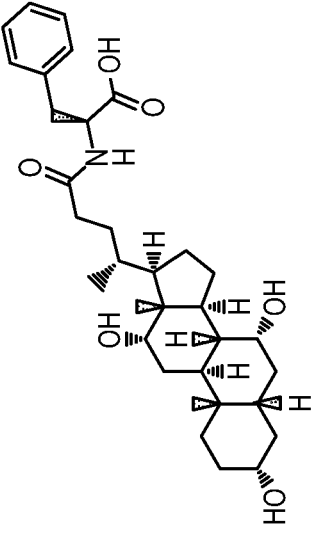
FIGS. 2a-2b show novel microbial bile acid conjugates.
Figure 2A:
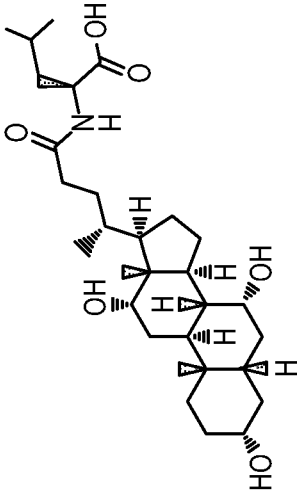
Figure 2A:
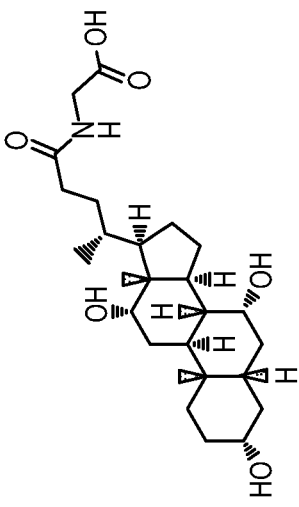
Figure 2A:
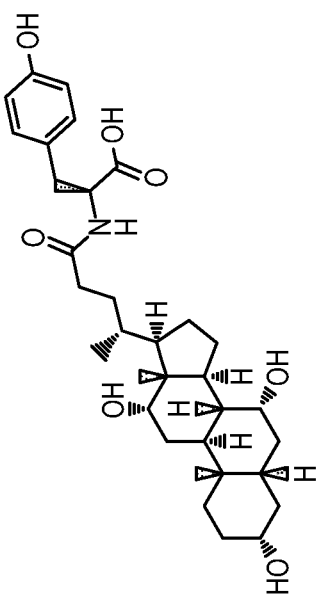
Figure 2A:
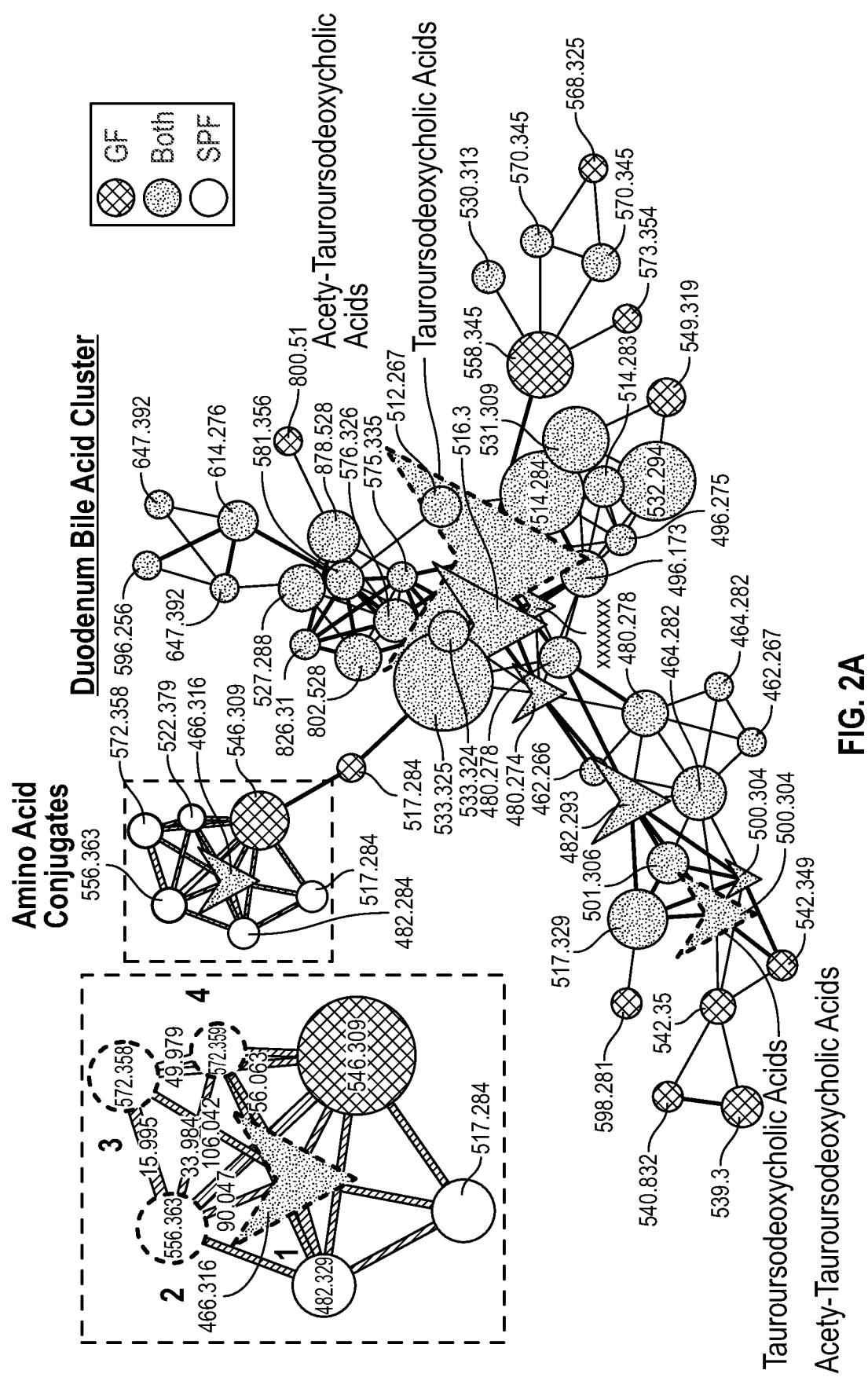
Figure 2B:
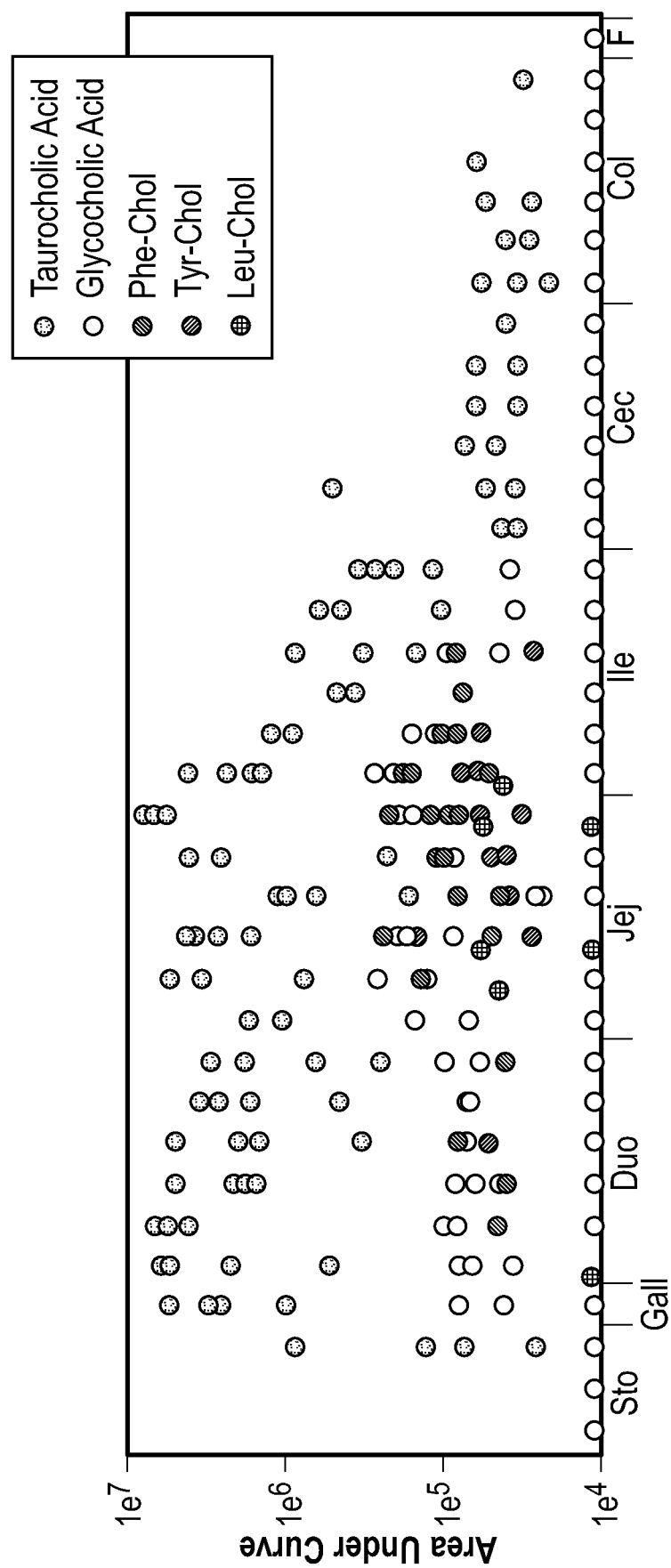

The liver-synthesized glycine and taurine conjugates were found in these same gut locations, but also observed in the gall bladder and liver (FIG. 2*b*, FIG. 9). Phe-chol was the most abundant microbial conjugate on average across the GI tract, present at 147.0 nmol/g tissue (SD+/−99.9) in the jejunum, 83.6 nmol/g tissue (SD+/−81.3) in the ileum, 4.7 nmol/g tissue (SD+/−3.4) in the cecum and 11.6 nmol/g tissue (SD+/-12.2) in the colon; with its highest concentration at 447.2 nmol/g tissue in a single jejunum sample (LOD in Table 2, S6, S7).

The decreased abundance of these unique bile conjugates in the lower GI tract prompted us to investigate if there was reabsorption in the ileum or further metabolism by the microbiota. Portal and peripheral blood was collected from additional SPF (n=4) and GF (n=6) mice and screened for the presence of conjugated bile acids. Taurocholic acid (TCA) and GCA were both present in portal and peripheral blood of colonized and sterile mice, but the new amino acid amide conjugates were not detected (FIG. 9). Furthermore, incubation of these molecules with an actively growing human fecal batch culture showed that the Tyr-, Phe- and Leu-bile acids were not deconjugated by the microbiota, even when deconjugation readily occurred on the host synthesized GCA control, a well-known bile acid amidate hydrolase activity mediated by human microbiota[20] (FIG. 9). However, an oxidation of the cholate core occurred on all three novel conjugates, indicating that they could be modified by microbial enzymes, even when no concurrent oxidation of GCA was observed (FIG. 9).

In the extensive bile acid literature, comprising greater than 42,000 publication records in PubMed[21-27], descriptions of unusual conjugations of bile acids are rare. Through 170 years of bile acid chemistry research, the accepted standard has been that mammalian bile acids are amide conjugated by a host liver enzyme (Bile acid-CoA:amino acid N-acyltransferase, BAAT) with either glycine or taurine. This invention provides amide conjugations with phenylalanine, tyrosine and leucine associated with the microbiome in mice. As also shown in this invention, these compounds are common in humans.

Translation to humans using Mass Spectrometry Search Tool (MASST): A MASST search of 1,004 public data sets available in the Global Natural Products Social Molecular Networking (GNPS) database revealed spectral matches corresponding to Phe-chol, Tyr-chol and Leu-chol in 28 studies comprising samples from the GI tract of both mice (3.2 to 59.4% of all samples) and humans (1.6 to 25.3% of all samples, FIG. 10)[11]. In data from fecal samples collected for the American Gut Project[28], at least one of these unique bile acids was found in 1.6% of human fecal samples, with Tyr-chol being most prevalent (n=490, FIG. 3*a*). They were found in higher frequency from patients with inflammatory bowel disease (IBD), cystic fibrosis (CF) and in infants (FIG. 3*a*).

Re-analysis of GNPS deposited data from a previously published study of the murine microbiome and liver cancer enabled a comparison of the abundance of these molecules in mice fed a high-fat-diet (HFD) and treated with antibiotics[29] (FIG. 10). The Phe, Tyr, and Leu amino acid conjugates were undetectable upon antibiotic exposure, whereas GCA remained, supporting the role of the microbiome in the novel conjugation. In the same study, Phe-chol and Leu-chol were more abundant in mice fed a HFD, with no change observed in the host-conjugated GCA[29] (FIG. 10). The invention further validated this association in data from a separate study where atherosclerosis-prone mice fed HFD also had elevated levels of the microbial conjugates without a corresponding change in the host-produced TCA (FIG. 10). CF is known to result M insufficient production of pancreatic lipase, microbial dysbiosis and the buildup of fat in the gut[30]. In public data from a pediatric CF patient cohort, these compounds were more prevalent in CF patients than healthy controls, particularly those with pancreatic insufficiency (FIG. 3a). Finally, detection of the novel conjugates in IBD patients led to mining metabolome data from the second stage of the human microbiome project (HMP2[31]) that focused on differences between IBD patients and controls, including those with the IBD subtypes Crohn's disease (CD) and ulcerative colitis (UC)[31] (FIG. 3b, Table 6).

*bolteae* strain WAL-1457 could synthesize Phe-chol from the amino acid and cholate precursors (FIG. 11). Similarly, mice were fed HFD with $^{13}$C-phenylalanine and labelled Phe-chol was detected in their feces; demonstrating microbial synthesis in vivo and that the amino acid precursors could come from diet (FIG. 3d). *C. bolteae* is a bile resistant gut bacterium that is more common in autistic children[35], associated with abdominal infections[36], and together with *Blautia producta*, prevented colonization from vancomycin resistant *Enterococcus* in mice[37]. The production of these bile acids by *C. bolteae* further verifies their association with the microbiota of the murine gut and implicates them as potentially important for inter-microbial interactions in the gut microbiome. However, addition of the novel conjugates to batch cultures of human fecal samples did not affect community structure (FIG. 11), leading to the invention's investigation of how these compounds may affect gut physiology through host receptor signaling.

Novel Bile Acids and FXR: The farnesoid X receptor (FXR) is a key receptor for bile acids expressed in the intestine, liver and other tissues. The most potent naturally occurring agonistic ligand of FXR is chenodeoxycholic acid (CDCA), while Tauro-beta-muricholic acid (T-βMCA) is an FXR antagonist[38]. To assess the ability of the novel bile acids from the invention to affect human FXR signaling, a luciferase reporter assay was established in HEK-293

TABLE 6

Mass spectrometry and retention time characteristics of the Phe, Tyr and Leu conjugated bile acids.

| | Compound | Exact Mass | Observed Mass | Retention Time | Charge | Immonium Ion | Amino acid fragment | Other diagnostic fragments |
|---|---|---|---|---|---|---|---|---|
| Pos mode | phenylalanocholic acid | 555.3559 | 556.362 | 5.9 min | H+ | 120.0816 | 166.0862 | 337.2525, 319.2420, 227.1398 |
| | tyrosocholic acid | 571.3509 | 572.356 | 5.3 min | H+ | 136.0758 | 182.081 | 337.2525, 319.2420, 227.1398 |
| | leucocholic acid | 521.3716 | 522.379 | 5.8 min | H+ | 86.0977 | 132.1002 | 337.2525, 319.2420, 227.1398 |
| Neg mode | phenylalanocholic acid | 555.3559 | 554.3491 | 5.9 min | H− | NA | 164.0709 | 302.2722, 221.2677 |
| | tyrosocholic acid | 571.3509 | 570.3499 | 5.3 min | H− | NA | 180.066 | 302.2722, 220.9721 |
| | leucocholic acid | 521.3716 | 520.3646 | 5.8 min | H− | NA | 130.0864 | 302.2722, 221.0867 |

All three metabolites were significantly higher in the dysbiotic state of CD patients but not UC patients (FIG. 3b). Thus, MASST-based mining of GNPS public data showed that these compounds are not only found in healthy humans, but enriched in individuals with fatty guts and IBD, implicating a potential role in, or symptom of, gut dysbiosis and human disease.

Microbes produce the novel bile acids: There was a strong positive correlation between a *Clostridium* sp. and all three bile acids when mice were fed HFD (Pearson's r for Phe-cholate r=0.73, Tyr-cholate, r=0.50 and Leu-cholate, r=0.74, FIG. 10). *Clostridia* are known to oxidize, epimerize, and deconjugate bile acids[32,33]. 20 human gut microbes (with emphasis on *Clostridia*) were cultured in fecal culture media[34] that contained amino acids and cholic acid precursors to screen for production of the novel conjugates. *C. bolteae* strain WAL-14578 and strain CC43001B synthesized both Phe-chol and Tyr-chol (FIG. 11). Addition of labeled $^{13}$C-phenylalanine to the media verified that *C.* embryonic kidney cells[39]. Phe-chol and Tyr-chol were strong human FXR agonists (FIG. 12). The phenylalanine conjugate ($R^2$=0.92, $EC_{50}$=4.5 µM) was twice as strong of an agonist as CDCA ($R^2$=0.88, $EC_{50}$=9.7 µM), while the tyrosine conjugate was the most potent ($R^2$=0.93, $EC_{50}$=0.14 µM). Furthermore, gavage of mice with these compounds increased expression of the FXR effector genes Fgf15 and Shp in the intestine (12.2 and 13.3-fold with Tyr-Chol at 24 hrs, p=0.029 and 0.009; 6.2 and 9.3-fold at 72 hrs, p=0.009 and 0.019, FIG. 3e, FIG. 12). Although Shp expression did not change detectably in the liver at 24 hrs after gavage, levels were increased 2.3-fold after 72 hrs (p=0.017, FIG. 3e, FIG. 12). Changes in expression of the bile acid synthesis genes Cyp7a1 and Cyp8b1 also showed a time dependent effect. Cyp7a1 was 9% of control levels at 24 hrs (p=0.001) and Cyp8b1 was at 69% (p=0.004, FIG. 12). At 72 hrs (4 gavages), Cyp7a1 expression was 8% of control (p=0.004) while Cyp8b1 the transcript was further reduced to 2% (p=0.0002, FIG. 3e). The strong time-dependent reduction of liver Cyp7a1 and Cyp8b1 transcripts indicates that similar to the primary bile acid cholic acid, gavage of mice with these compounds reduced the expression of downstream FXR target genes responsible for bile acid synthesis in the liver.

Bile acid metabolism by the microbiome has been described since the 1960s[40]. The four known mechanisms of microbial metabolism are dehydroxylation, dehydration and epimerization of the cholesterol backbone, and deconjugation of the amino acids glycine or taurine[1,41,42] The invention identifies a fifth mechanism of bile acid transformation by the microbiome mediated by a completely different mechanism: amide conjugation of the cholate backbone with the amino acids phenylalanine, tyrosine and leucine. Though there are homologues of the human bile acid conjugation gene BAAT in clostridial genomes, the microbial enzyme in question remains unknown. Regardless of the mechanism of their synthesis, these novel conjugates stimulate the human FXR receptor in a cell-based system and the expression of FXR-target genes responsible for bile acid production in the liver were reduced when administered to mice.

Conclusion: The invention shows that the chemistry of all organ systems are affected by the presence of a microbiome. The strongest signatures come from the gut, particularly via the breakdown of plant natural products from food and the manipulation of bile acids. The microbiome is primarily a catabolic entity, breaking down compounds through enzymatic removal of chemical groups. However, the invention discloses an anabolic reaction that represented a fifth mechanism of bile acid metabolism by the microbiome through unique amino acid conjugations of cholic acid. As the connections between humans and our microbial symbionts becomes increasingly appreciated, a combination of globally untargeted approaches and the development of tools that interlink these data sets, such as the GNPS and MASST analysis infrastructure, enables more efficient characterization of microbial molecules and efficient translation between model animals and human studies, leading to a better understanding of the deep connection between our microbiota, our metabolites, and our health.

Data Availability: All metabolomics data that support the findings of this invention are available at GNPS (gnps.ucsd.edu) under the MassIVE ID numbers: MSV000079949 (original GF and SPF mouse data), MSV000082480, MSV000082467, MSV000079134, MSV000082406, MSV000083032, MSV000083004, MSV000083446. The sequencing data for the GF and SPF mouse study is available on the Qiita microbiome data analysis platform at qiita.ucsd.edu under study ID 10801 and through the European Bioinformatics Institute accession number ERP109688.

Results

Figure 1C:
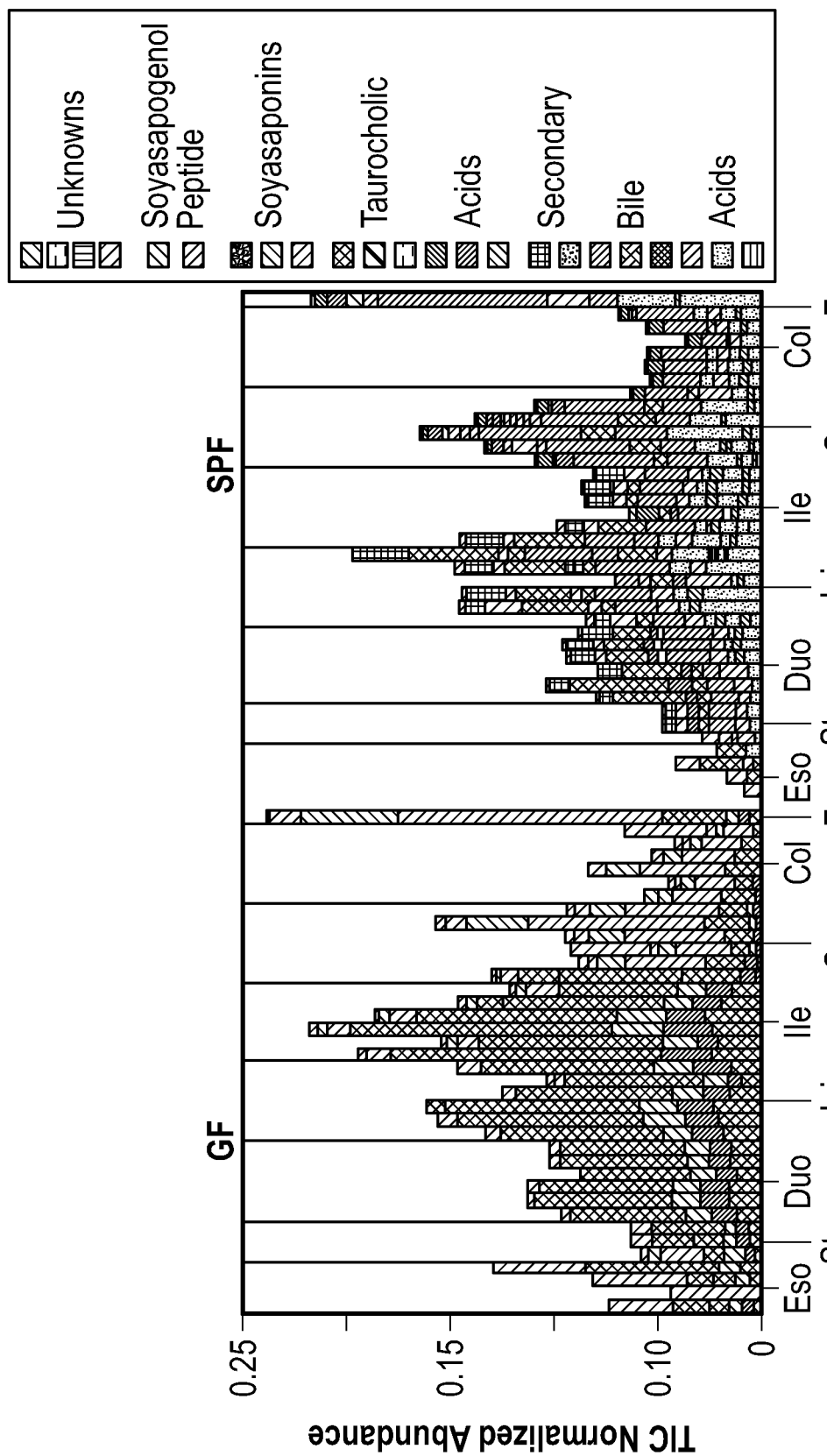
Figure 1D:
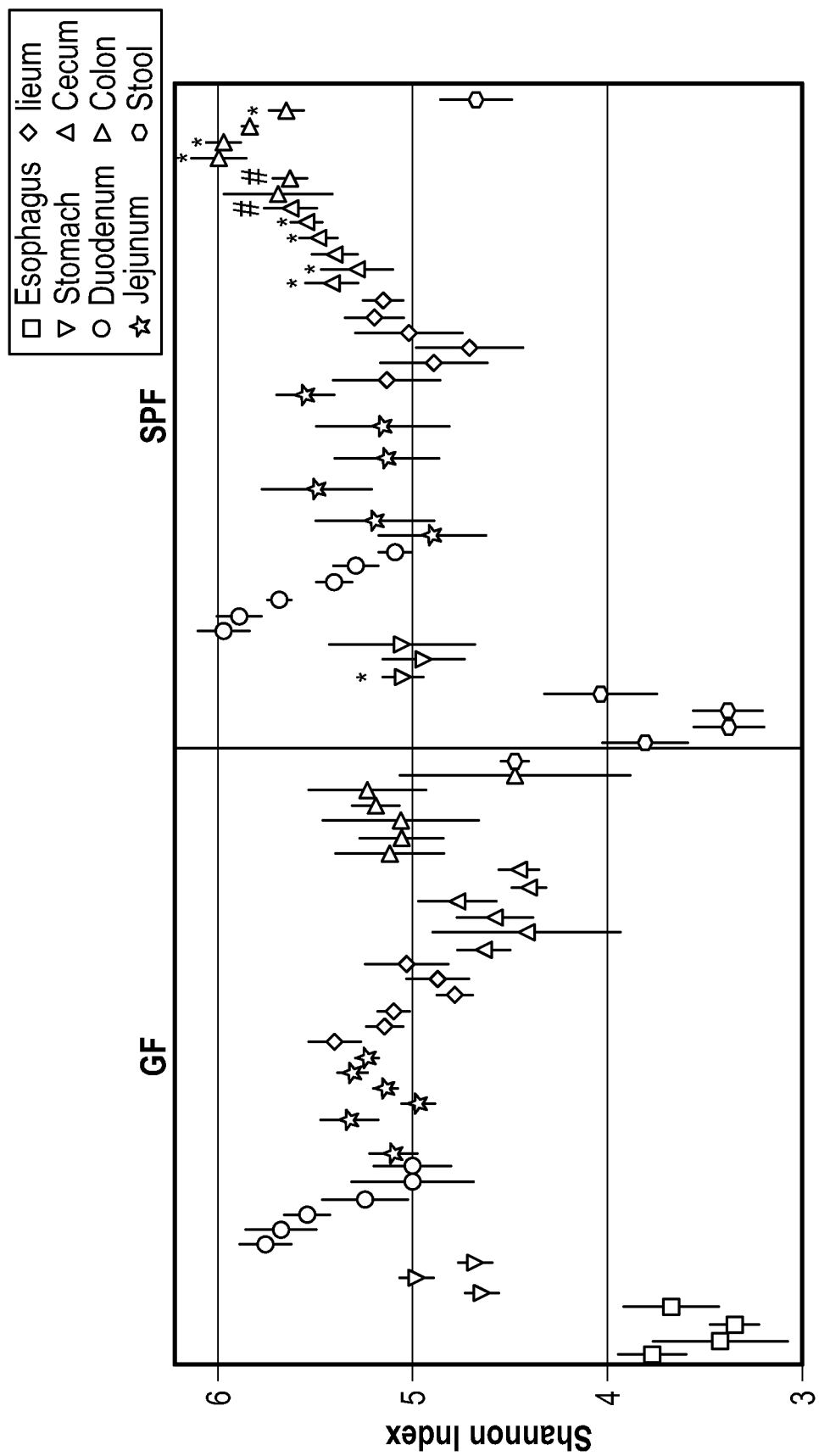
Figure 1E:
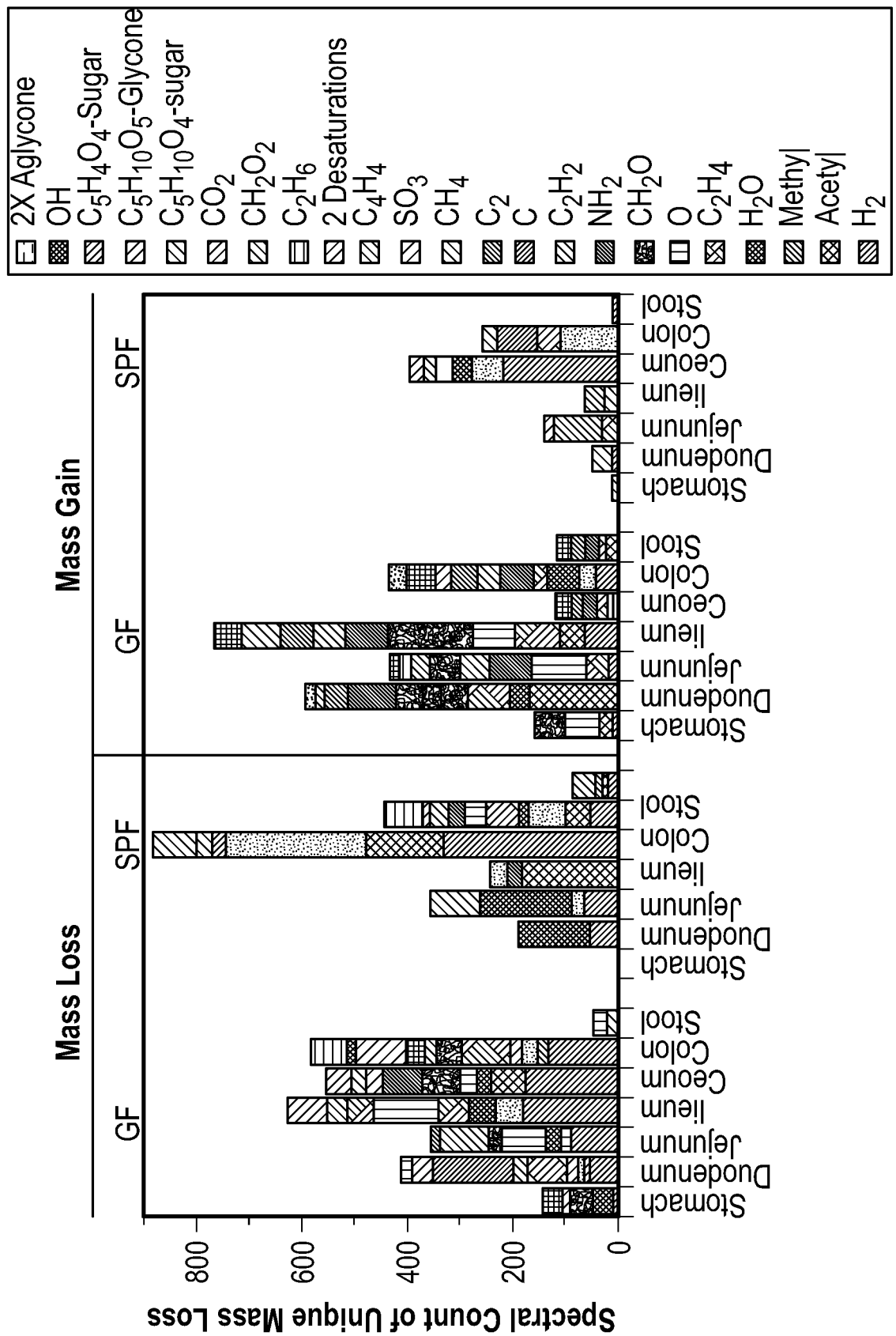

FIGS. 1a-1e. Global impacts of the microbiome on the chemistry of an entire mammal. FIG. 1a) 3-D model of murine organs mapped with the mean Pt principle coordinate as a heatmap according to the grayscale (from FIG. 4) from the GF and SPF mice (n=4). (Er=ear, Br=brain, Ad=adrenal gland, Es=esophagus, Tr=trachea, Sto=stomach, Kd=kidney, Mo=mouth, Duo=duodenum, Ov=ovary, Col=colon, F=feces, Hd=hand, Lg=lung, Lv=liver, Jej=jejunum, Cec=cecum, Bl—bladder, Ut=uterus, Cx=cervix, Vg=vagina, Ft=feet). FIG. 1b) Mean percent and total number of unique spectra in each organ sampled from the two mouse groups. FIG. 1c) Relative abundance (to total ion current (TIC)) of the 30 most differential metabolites between GF and SPF murine guts. The metabolites are secondary bile acids, primary bile acids, soyasaponins, peptides, and unknowns. Annotations are based on spectral matching or molecular network propagation (level two or three[3]). It must be noted that stereochemistry of the annotated molecules cannot be discerned using these methods. FIG. 1d) Mean and 95% confidence interval of the Shannon-Weiner diversity of the metabolomic data in each GI tract sample for GF and SPF mice. Statistical significance between metabolome diversity in the same sample location between GF and SPF mice was tested with the Mann-Whitney U-test (n=4, two-sided, *=p=0.028, #=p=0.057). FIG. 1e) Results of meta-mass shift chemical profiling[17] showing the spectral counts of known mass differences between unique nodes in either GF or SPF mice. Each mass difference corresponds to the node-to-node gain or loss of a particular chemical group.

FIGS. 2a-2b. Novel microbial bile acid conjugates. FIG. 2a) Structures and molecular networks of novel microbiome conjugated bile acids with the host-conjugated GCA shown for comparison. The molecular network is colored by mapping to either GF or SPF mice according to the legend with an inset highlighting the parent masses and mass differences between the newly discovered molecules and GCA. Each node represents a clustered MS/MS spectrum and connections between the nodes indicate relationships through the cosine score with their width scaled by the cosine size (cutoff minimum 0.7). Circular nodes are unknowns and arrowheads are spectra with matches in the GNPS libraries. FIG. 2b) Dot plot of the area under curve abundance of the novel and host synthesized bile acid conjugates in each SPF mouse (n=4) through the murine GI tract and its subsections.

Figures 4A, 4B:
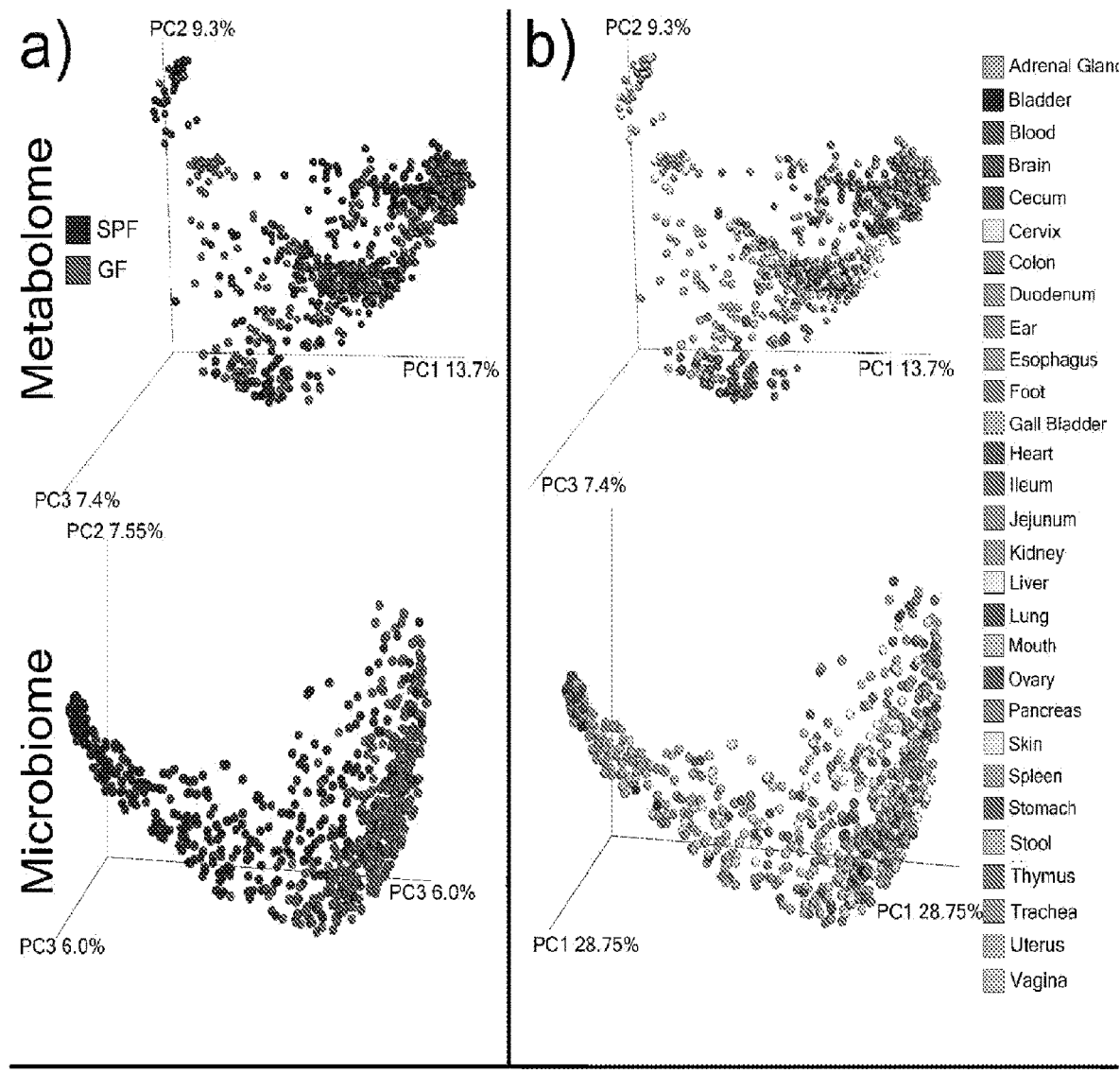
FIGS. 4a-4e show microbiome and metabolome diversity in GF and SPF mice.
Figure 4C:
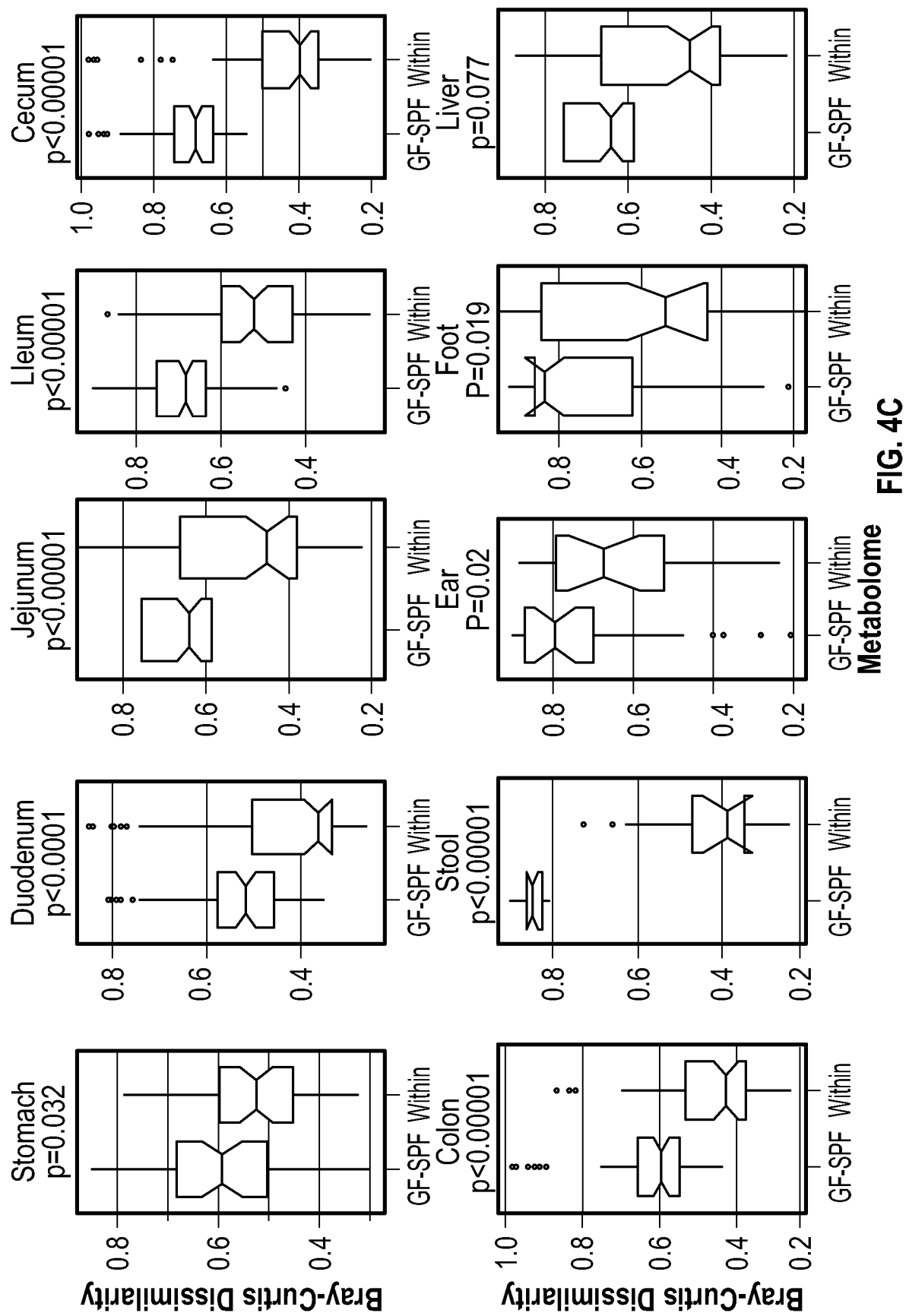
Figure 4D:
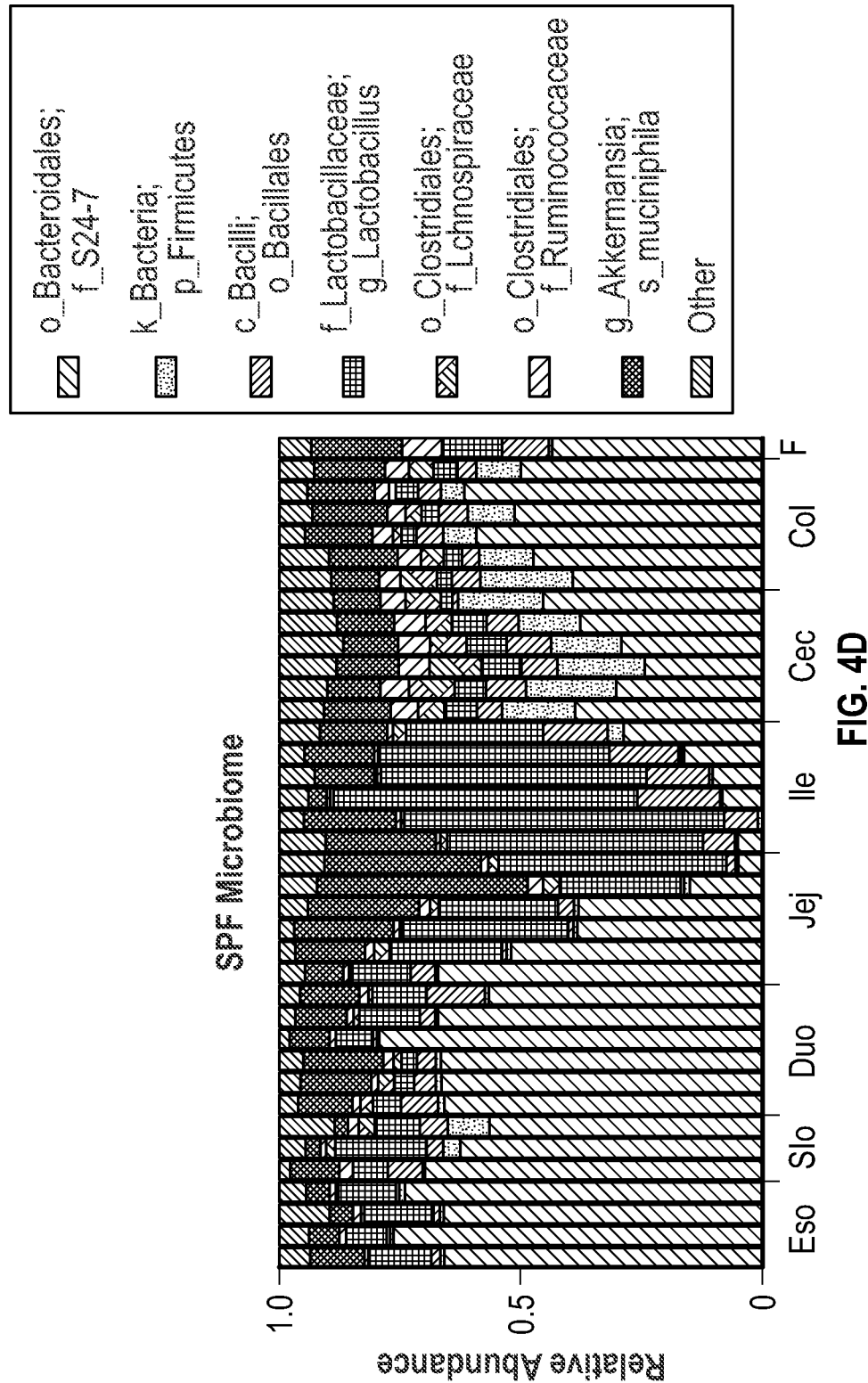
Figure 4E:
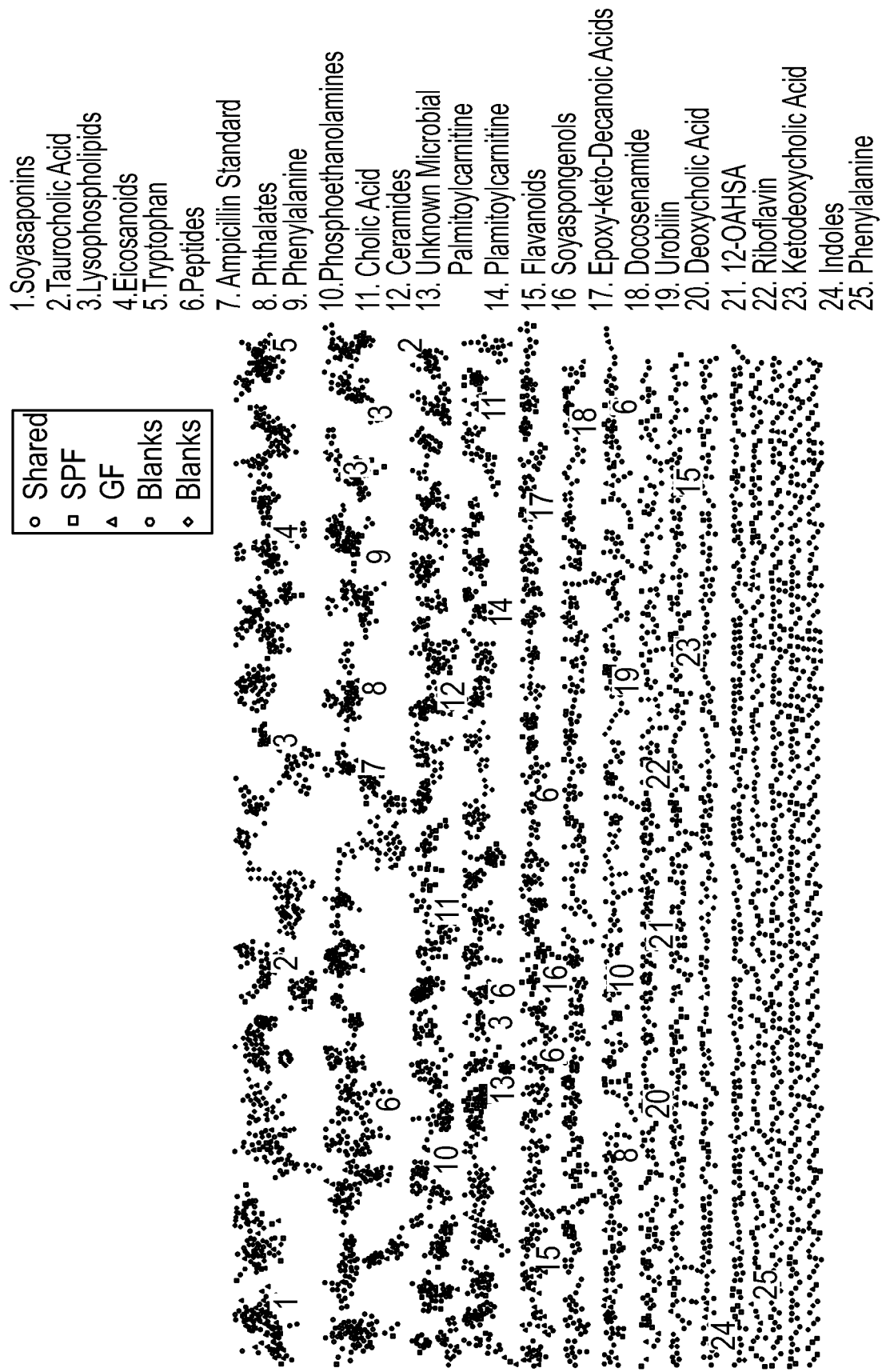

FIGS. 3a-3e. Presence, synthesis and function of microbial bile acid conjugates. FIG. 3a) Percent of samples positive for the novel bile acids from GNPS public datasets (AGP=American gut project[28], CF=cystic fibrosis) and pediatric CF patients compared to non-CF controls (PS=Pancreatic Sufficient, PI=Pancreatic Insufficient, color coding of bile acids refers to panels a-c). FIG. 3b) Abundance of novel conjugates in the PRISM and HMP2 datasets[31]. Statistical significance for PRISM data was tested using the Wald's test (CD n=68; UC n=53; non-IBD n=34) and for the iHMP dataset with a linear mixed-effects model (two-sided). The iHMP comparisons are separated by IBD type and dysbiotic or non-dysbiotic states (UC n=12 dysbiotic and n=110 non-dysbiotic metabolomes; for CD n=48 dysbiotic and n=169 non-dysbiotic; non-IBD dysbiotic n=15, non-IBD non-dysbiotic n=107). Significance is shown using Benjamini-Hochberg corrected p-values (Leu q=0.031, Tyr q=0.0074, Phe q=0.0043, *q<0.05, **q<0.05). Boxes represent the IQR, notch is the 95% confidence interval of the mean, center is the median, and whiskers are 1.5×the IQR. FIG. 3c) Extracted ion chromatograms of Phe-chol from cultured isolates of C. bolteae compared to media control at 0 h and 96 h (top, repeated twice). d) The ratio of $^{13}C:^{12}C$ Phe-chol in mouse fecal samples fed a high fat diet with $^{13}C$-labelled phenylalanine (grey line) or unlabeled phenylalanine (black line) through time. Grey area indicates 3-day period where HFD was fed, red greyscales indicates when HFD was supplemented with Phe. FIG. 3e) RT-qPCR data showing mean and standard error of the gene expression ratio (ddCt) of Fgf15, Shp, Cyp7b1 and Cyp7a1 to the 36B4 (RPLPO) reference control in the ileum and/or liver of mice gavaged with different bile acids compared to a mock control (corn oil) after 72 hrs. Statistical significance was tested against the mock control with a two-tailed T-test (n=4–5/group, whiskers in the plot are the standard error). CA=cholic acid FIGS. 4a-4e. Microbiome and Metabolome Diversity in GF and SPF mice. FIG. 4a) Principal coordinates analysis (PCoA) of microbiome and mass spectrometry data highlighted by sample source as GF or SPF (n=4). The microbial signatures from the GF mice are an important control that represent background reads found in buffers, tips and tubes and other experimental materials. FIG. 4b) Same data highlighted by organ source (n=4). FIG. 4c) Bray-Curtis dissimilarities of the metabolome data collected from murine organs. The dissimilarities are calculated within individual mice of the same group (GF or SPF, "Within") or across the GF and SPF groups ("GF-SPF") (n=4). Only samples collected from exact same location (sub-section) are compared. Significance tested with the Mann-Whitney U-test (two sided, Boxes represent the IQR, the notch is the 95% confidence interval of the mean, the center is the median, and whiskers are 1.5×the IQR). FIG. 4d) Microbiome profile of the murine GI tract in SPF mice. Data was generated by sequencing 16S rRNA gene amplicons from each organ and organ section and analyzed through the Qiita Deblur pipeline as described in the methods. Taxa of relevance are coded according to the legend. FIG. 4e) Molecular network of LC-MS/MS data with nodes colored by source as GF, SPF, shared, or detected in blanks. Molecular families with metabolites annotated by spectral matching in GNPS are listed by a number corresponding to the molecular family. These are level 2 or 3 annotations according to the metabolomics standards consortium[16]. 12-OAHSA=12-(9Z-Octadecenoyloxy)-octadecanoic acid.

Figure 5A:
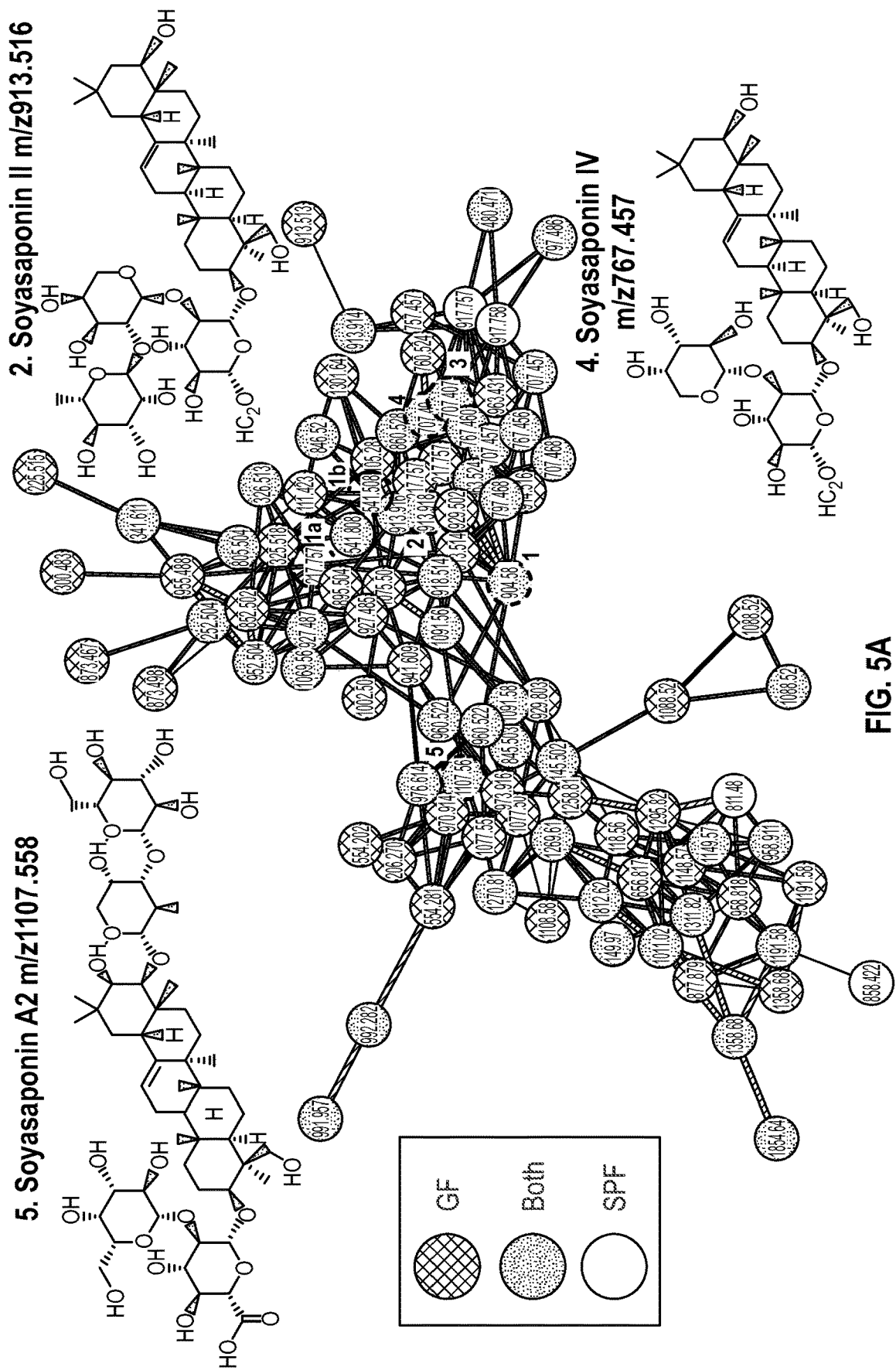
FIGS. 5a-5f show the microbial metabolism of soyasaponins in GF and SPF metabolomics.
Figure 5A:
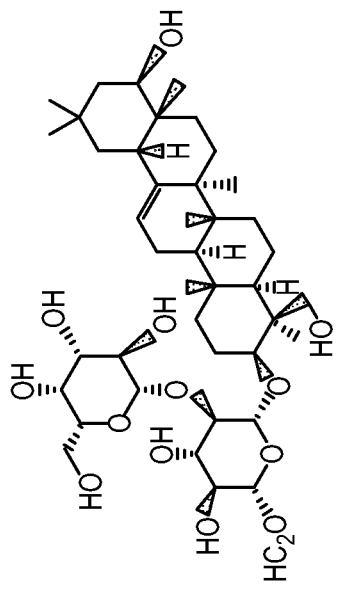
Figure 5A:
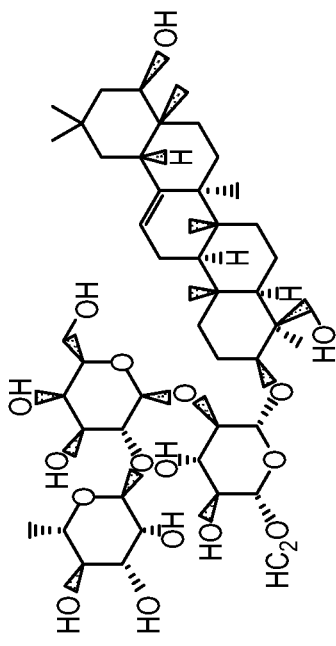
Figure 5A:
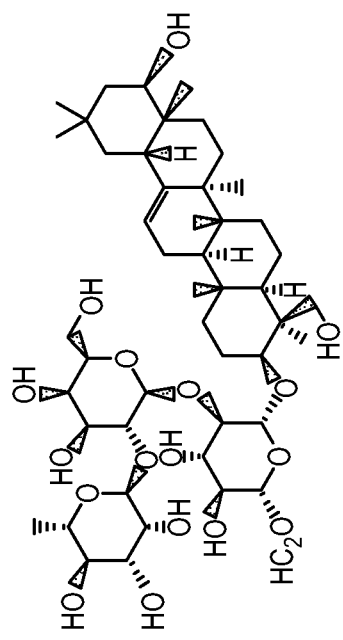
Figure 5A:
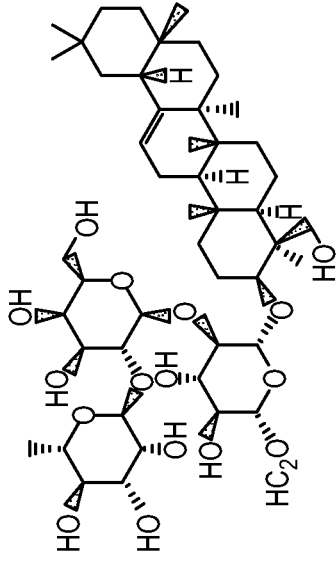
Figure 5A:
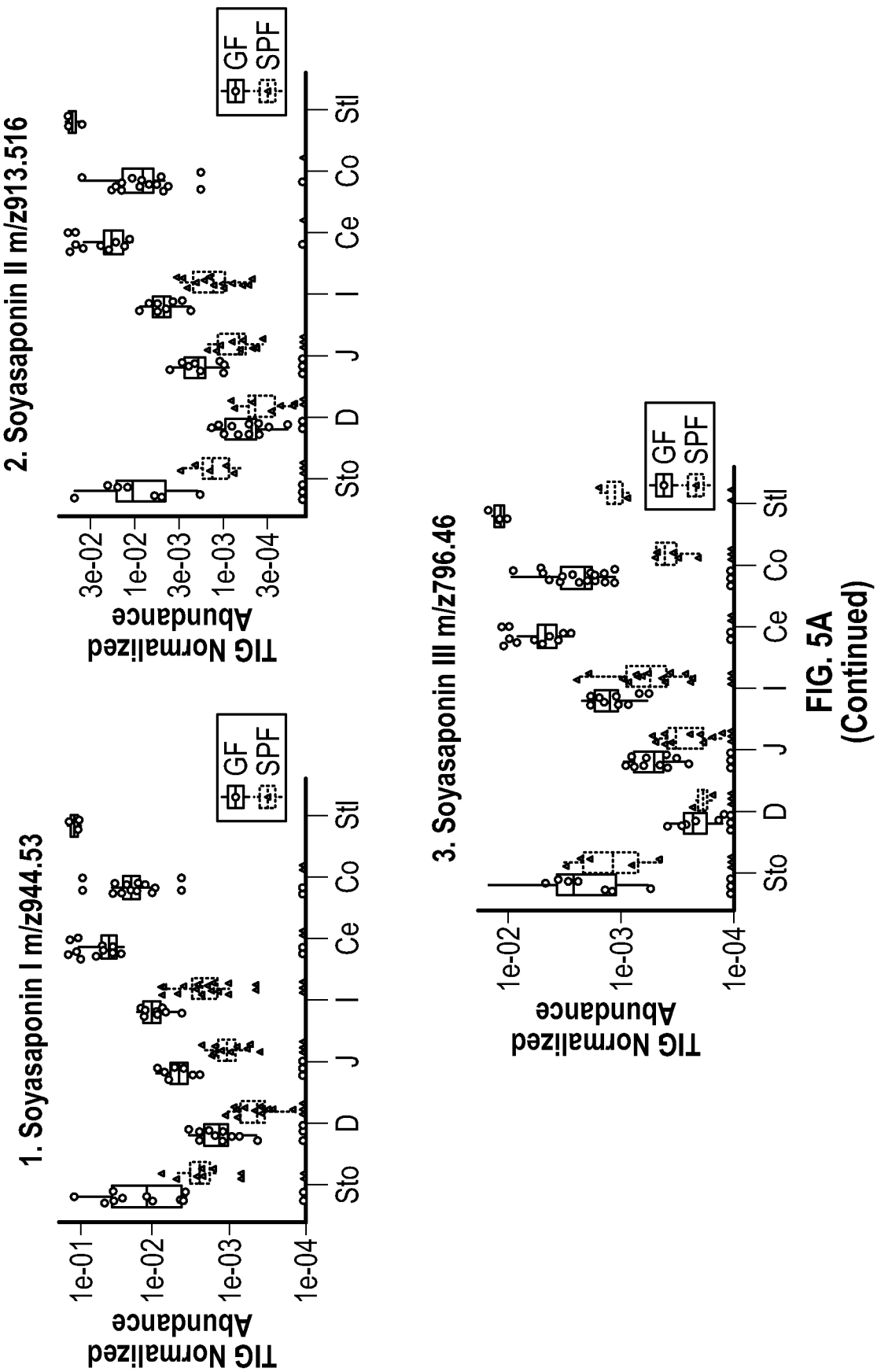
Figure 5A:
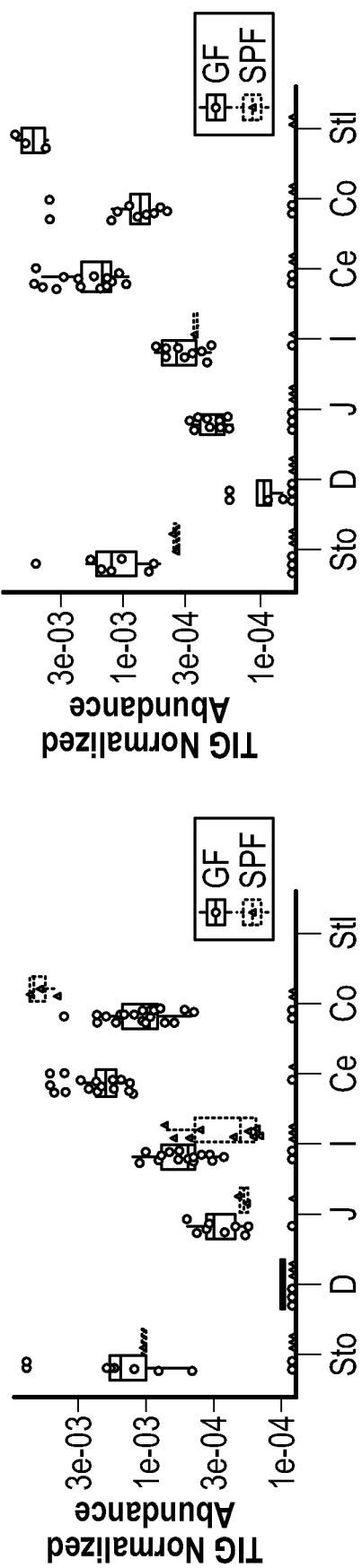
Figure 5A:
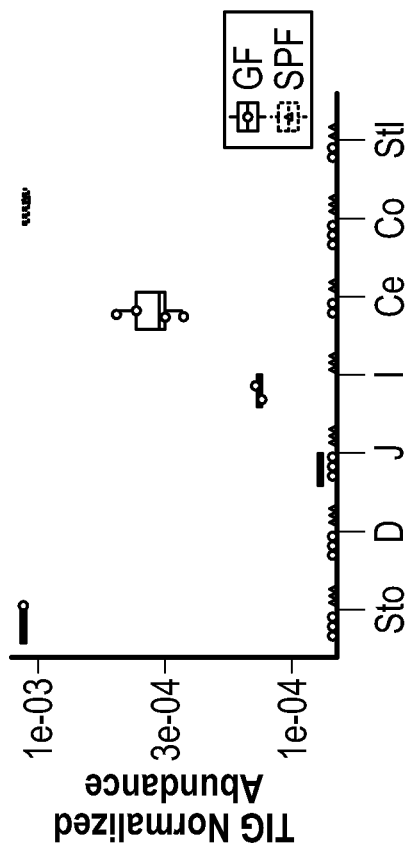
Figure 5B:
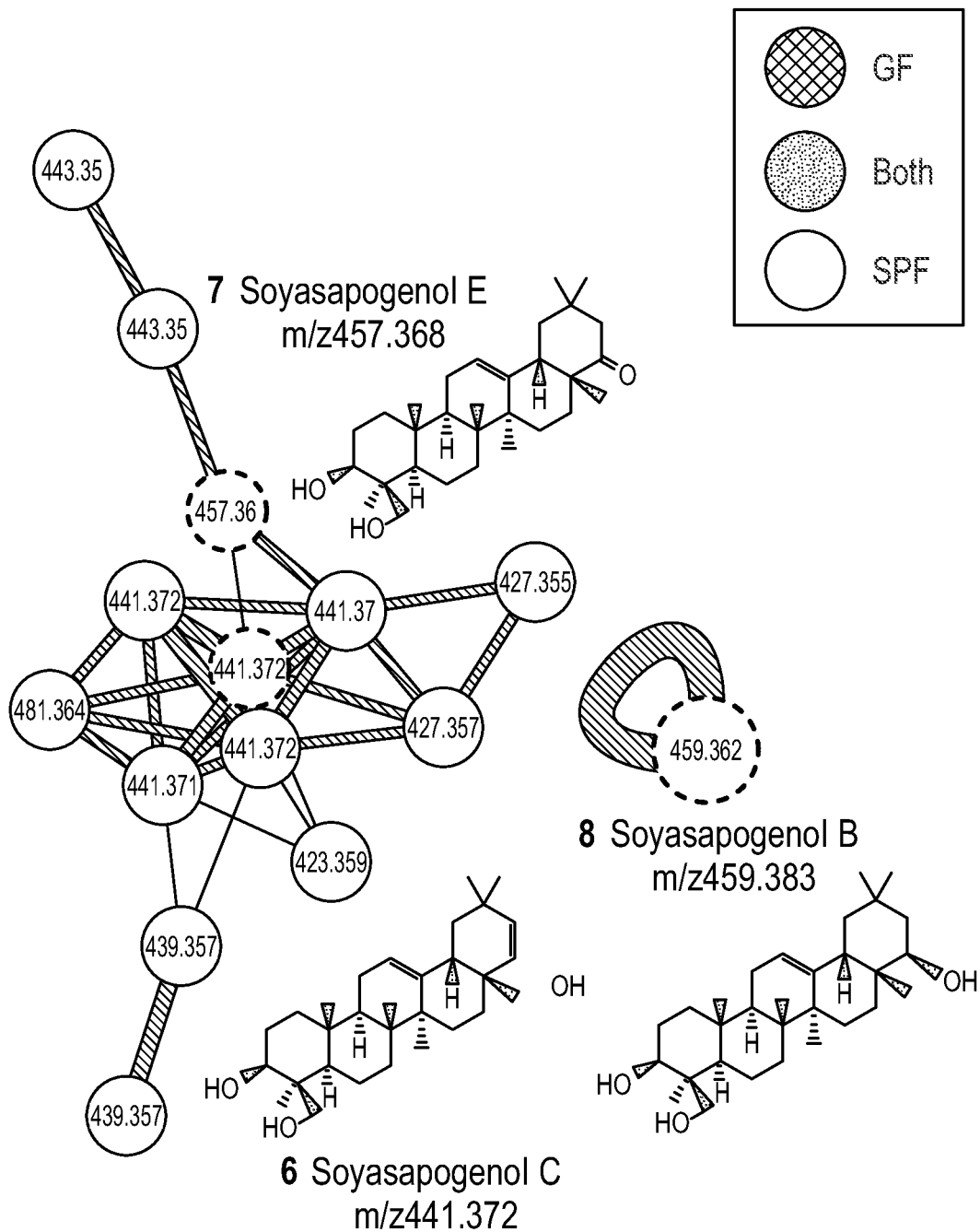
Figure 5B:
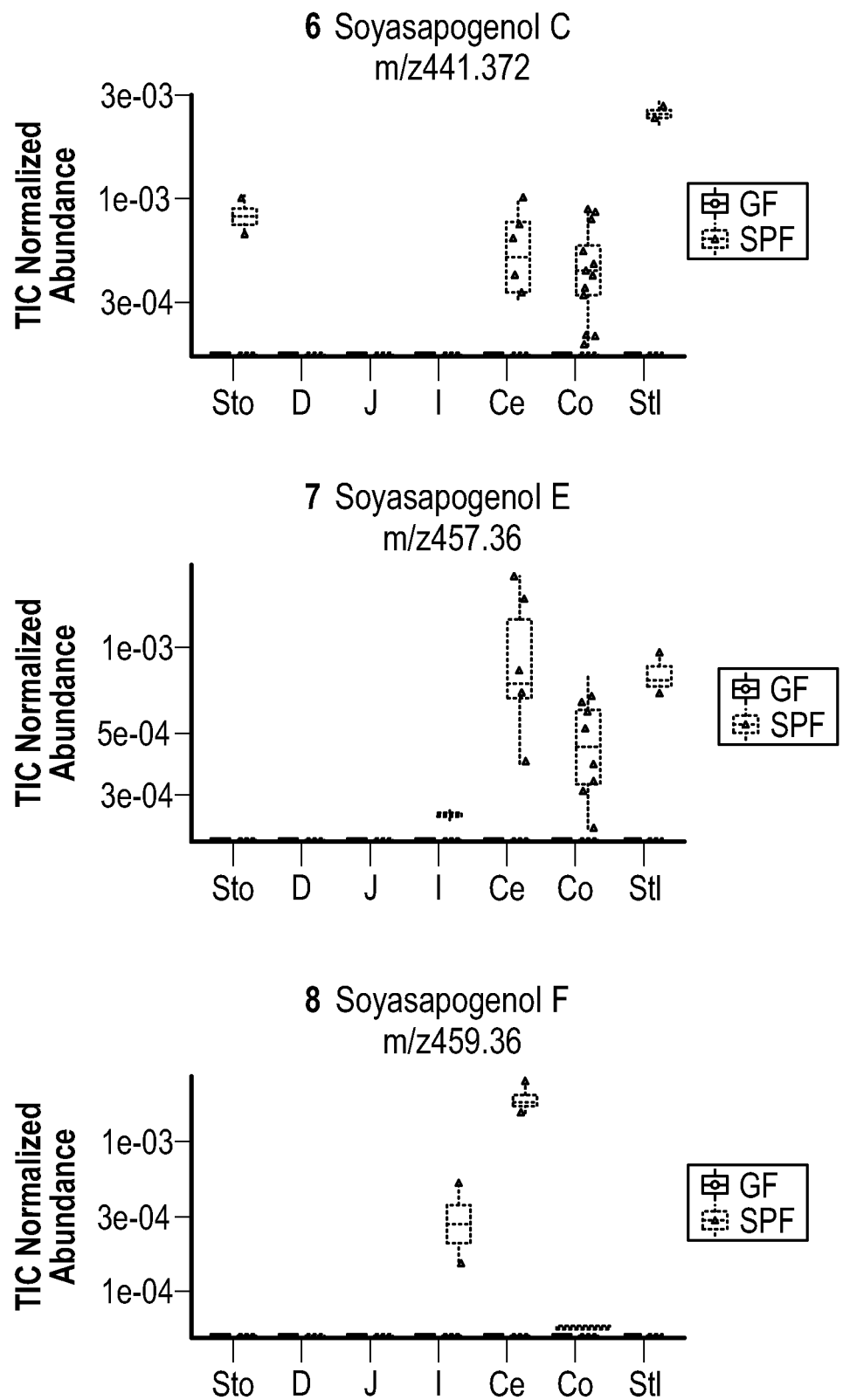
Figure 5C:
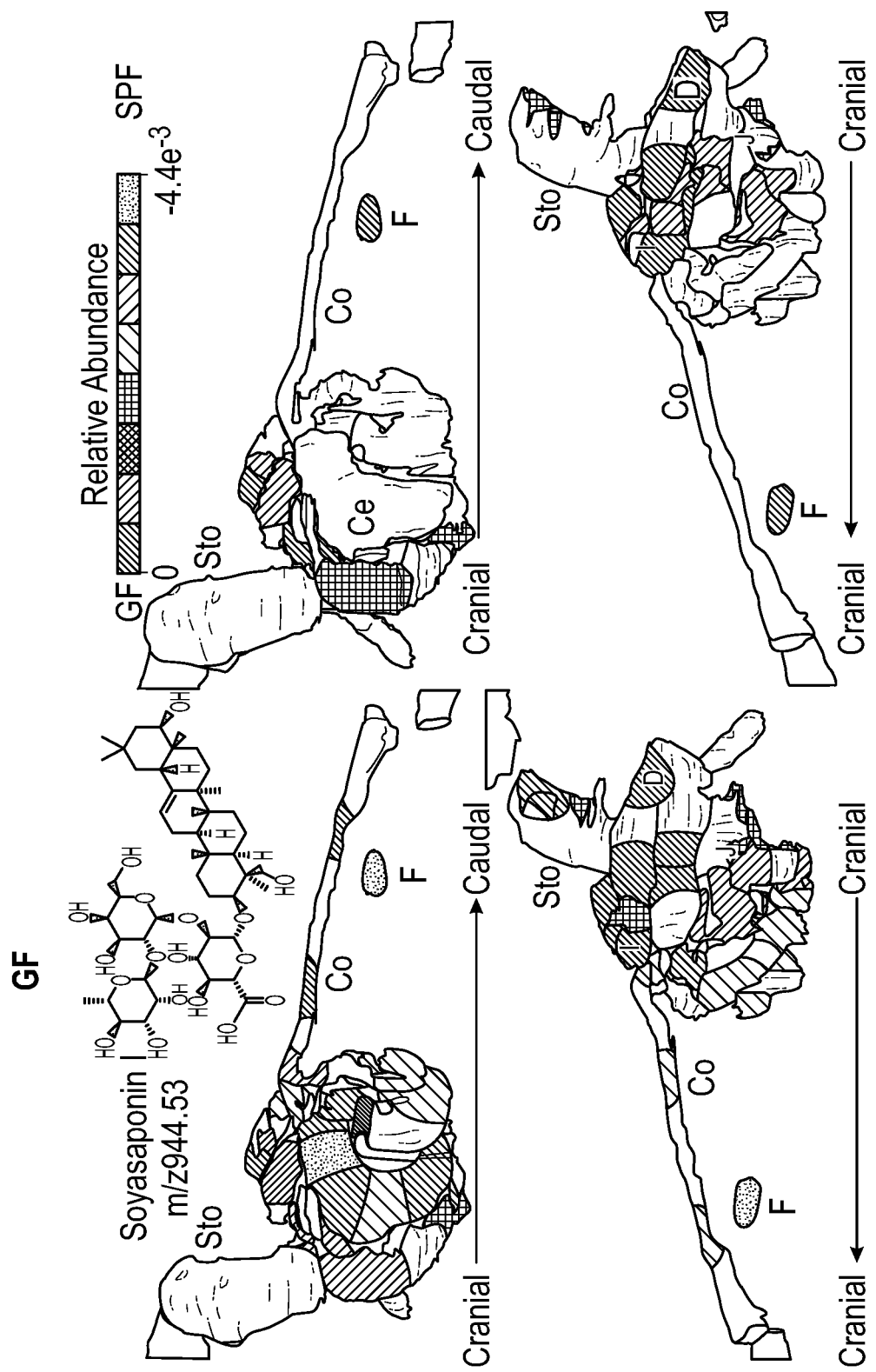
Figure 5D:
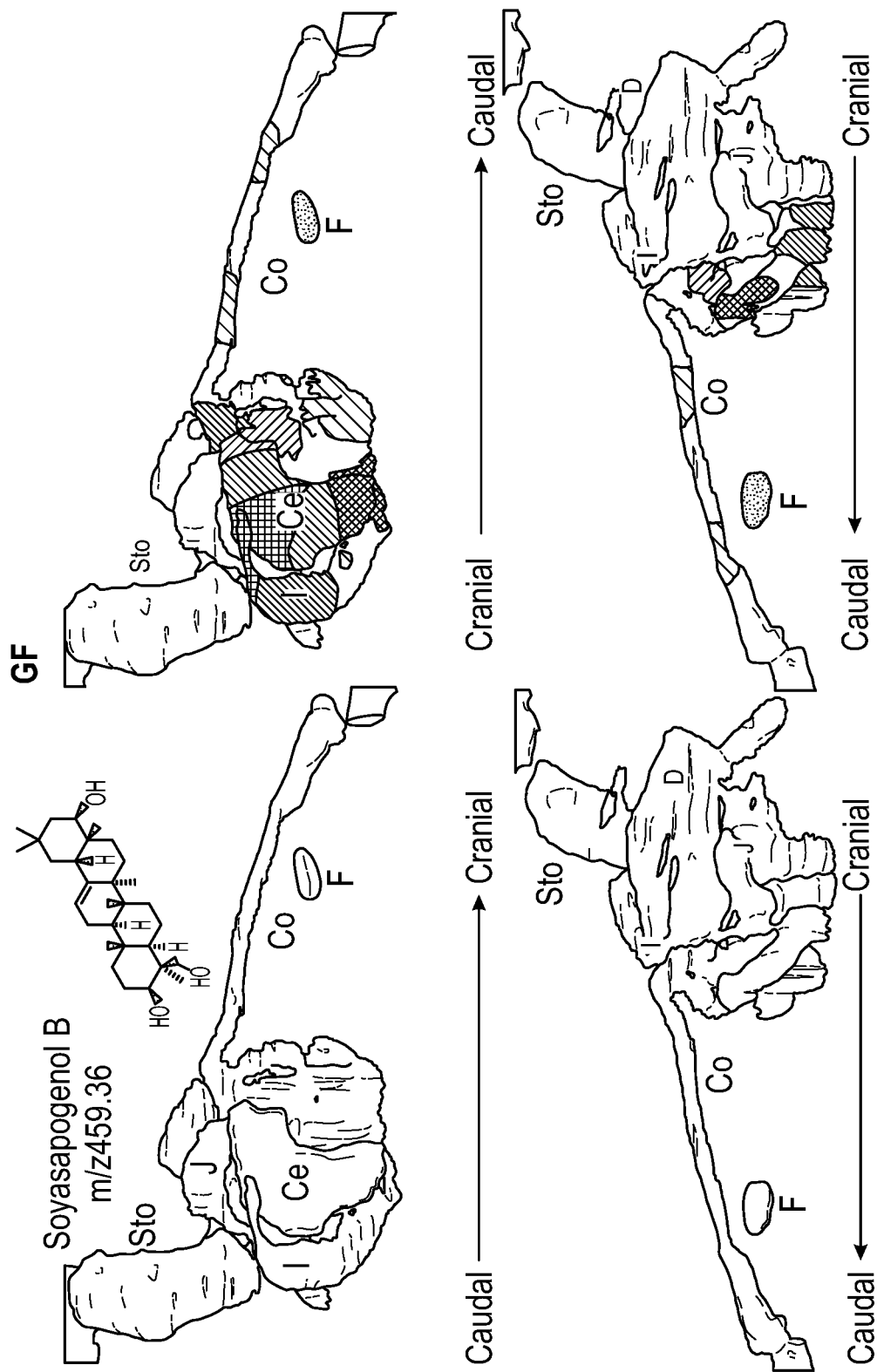
Figure 5E:
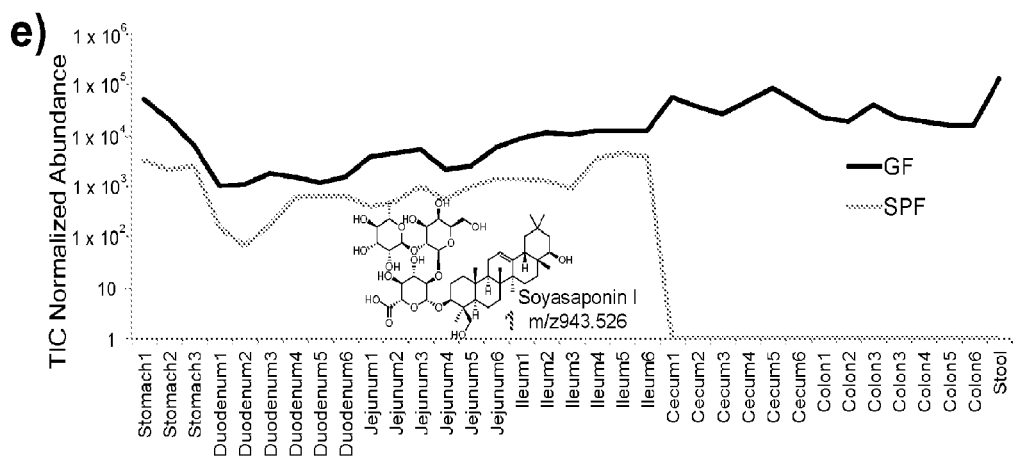
Figure 5F:
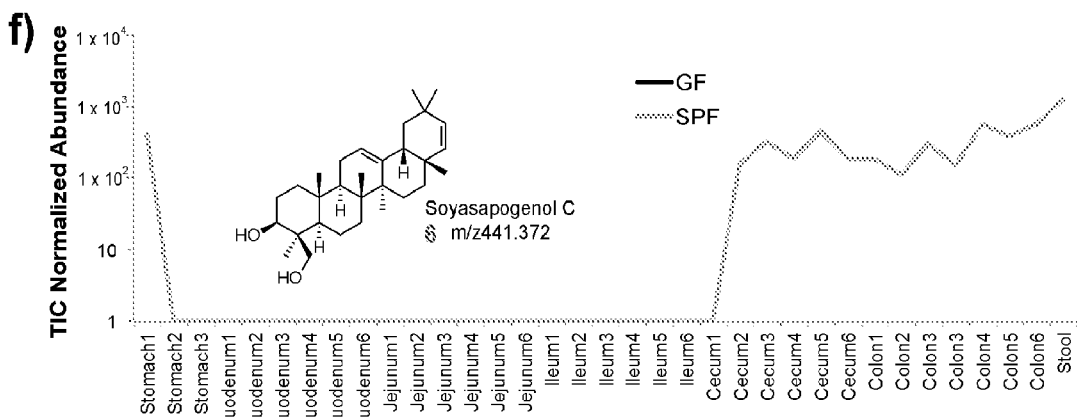

FIGS. 5a-5f. Microbial metabolism of soyasaponins in GF and SPF metabolomics data (n=4). FIG. 5a) Molecular network cluster of soyasaponins greyscale by source of each node as GF, SPF or shared. Structures of corresponding molecules are shown in nodes highlighted according to the numbering scheme. Mean total ion current normalized (TIC) abundance of each soyasaponin metabolite from the murine GI tract in the GF and SPF mice (Sto=Stomach, D=Duodenum, J=Jejunum, I=Ileum, Ce=Cecum, Co=Colon, Stl=Stool) (Boxes represent the IQR, the center is the median, and whiskers are 1.5×the IQR, n=4). FIG. 5b) Molecular family of soyasapogenols, their structures and relative abundances in GF and SPF gut organs (data same format a s in a)). FIG. 5c) 3-D model visualization of the normalized abundance of soyasaponin I in the murine GI tract. Abundance of the metabolite is indicated according to the viridis spectrum (greyscale) n=4. FIG. 5d) 3D cartography of the normalized abundance of soyasapogenol B onto an MRI organ model of the mice. FIG. 5e) Mean normalized abundance of soyasaponin I through all GI sample locations in the GF and SPF mice. f) Mean normalized abundance of soyasapogenol through all GI sample locations. The annotations are level 2 or $3^3$.

Figure 6A:
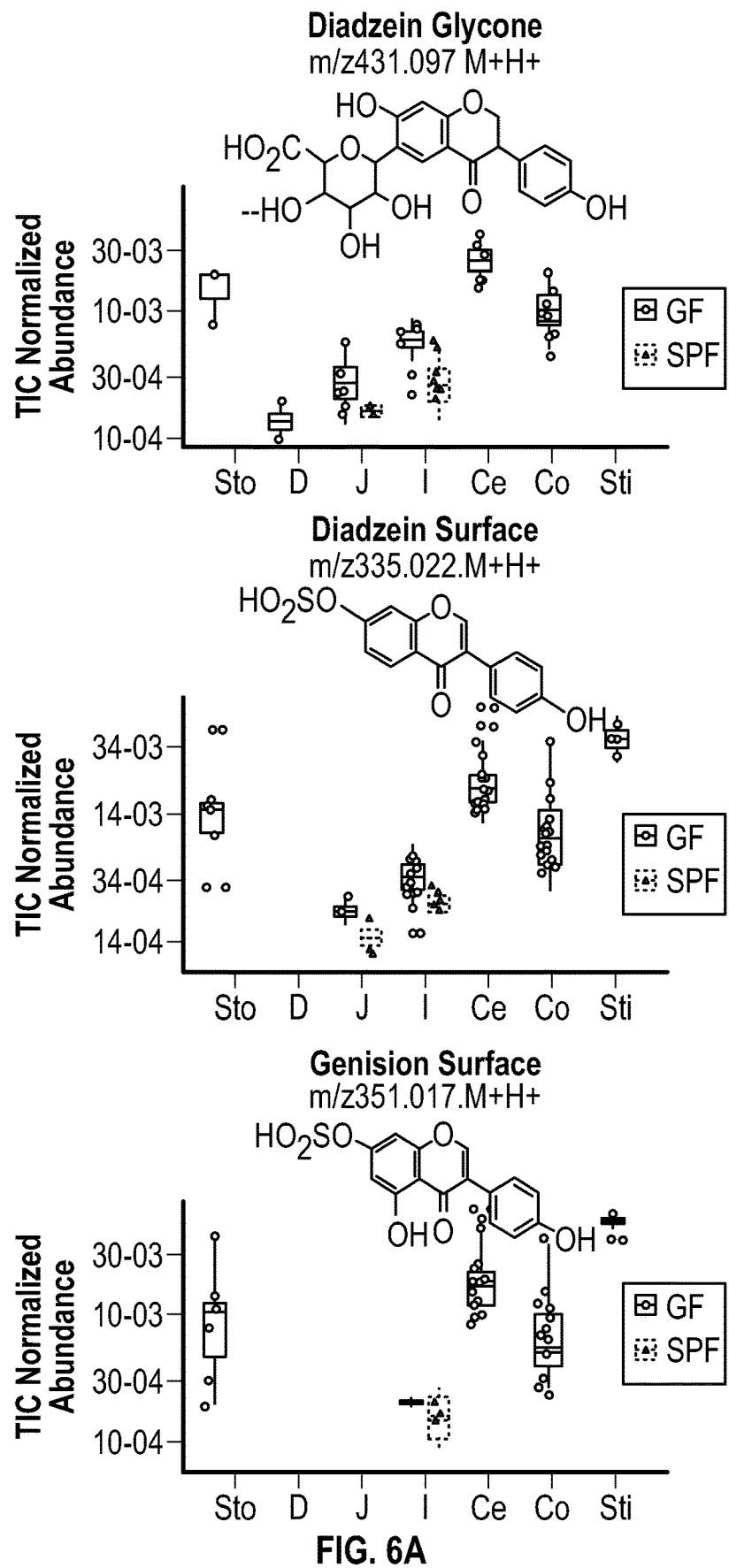
FIGS. 6a-6d show the microbial metabolism of plant isoflavones in GF and SPF metabolomics data.
Figure 6A:
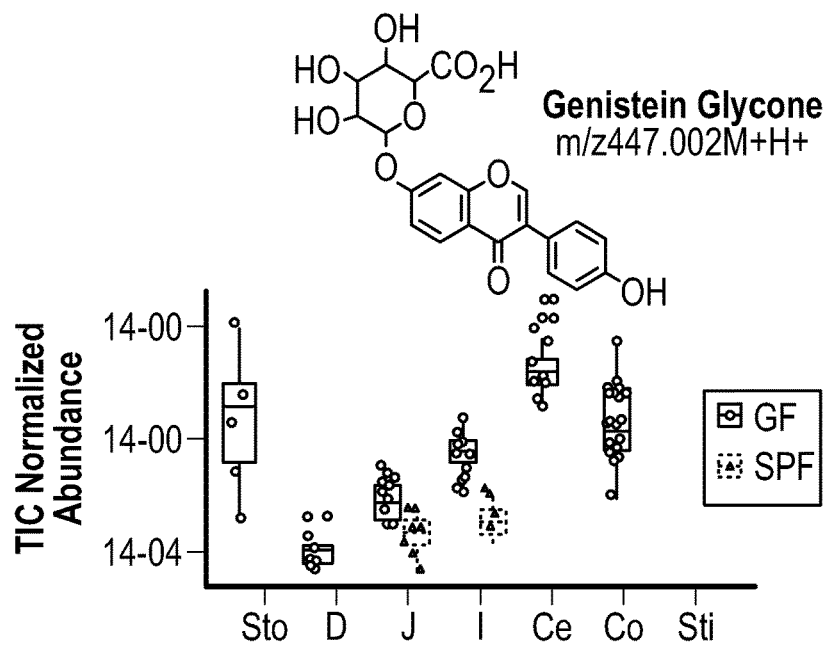
Figure 6A:
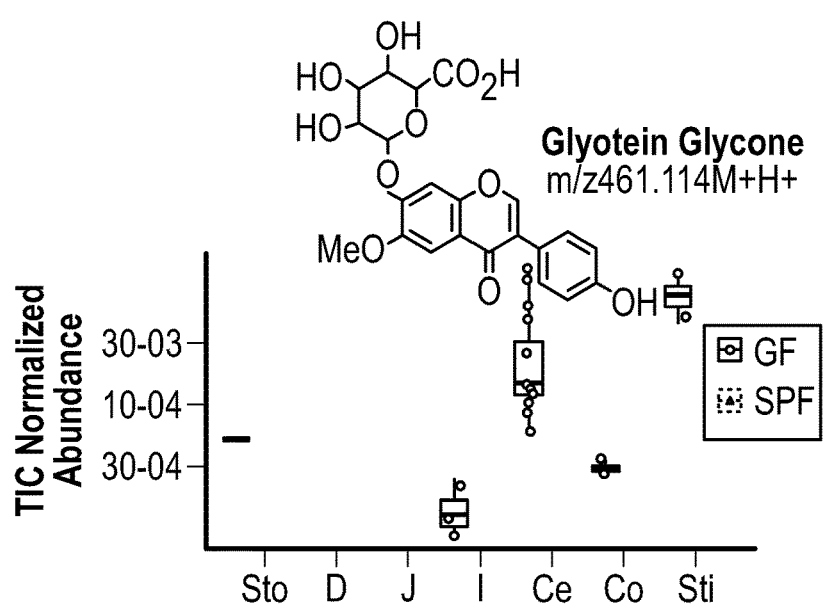
Figure 6A:
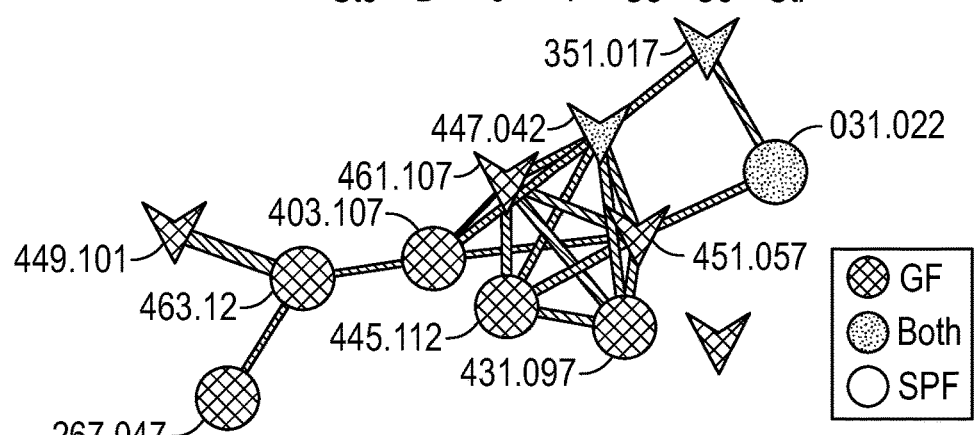
Figure 6B:
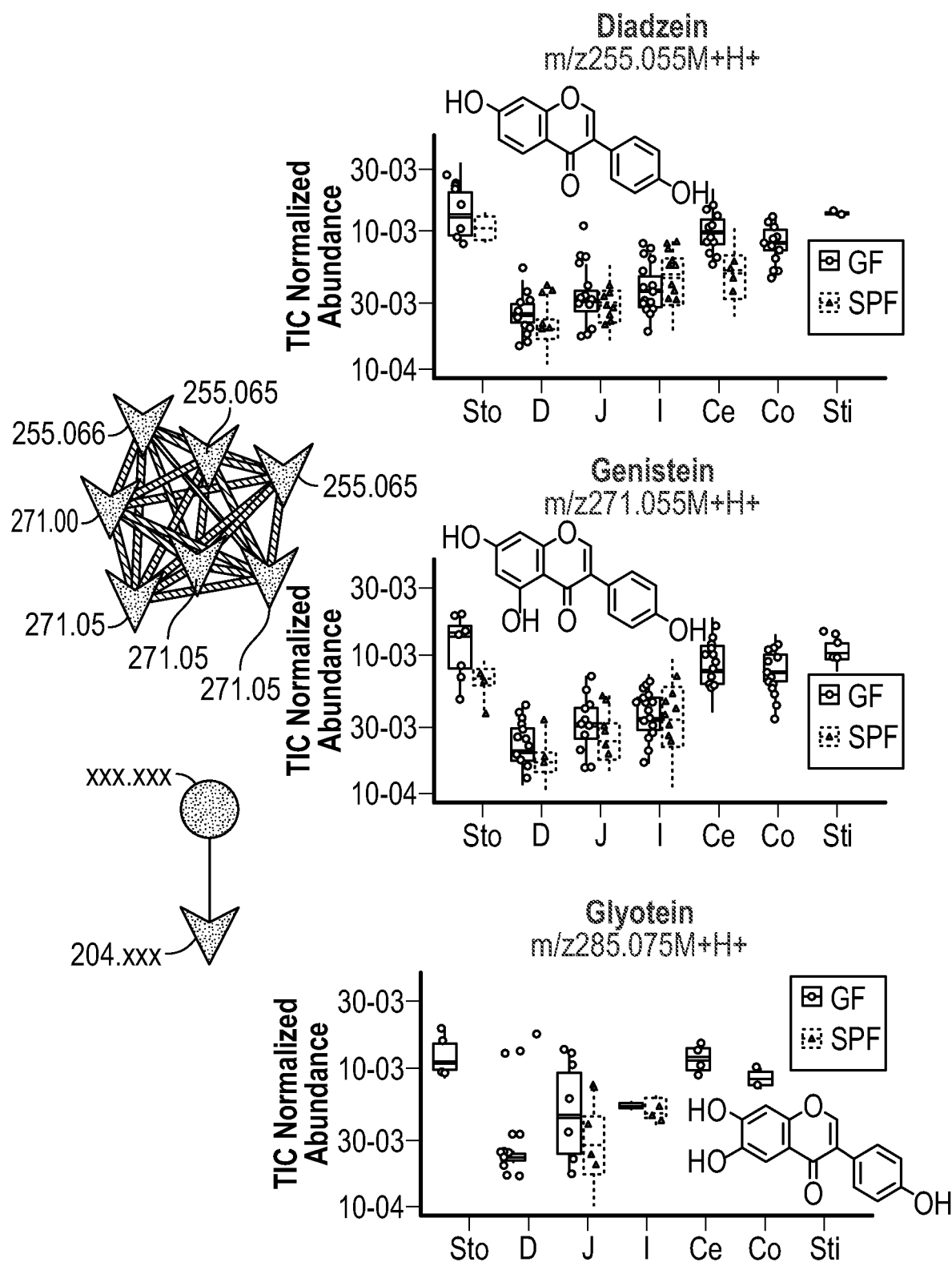
Figure 6C:
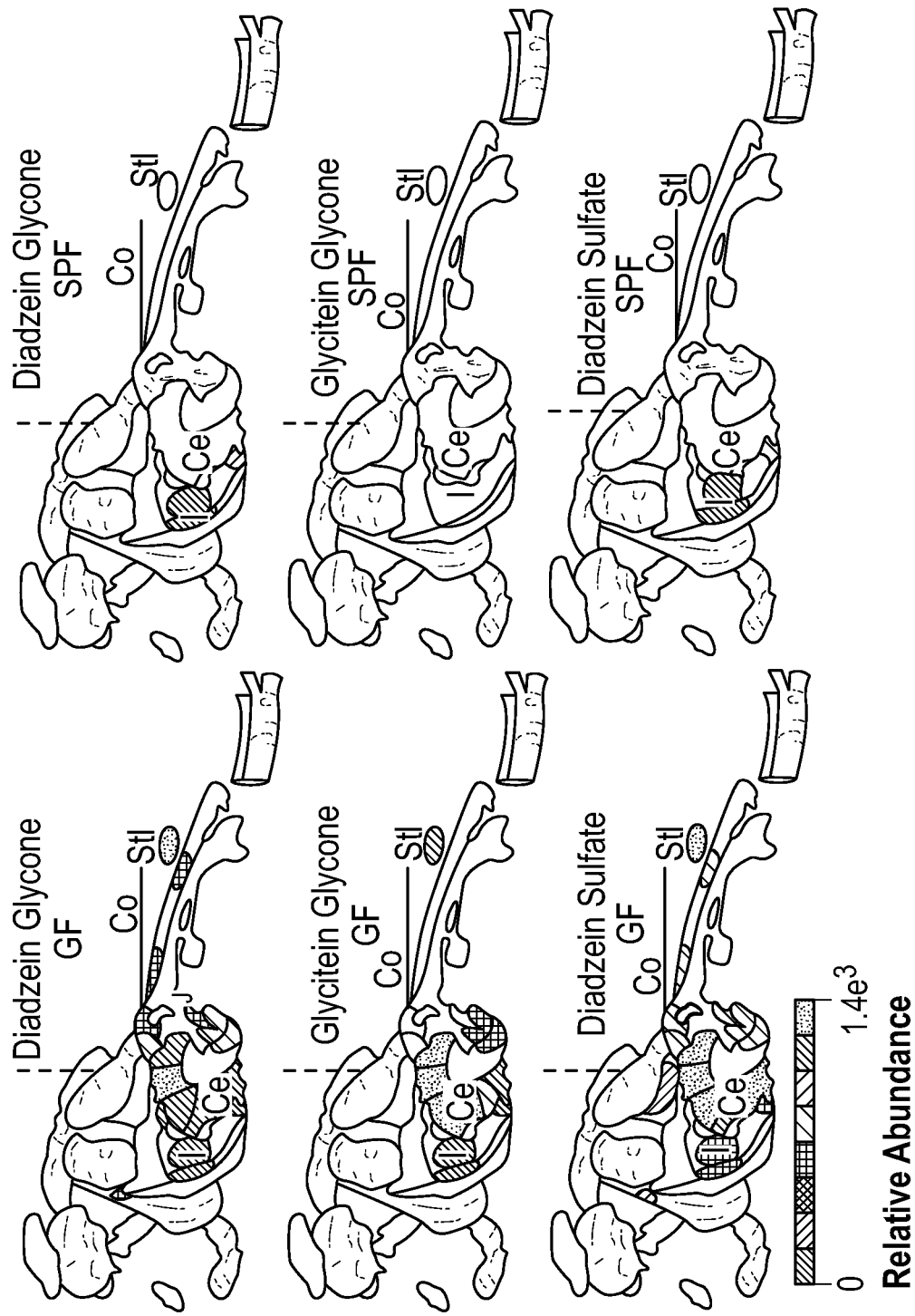
Figure 6D:
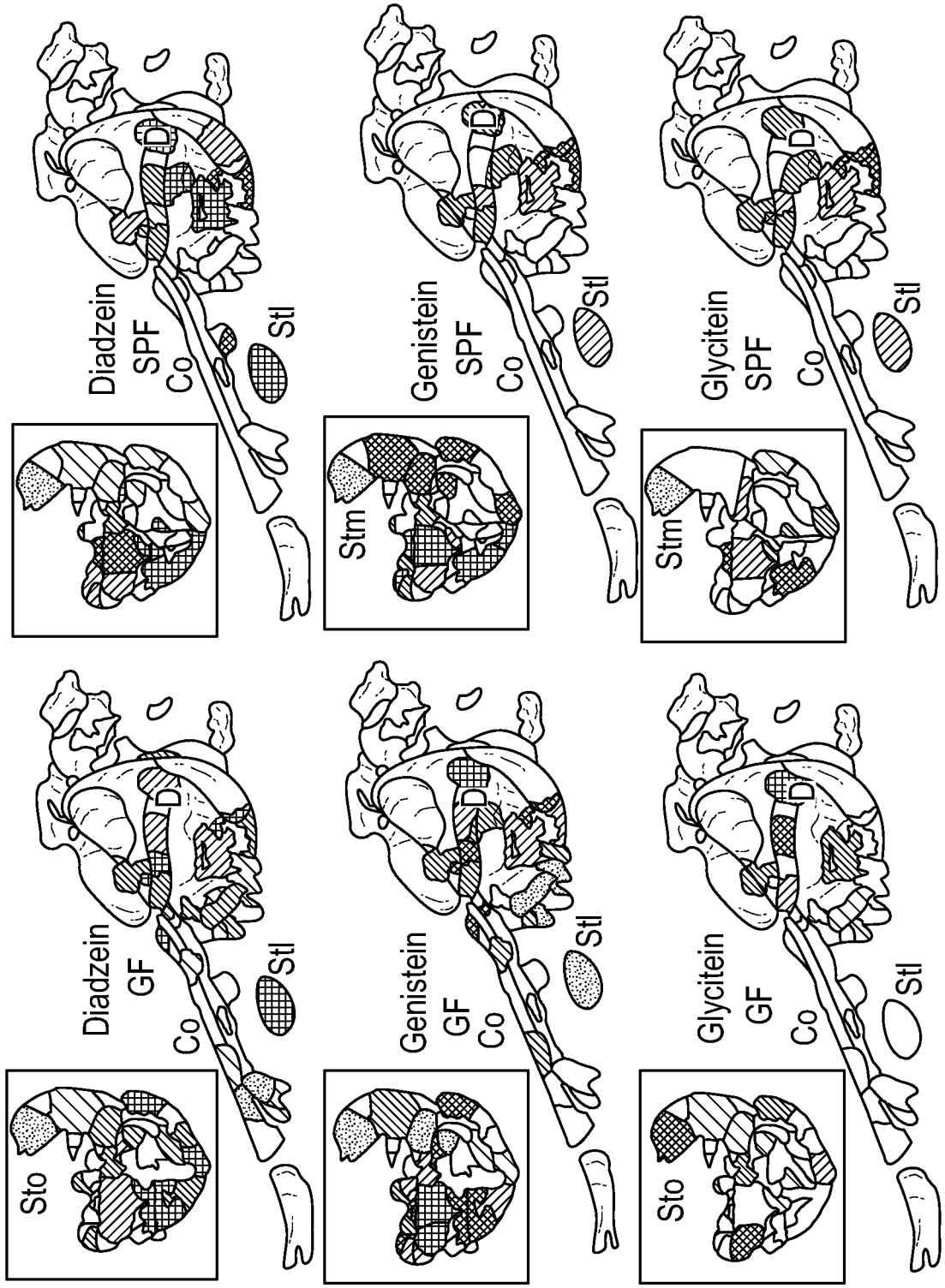

FIGS. 6a-6d. Microbial metabolism of plant isoflavones in GF and SPF metabolomics data. FIG. 6a) Structures, molecular network and total ion chromatogram (TIC) normalized abundance of glycone isoflavanoids in the murine GI tract. Nodes are greyscale according to their source in GF or SPF mice (n=4) and known library hits are shaped as arrowheads (Sto=Stomach, D=Duodenum, J=Jejunum, I=Ileum, Ce=Cecum, Co=Colon, Stl=Stool, Boxes represent the IQR, the center is the median, and whiskers are 1.5×the IQR, n=4). FIG. 6b) Same information for the aglycones. FIG. 6c) 3D-molecular cartography mapping the abundance of the daidzein and glycitein glycone and sulfated forms through entire 3D-mouse model. The normalized abundance of a particular molecule is indicated as a heat map. FIG. 6d) 3D-molecular cartography mapping the abundance of the daidzein and glycitein aglycone forms through entire 3D-mouse model. The GI tract model only is inset for reference. The annotations are level 2 or $3^3$.

Figure 7A:
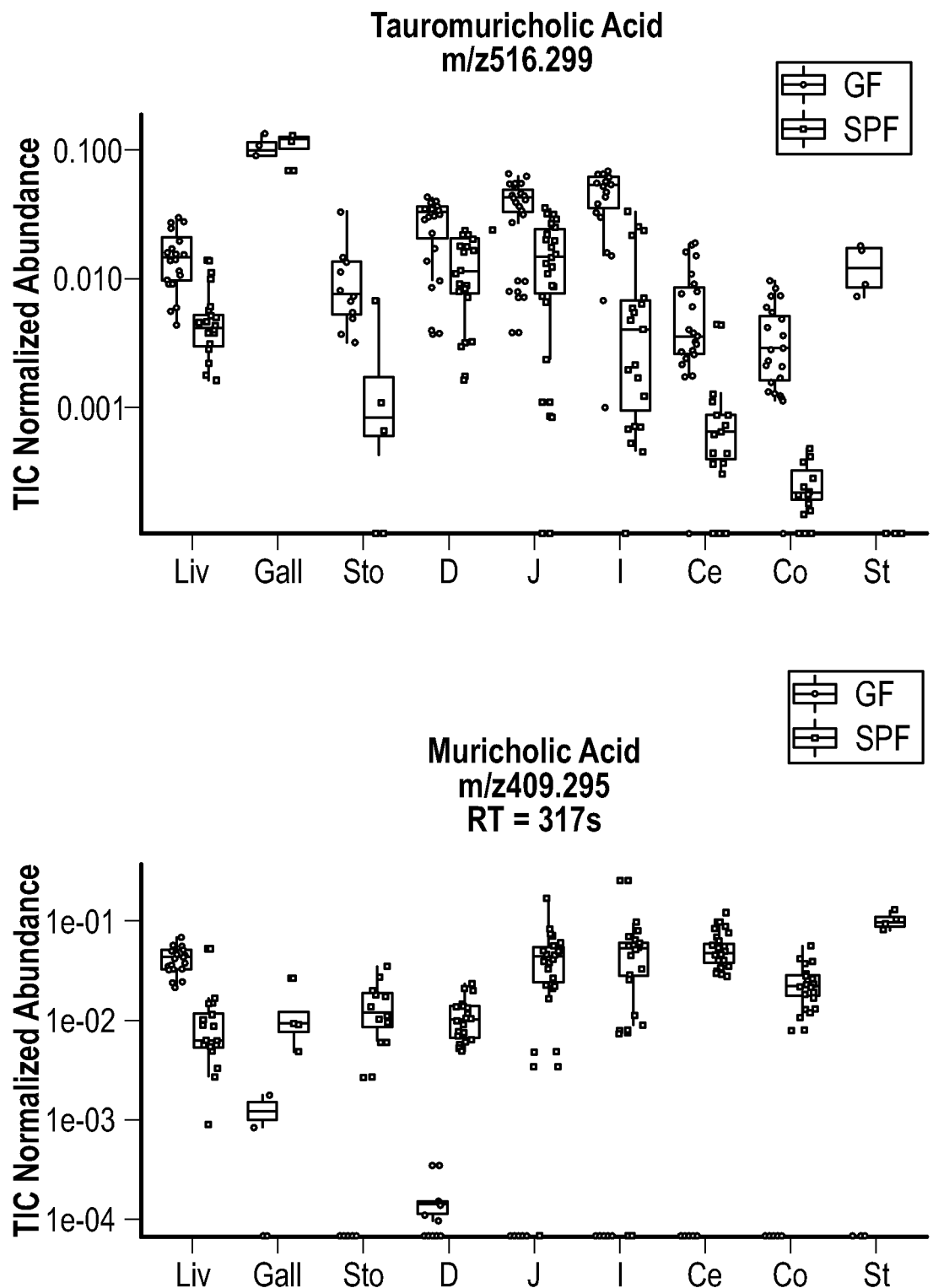
FIGS. 7a-7b show the microbial metabolism of known bile acids in GF and SPF metabolomics data.
Figure 7A:
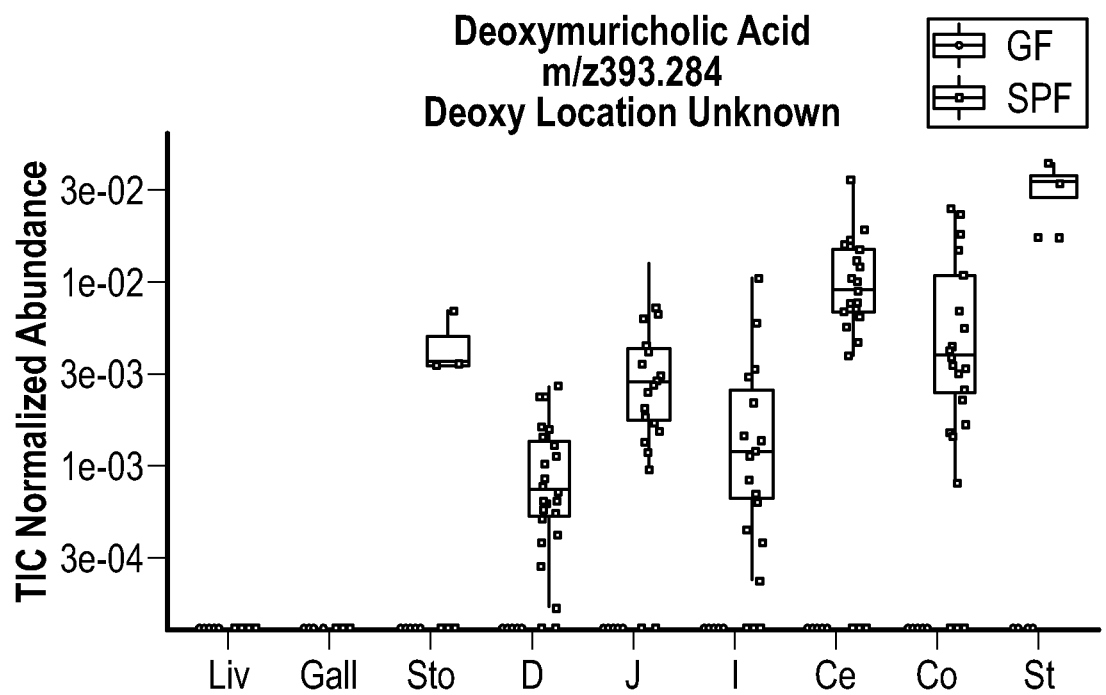
Figure 7A:
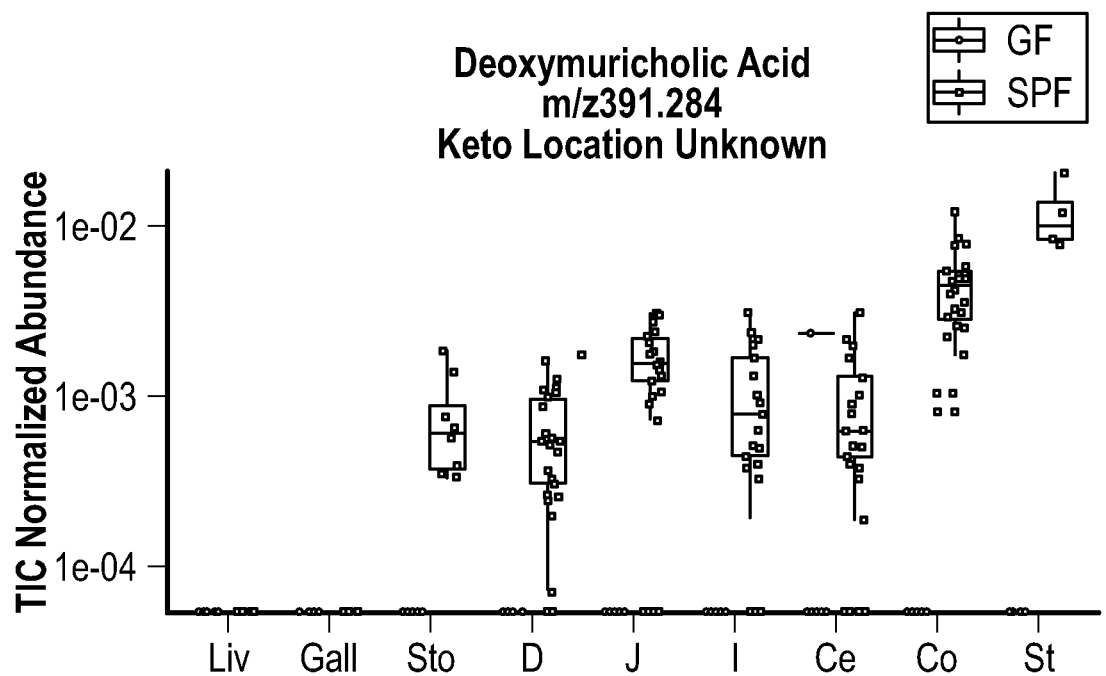
Figure 7B:
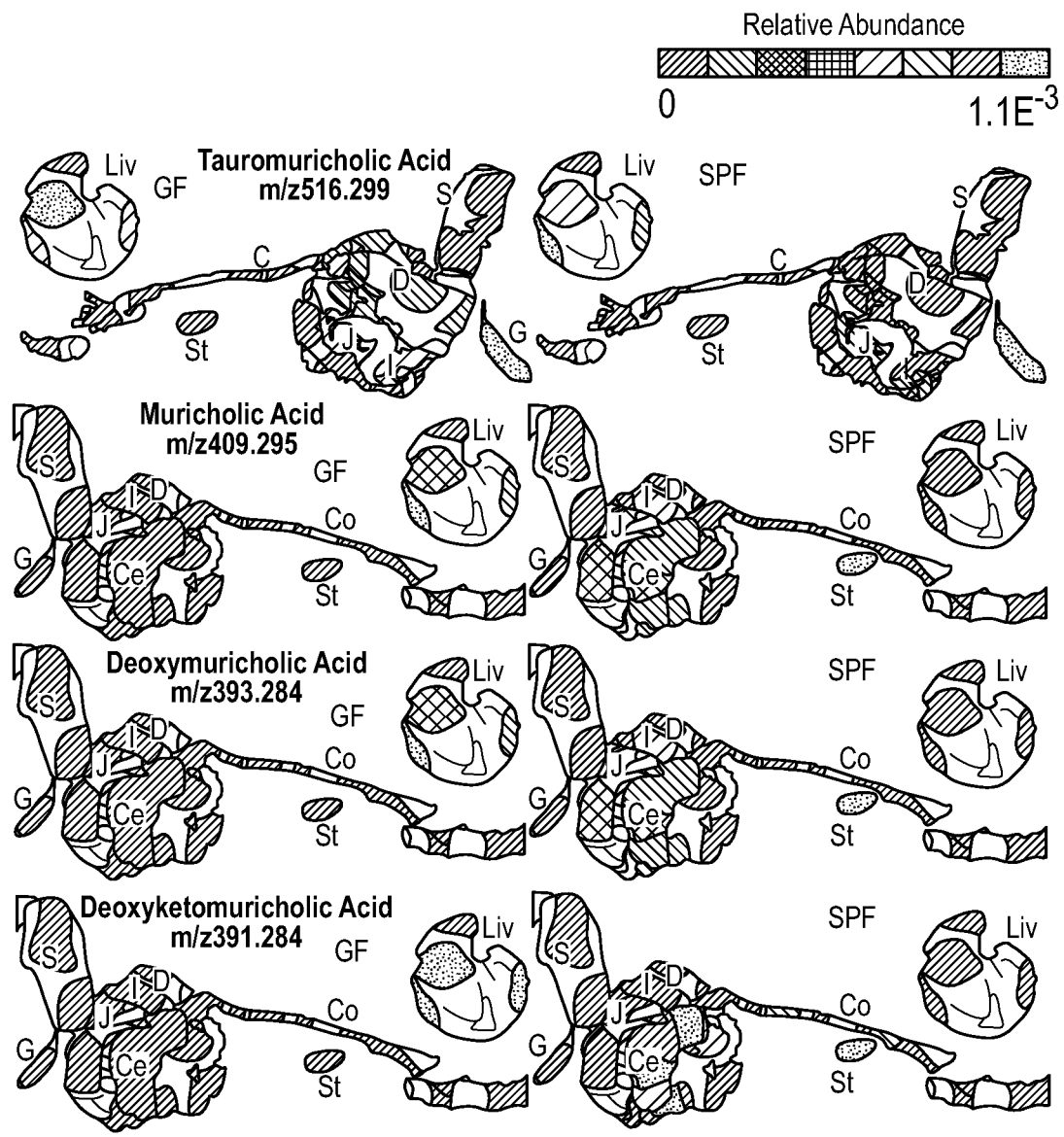

FIGS. 7a-7b. Microbial metabolism of known bile acids in GF and SPF metabolomics data (n=4). FIG. 7a) Total ion chromatogram (TIC) normalized abundance of taurocholic acid and secondary bile acids in GF and SPF mice GI tract samples (Liv=Liver, G=Gall, Sto=Stomach, D=Duodenum, J=Jejunum, I=Ileum, Ce=Cecum, Co=Colon, Stl=Stool Boxes represent the IQR, the center is the median, and whiskers are 1.5×the IQR). FIG. 7b) 3D-molecular cartography mapping the abundance of the same bile acids through the mouse GI tract model including liver separated for better visualization. The normalized abundance of a particular molecule is indicated as a heat map. The annotations are level 2 or $3^3$.

Figure 8A:
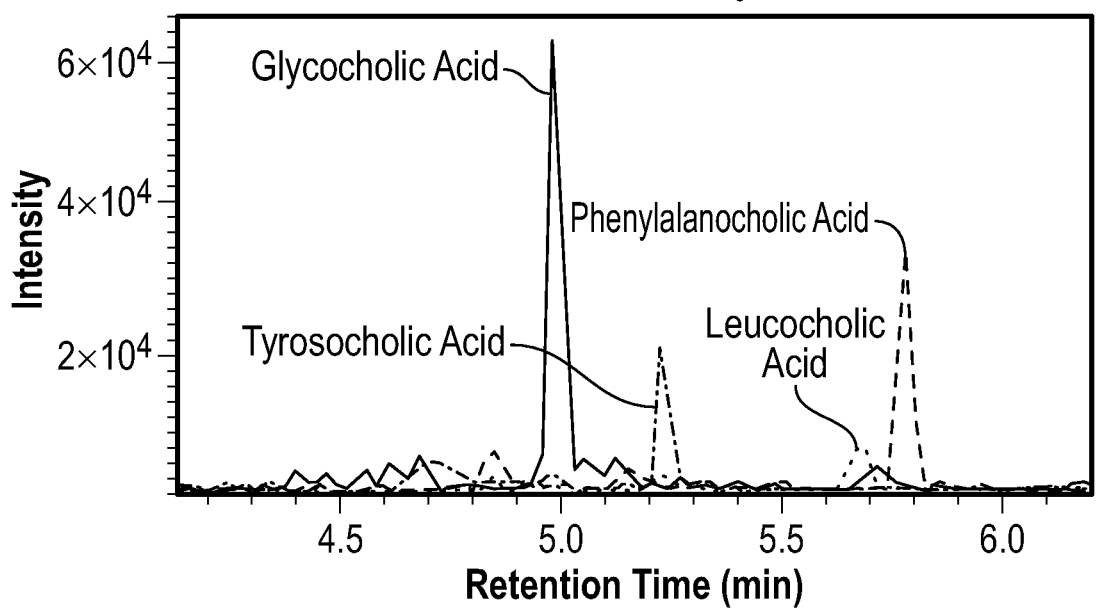
FIGS. 8a-8d show mass spectrometry analysis of novel conjugated bile acids.
Figure 8B:
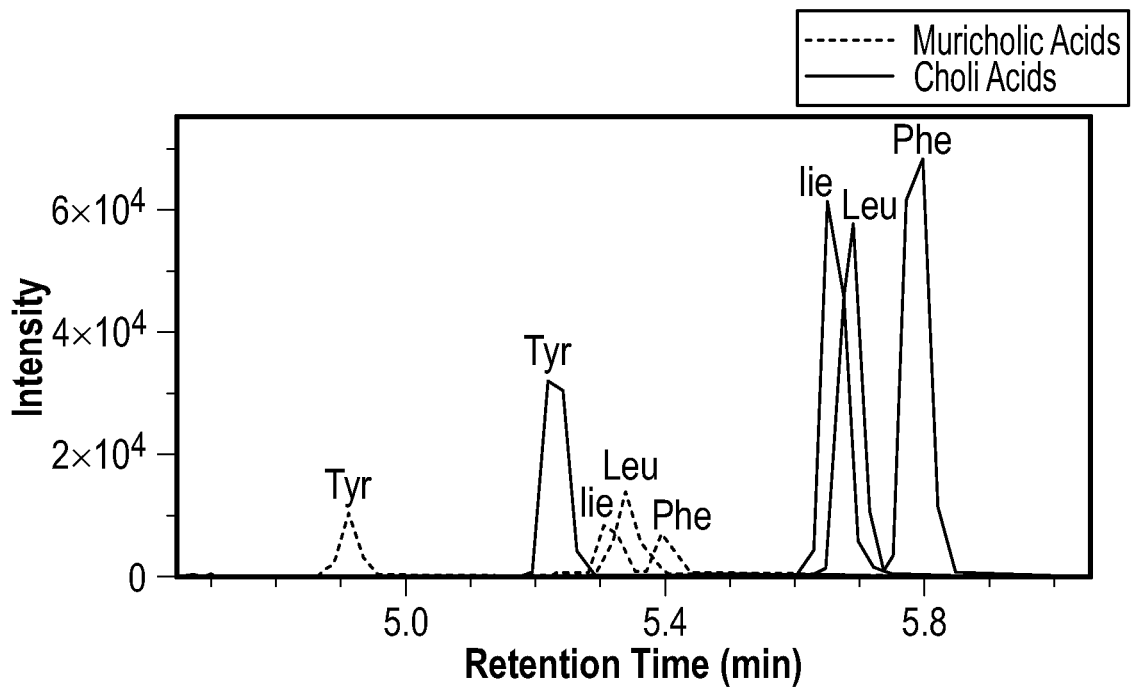
Figure 8C:
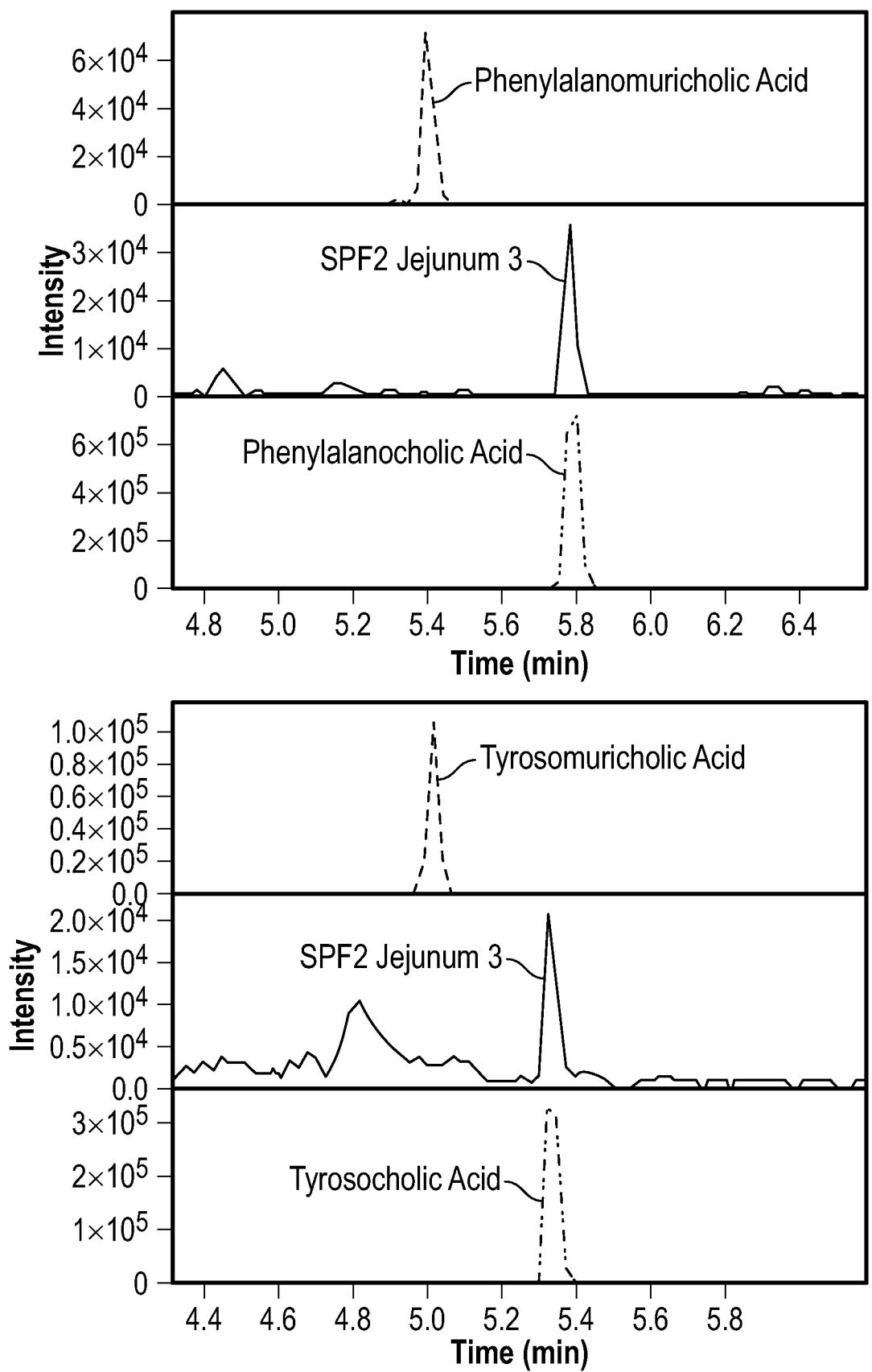
Figure 8C:
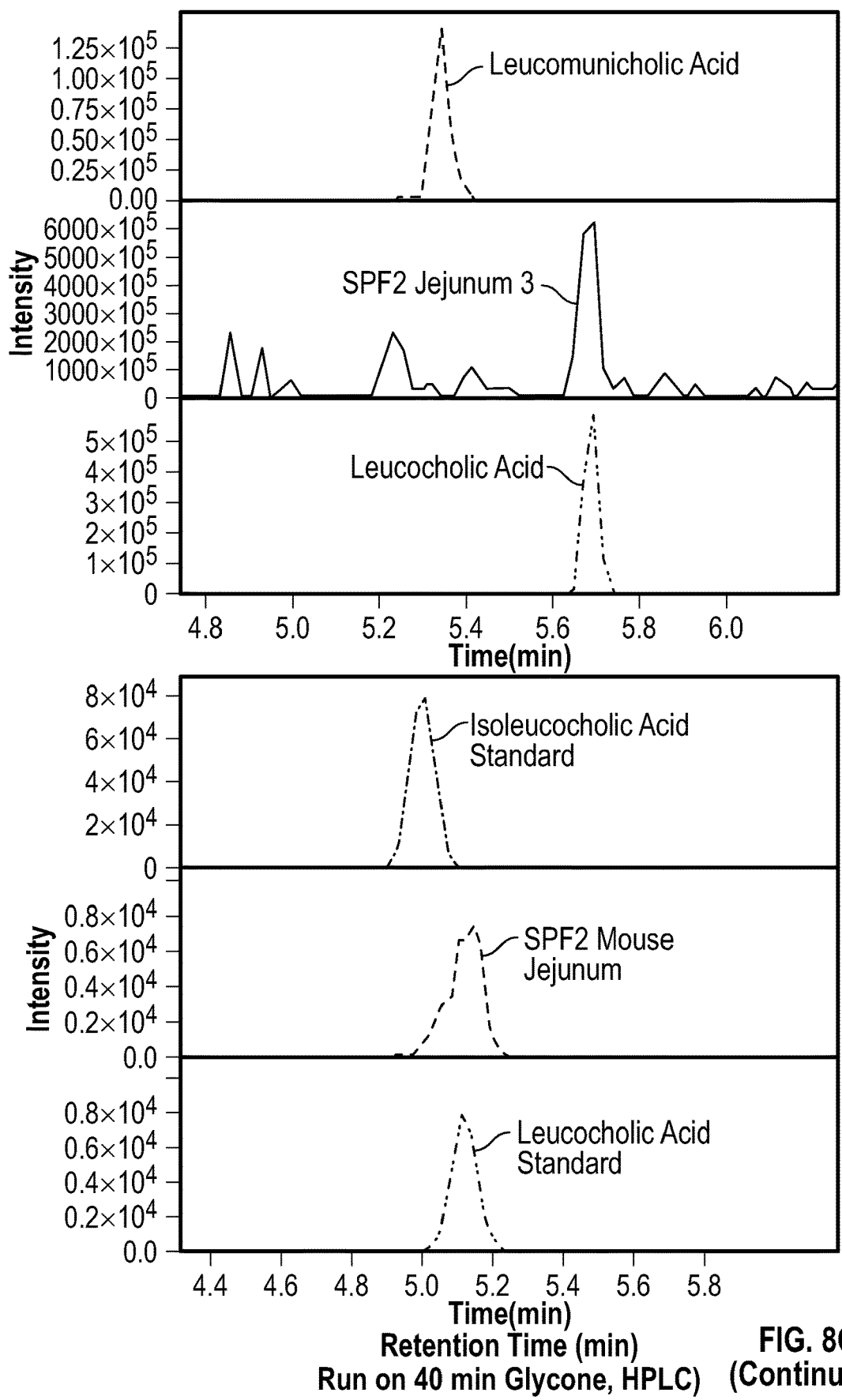
Figure 8D:
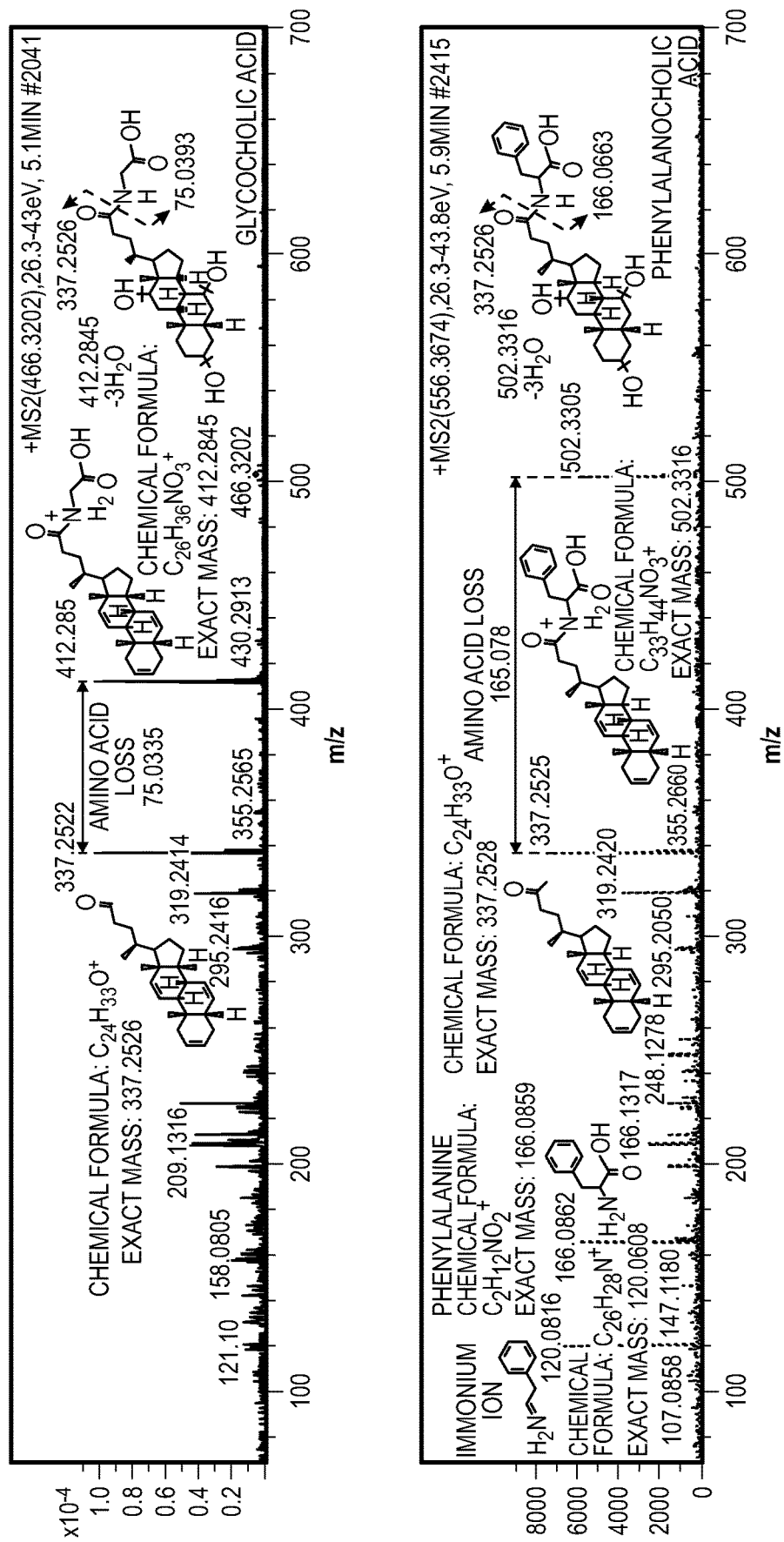
Figure 8D:
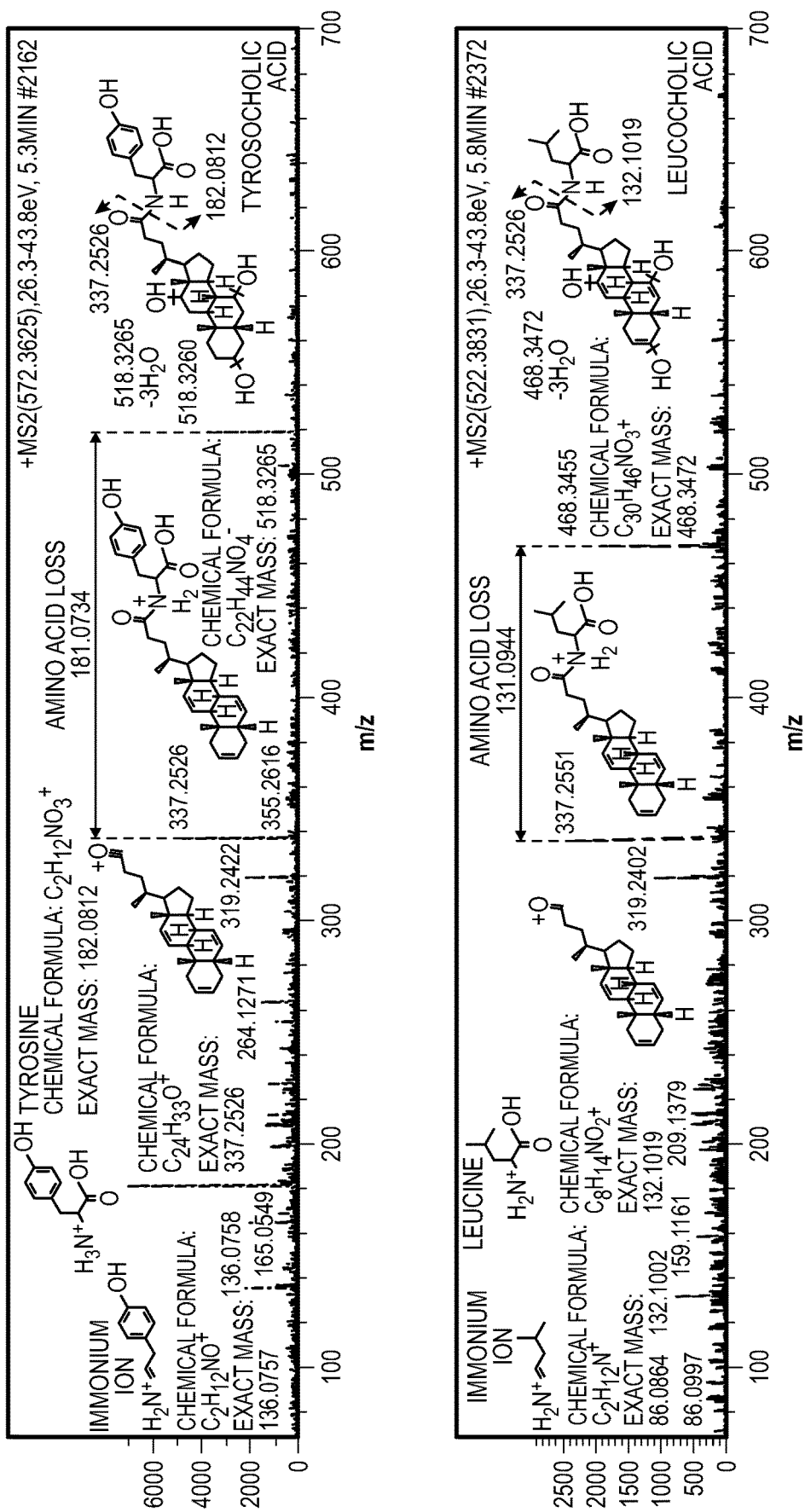

FIGS. 8a-8d. Mass spectrometry analysis of novel conjugated bile acids. FIG. 8a) Extracted ion chromatogram $MS^1$ traces of Tyr-chol (m/z 572.37+/−0.05 Da), Phe-chol (m/z 556.37+/−0.05 Da) and Leu-chol (m/z 522.37+/−0.05 Da, experiments performed four times). FIG. 8b) Extracted ion chromatograms for the synthetic muricholic and cholic acid versions of the Phe-(m/z556.37+/−0.05), Tyr-(572.37+/−0.05) and Leu-(522.37+/−0.05) conjugates showing the different retention times from the muricholic and cholic acid forms. FIG. 8c) Retention time alignments of novel synthetic muricholic and cholic acid conjugates with the novel conjugates found those found in a colonized murine jejunum sample. The isoleucocholic and leucocholic acid analysis was run on a long gradient HPLC column to separate isomeric ile/leu conjugates and compare to that detected in vivo. FIG. 8d) Annotation of MS/MS fragmentation patterns for the 3 novel conjugated bile acids discovered in this manuscript and GCA. Structures of the immonium ions from amino acid fragmentation, whole amino acid fragments and major sterol fragment are shown. Loss of the amino acid mass on the bile acid steroid backbone is also highlighted.

Figure 9A:
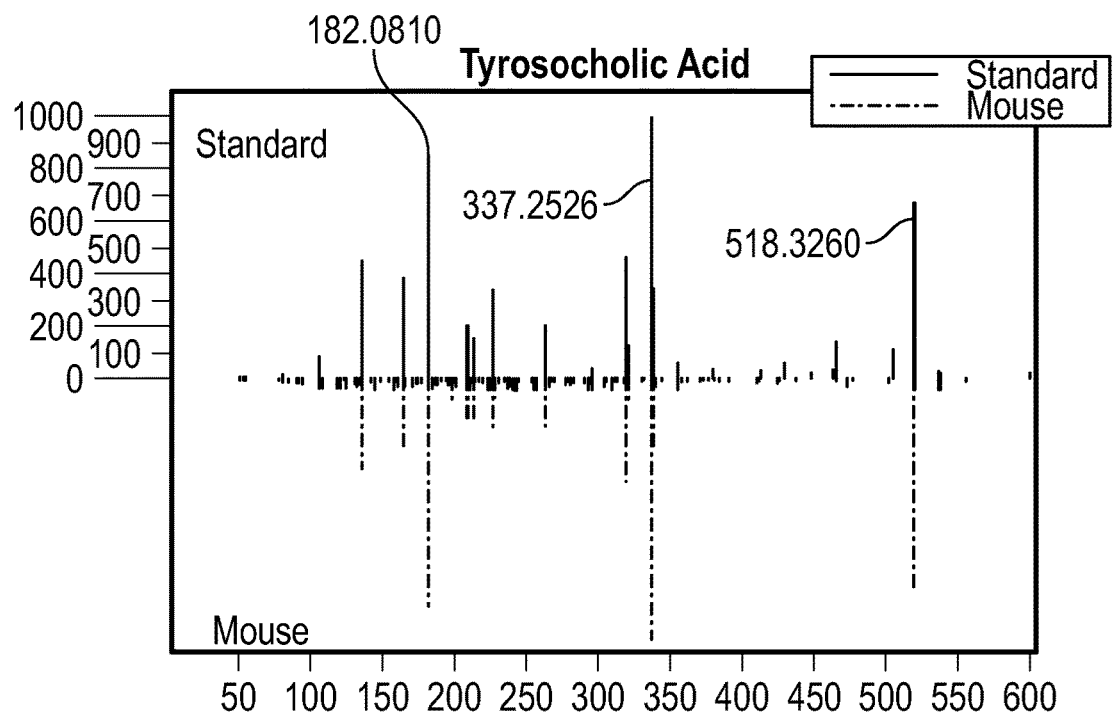
FIGS. 9a-9b show distribution and metabolism of novel conjugated bile acids.
Figure 9A:
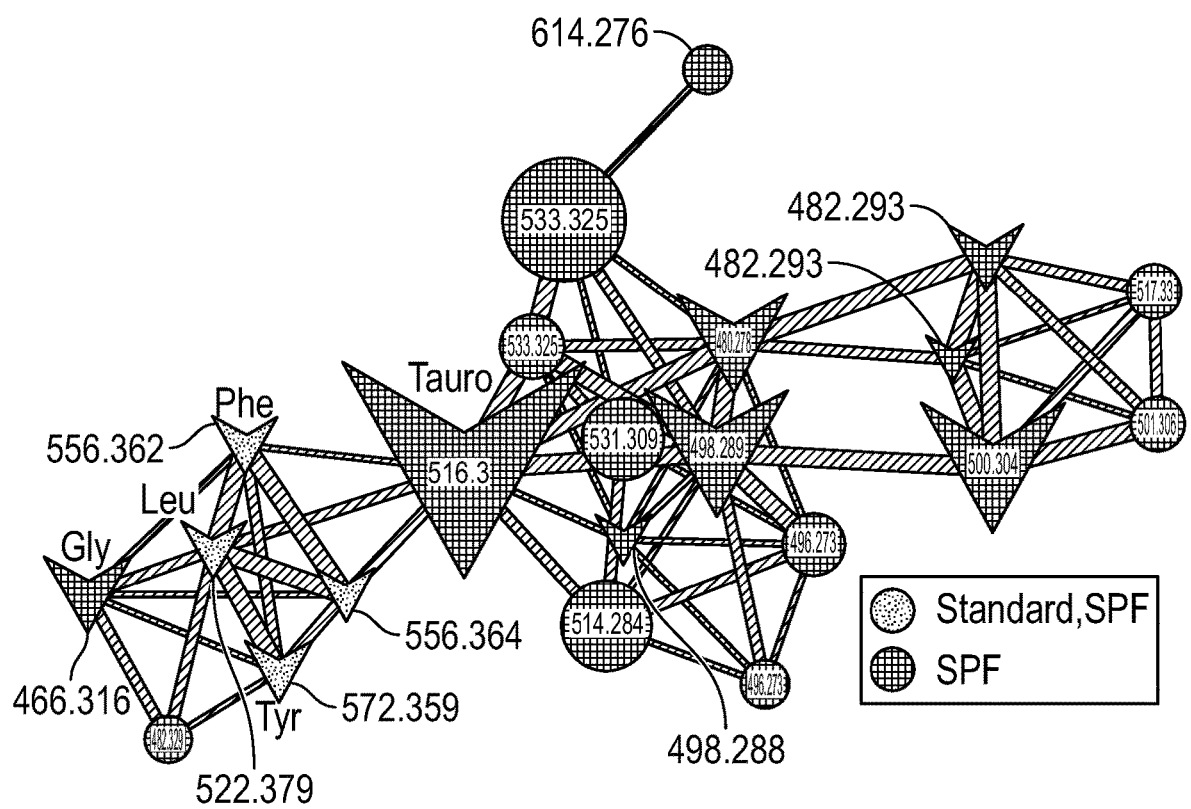
Figure 9A:
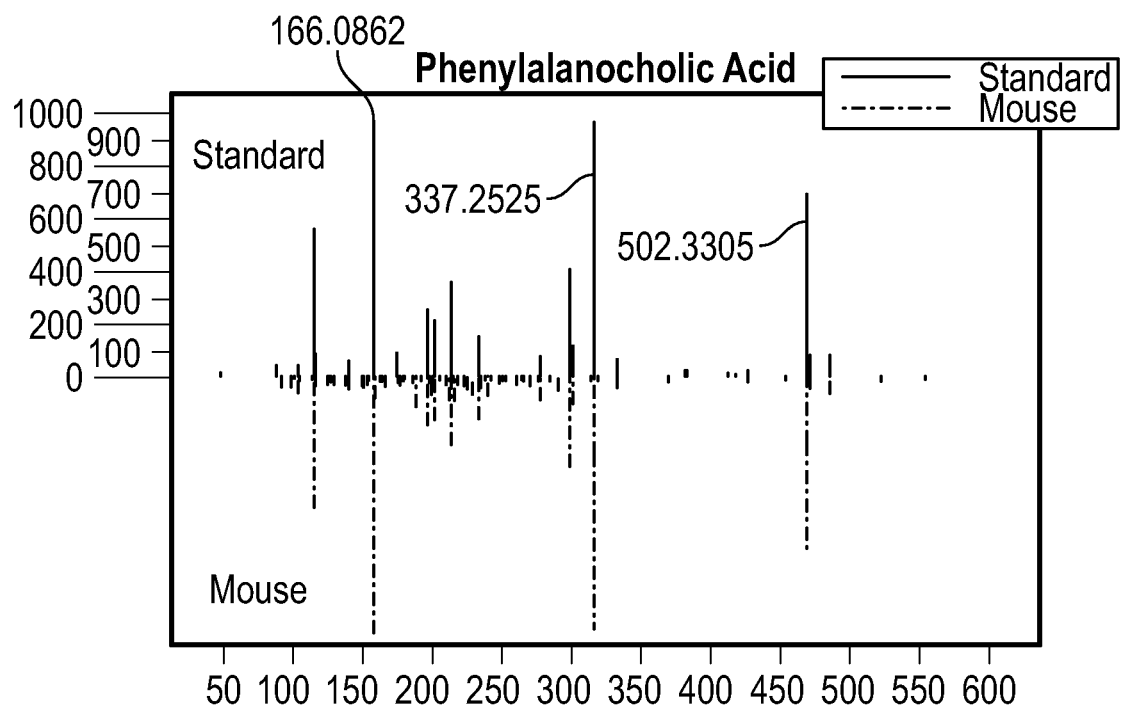
Figure 9A:
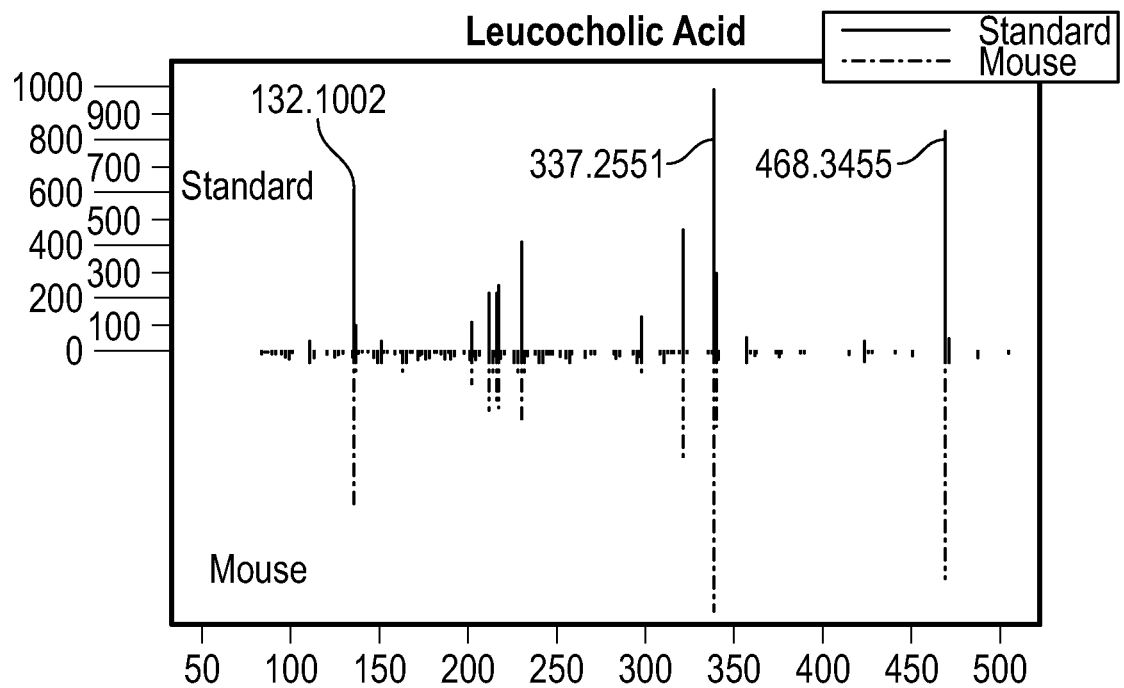
Figure 9B:
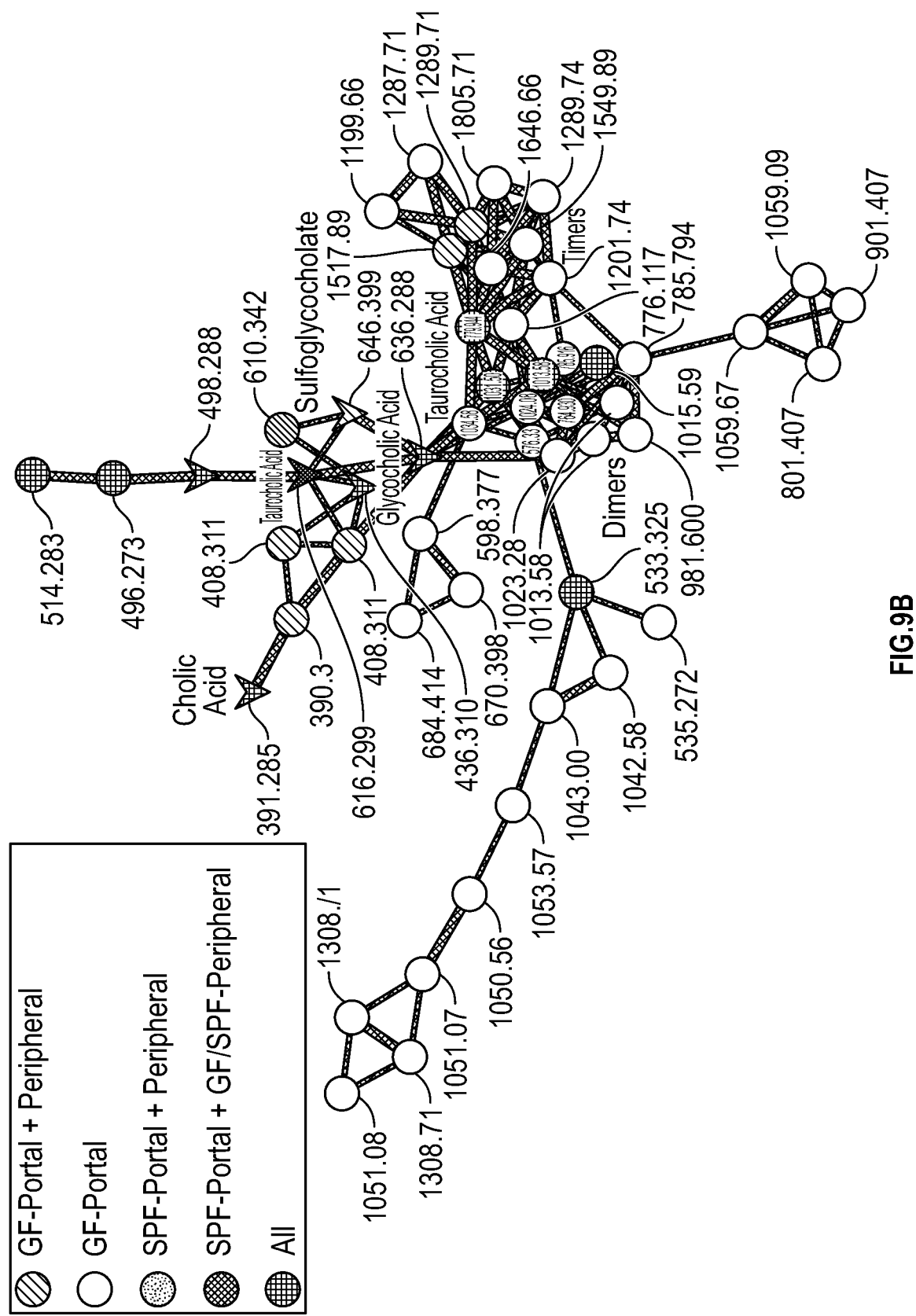

FIGS. 9a-9b. Distribution and metabolism of novel conjugated bile acids. FIG. 9a) Molecular network of SPF duodenum MS/MS data and synthesized amino acid conjugated bile acids. LC-MS/MS data from synthetic standards was networked with murine samples and spectral matching through molecular networking is indicated by node greyscale. Mirror plots showing the alignment between the murine and standards are shown. Nodes shaped as arrowheads had hits in the GNPS libraries and node size is scaled to the spectral count. Tauro=Taurocholic acid. These experiments were repeated twice. FIG. 9b) 3D-molecular cartography of the mean abundance of the newly discovered conjugates mapped onto a 3D-rendered model of the murine GI tract as a heatmap according to the greyscale. Organs are labeled as described in FIG. 1. FIG. 9c) Molecular network of GF and SPF portal and peripheral blood conjugated bile acids. Nodes are colored by source as either GF and SPF or portal/peripheral blood. Arrowhead nodes represent known compounds in the GNPS spectral database, circular nodes represent unknowns. The annotations are through spectral matches against reference libraries (level 2 or $3^3$). FIG. 9d) Mean area under curve abundance and standard deviations of bile acids of interest during incubation with an actively growing batch human fecal culture for 24 h (n=3). FIG. 9e) Molecular network of novel conjugated bile acids after incubation in a human fecal batch culture experiment. Each node represents a unique MS/MS spectrum and arrowhead shaped nodes indicate known spectra in the GNPS database. The nodes are greyscale by their retention time according to the legend and the mass shift between nodes are mapped onto the edge representing the cosine connection between related spectra. The $H_2$ mass shift representing oxidation of the novel conjugates is shown. FIG. 9f) Mean ion intensity and standard deviations of the dehydrogenated forms of Phe-chol, Tyr-chol and Leu-chol through the 24 h batch fecal culture incubation (n=3).

Figure 10A:
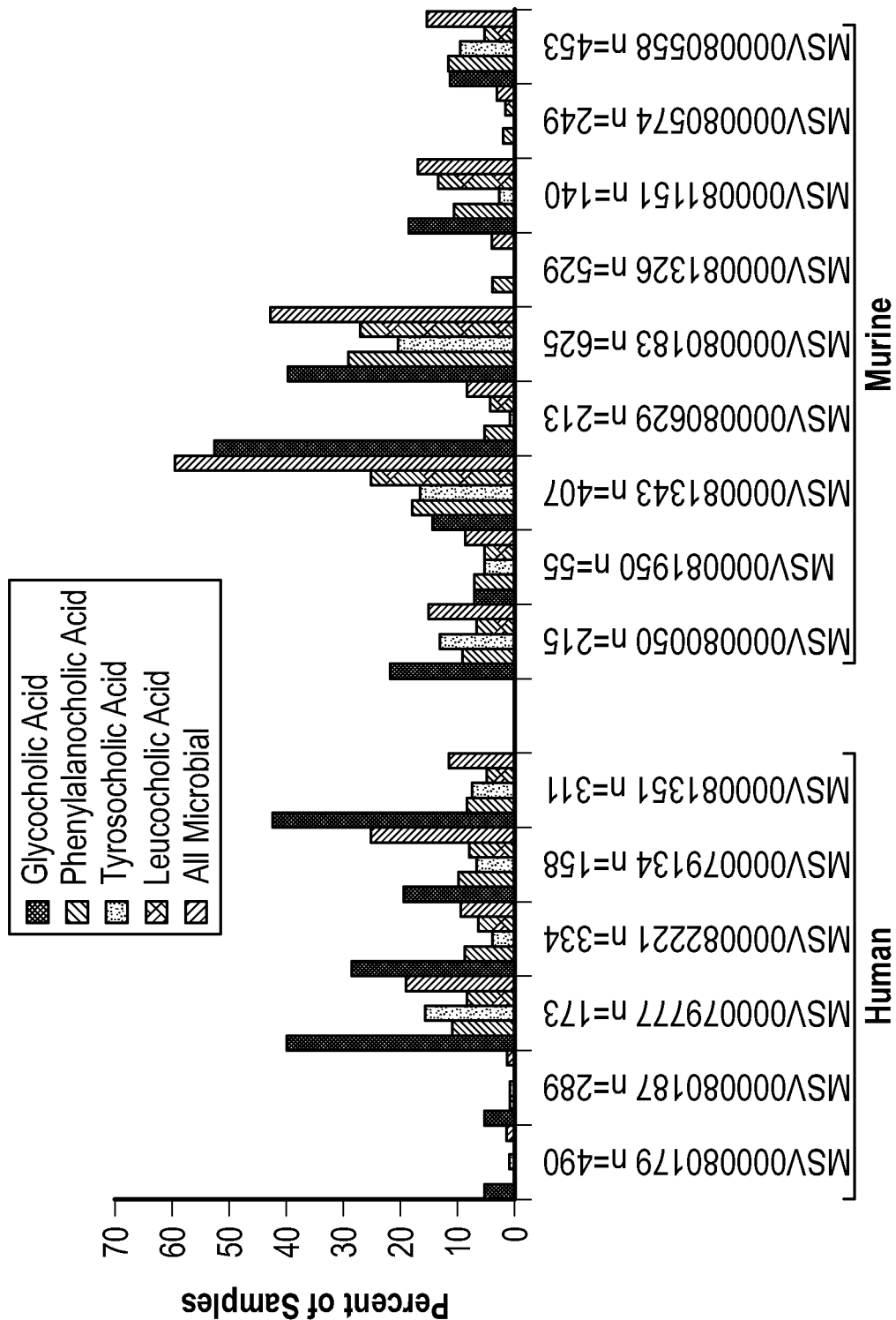
FIGS. 10a-10d show MASST search results and associations of novel conjugated bile acids with high fat diet.
Figure 10B:
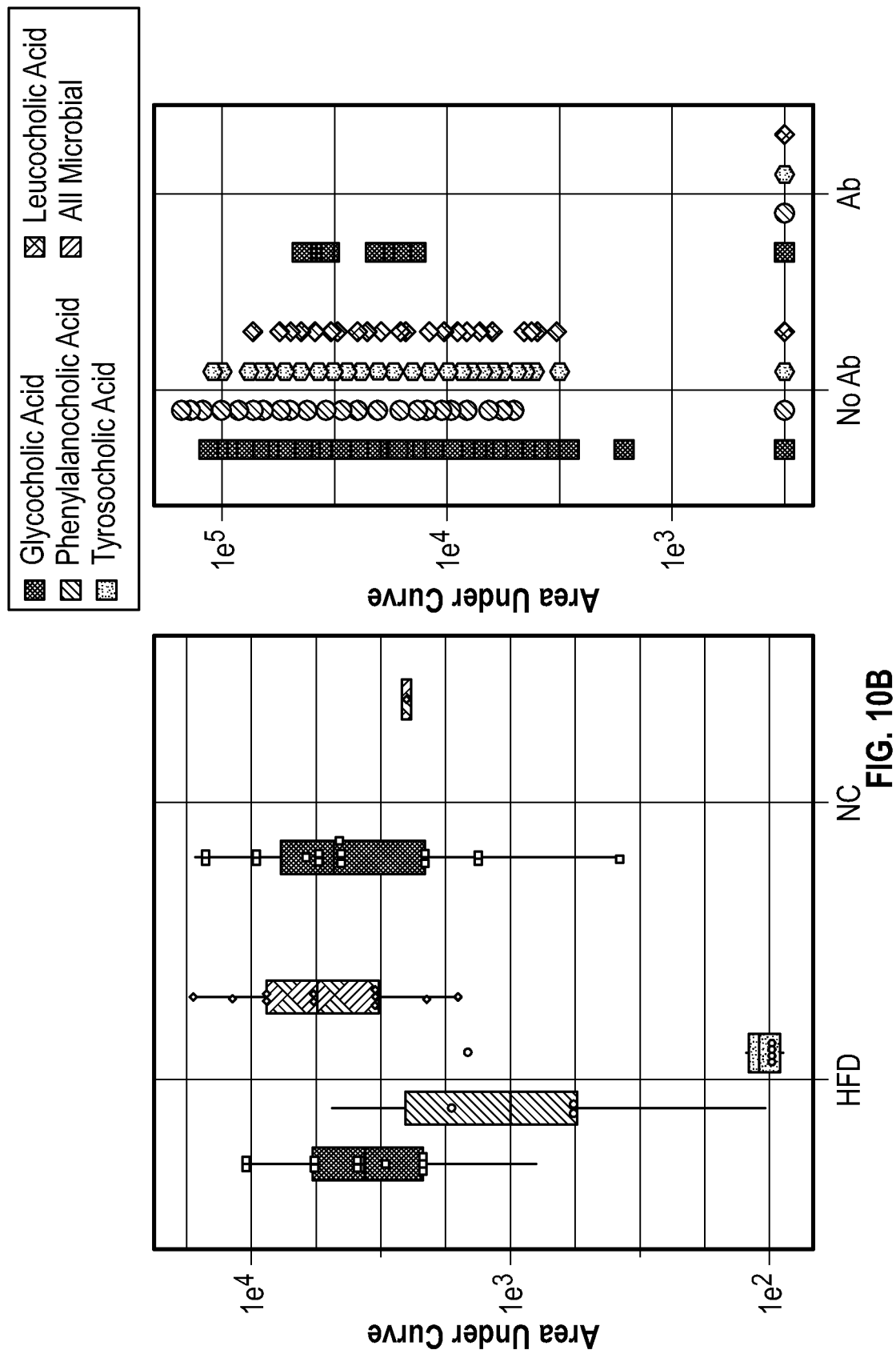
Figure 10C:
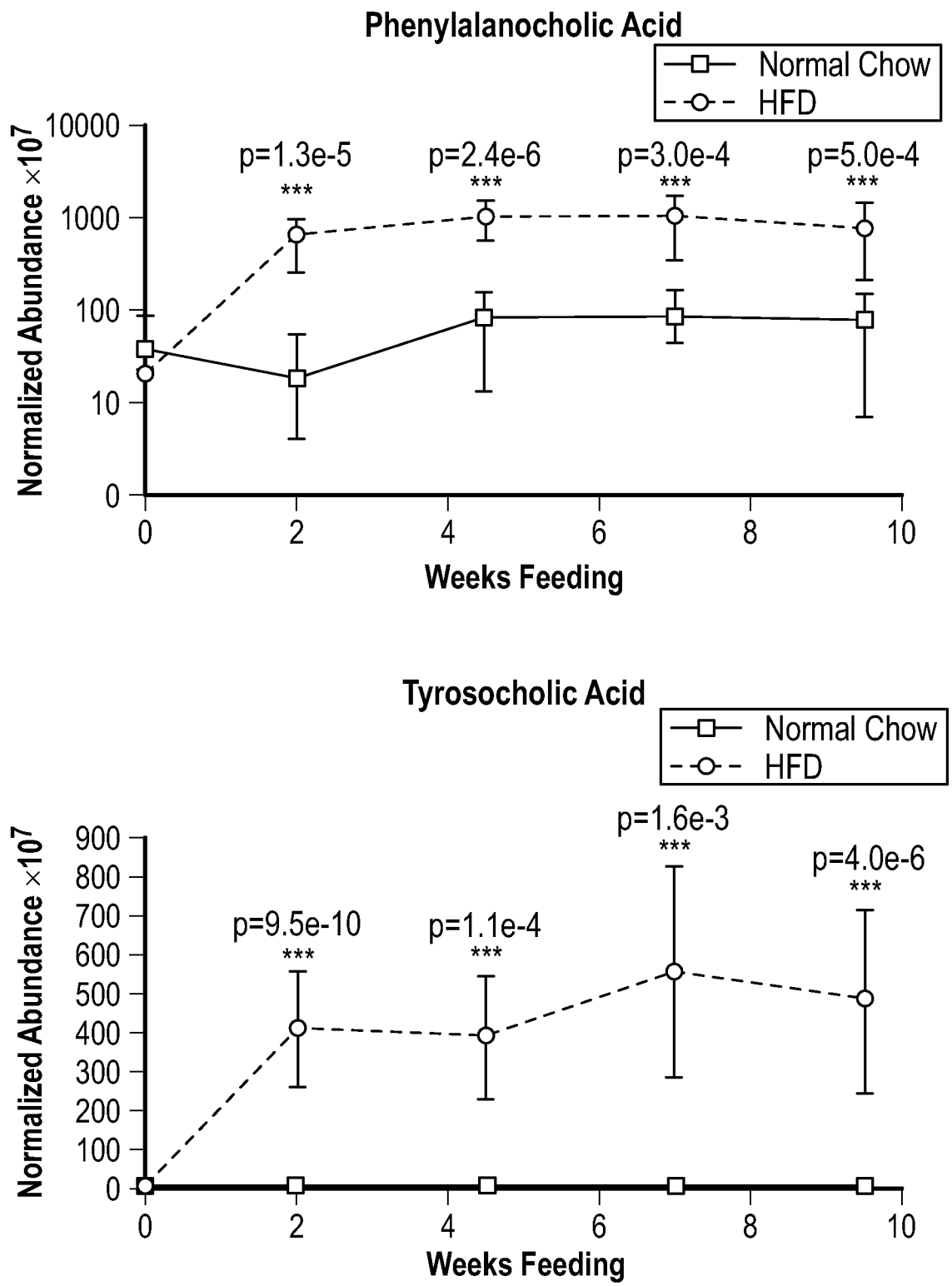
Figure 10C:
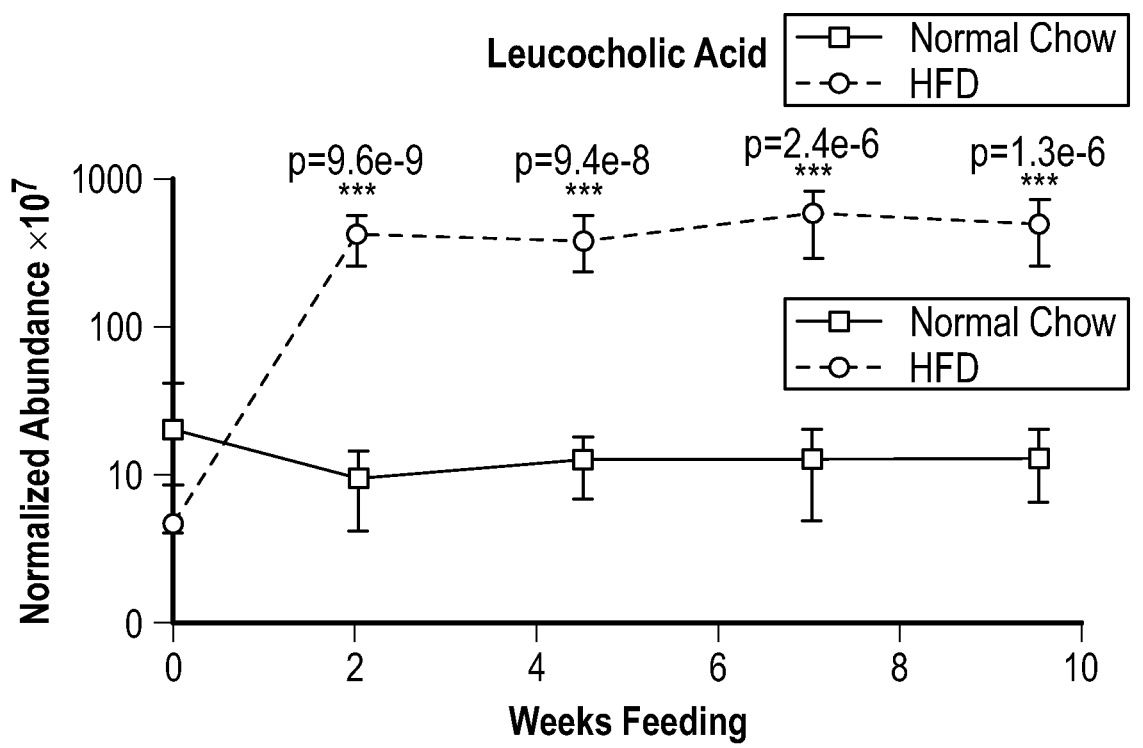
Figure 10C:
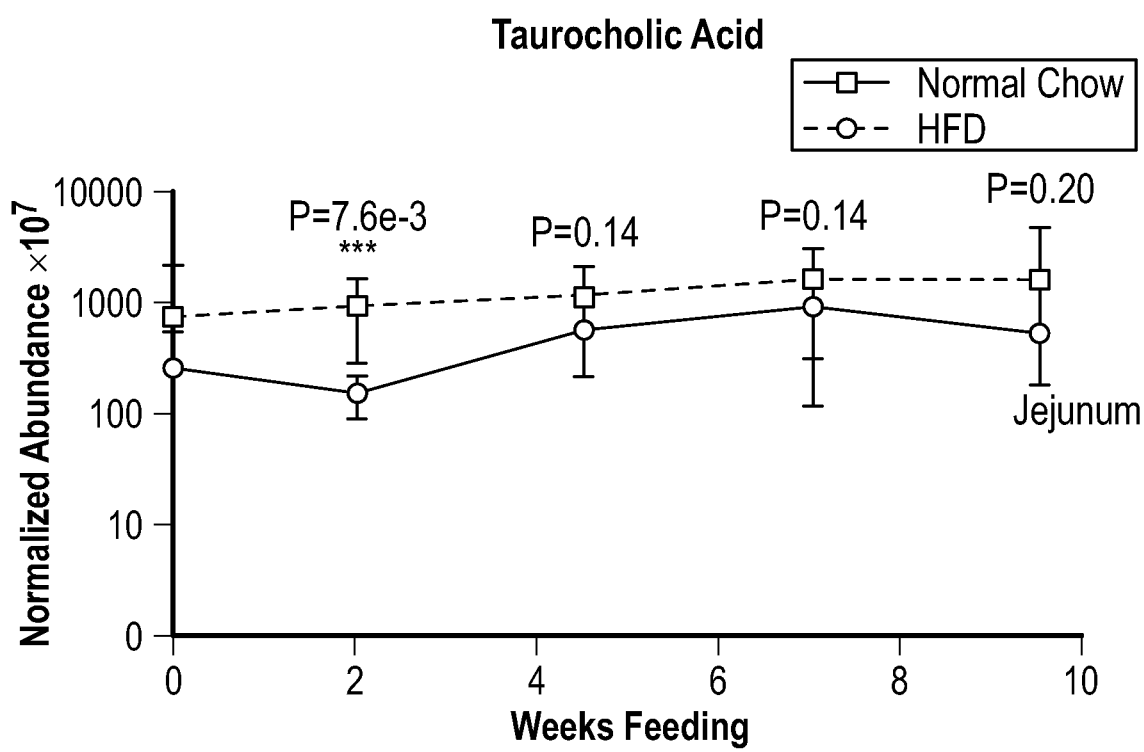
Figure 10D:
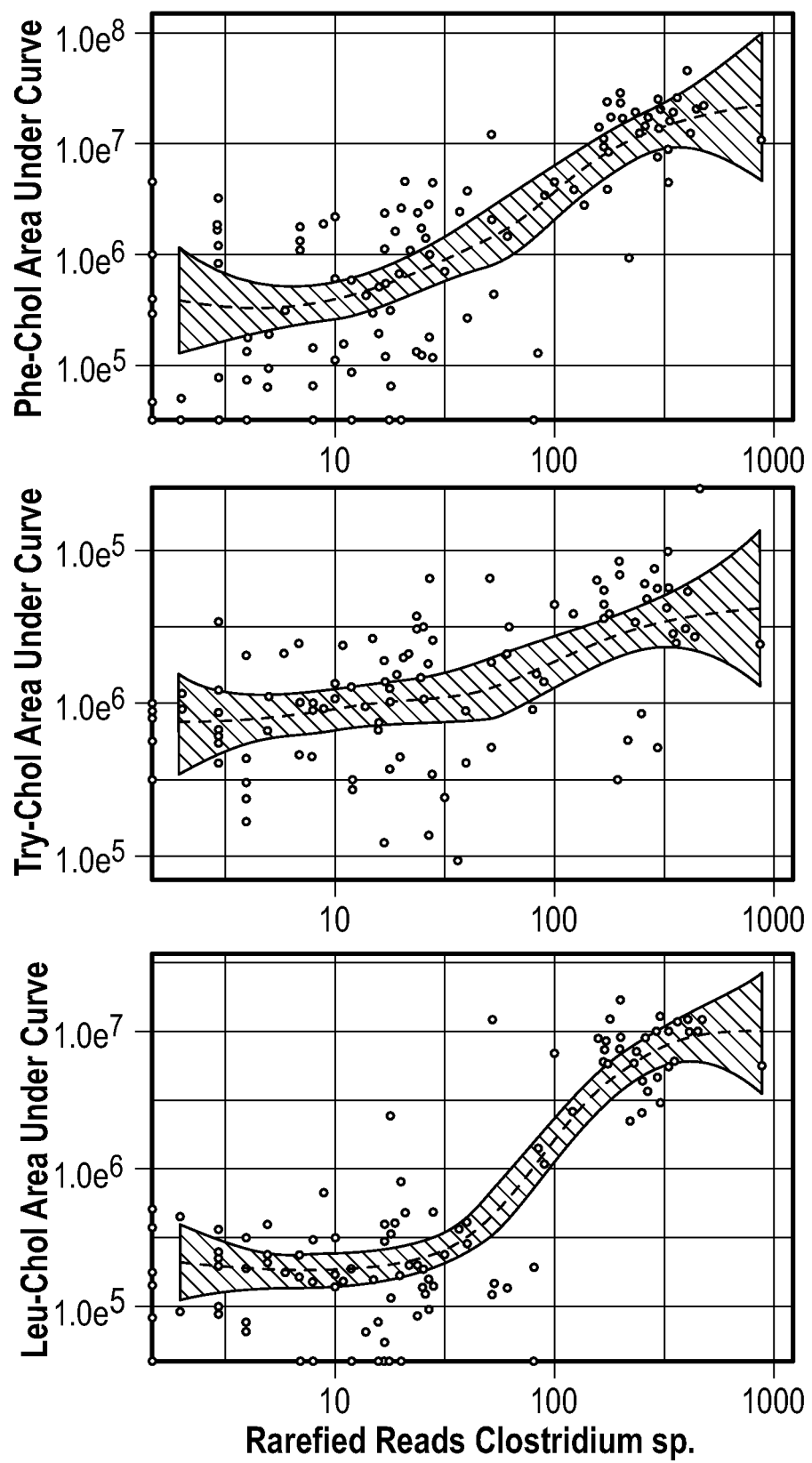

FIGS. 10a-10d. MASST search results and associations of novel conjugated bile acids with high fat diet. FIG. 10a) Proportion of samples where Phe-chol, Tyr-chol and Leu-chol were found from a single spectrum MASST search of publicly available data on GNPS. Massive data set ID's are shown for each dataset and they are divided as either murine or human GI samples. FIG. 10b) Boxplots (boxes represent the interquartile range (IQR), the line is the median, and whiskers are 1.5×the IQR) of the novel conjugates in a previously published murine study where animals were fed high fat diet (HFD, n=14) or normal chow (NC, n=19) (Gly p=0.72, Phe p=0.038, Tyr p=0.083, Leu p=9.4×10$^{-5}$) and dotplot of mice treated with (n=27) or without antibiotics (Ab, n=415)[29]. Bottom greyscale legend corresponds to panels a and b. FIG. 10c) Mean normalized abundance of the three novel conjugated bile acids compared to taurocholic acid in mice (apoE knockout on a C57BL/6J background) fed either HFD (n=12) or normal chow for 10 weeks (n=12). Fecal samples were collected and extracted in 50:50 methanol water and analyzed with LC-MS/MS metabolomics as described in the methods. Standard deviations around the means are shown and significance between HFD and normal chow at each time point is tested with the student's t-test (***=p<0.001, two sided). FIG. 10d) Correlations between rarefied reads of a deblurred read assigned to a *Clostridium* sp. from atherosclerosis mice fed high fat diet through time (n=12). The line of best fit is plotted using the lm method in the R statistical software gray area around the line of best fit is the 95% confidence interval.

Figure 11A:
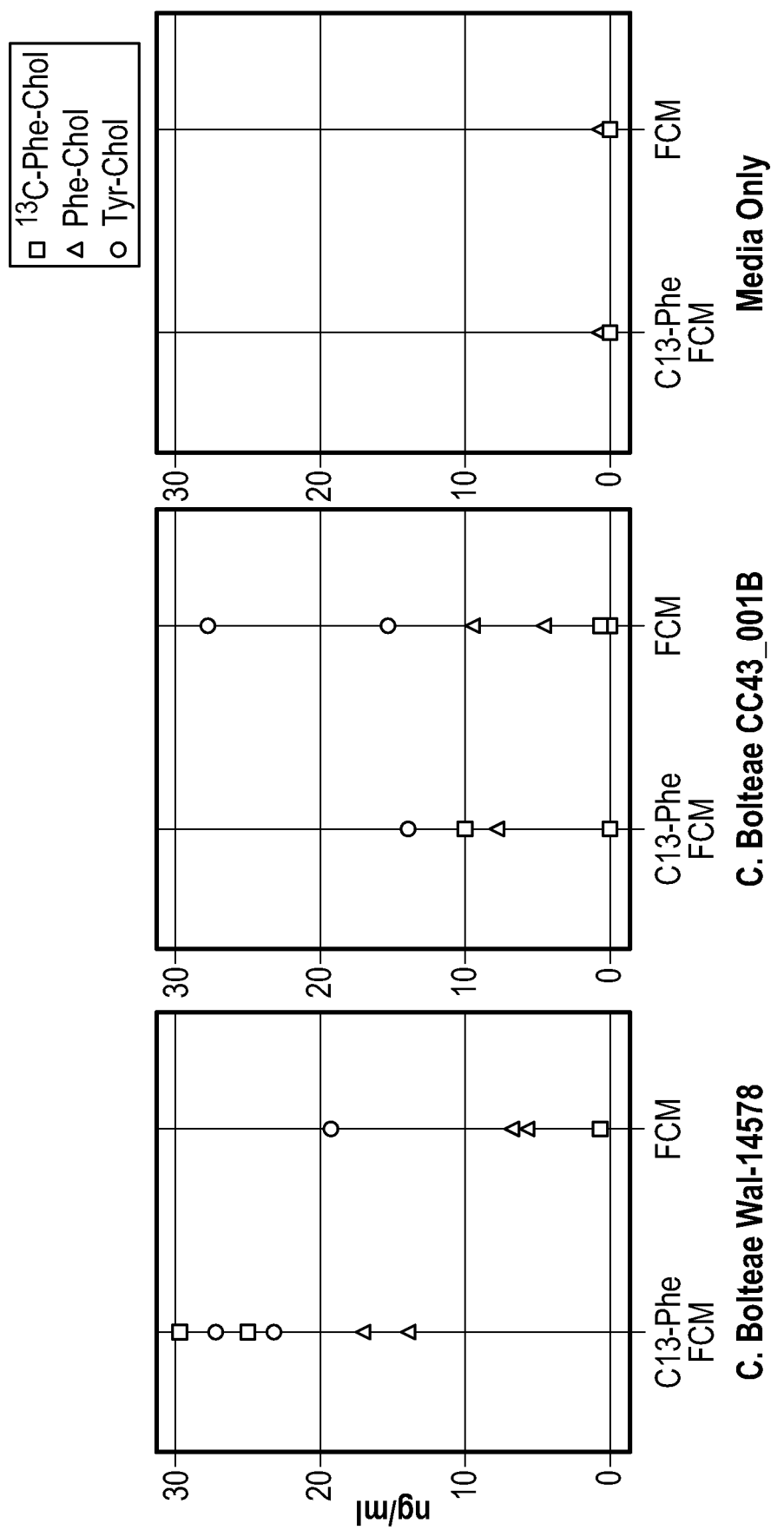
FIGS. 11a-11d show synthesis of novel conjugated bile acids by Clostridia spp.
Figure 11C:
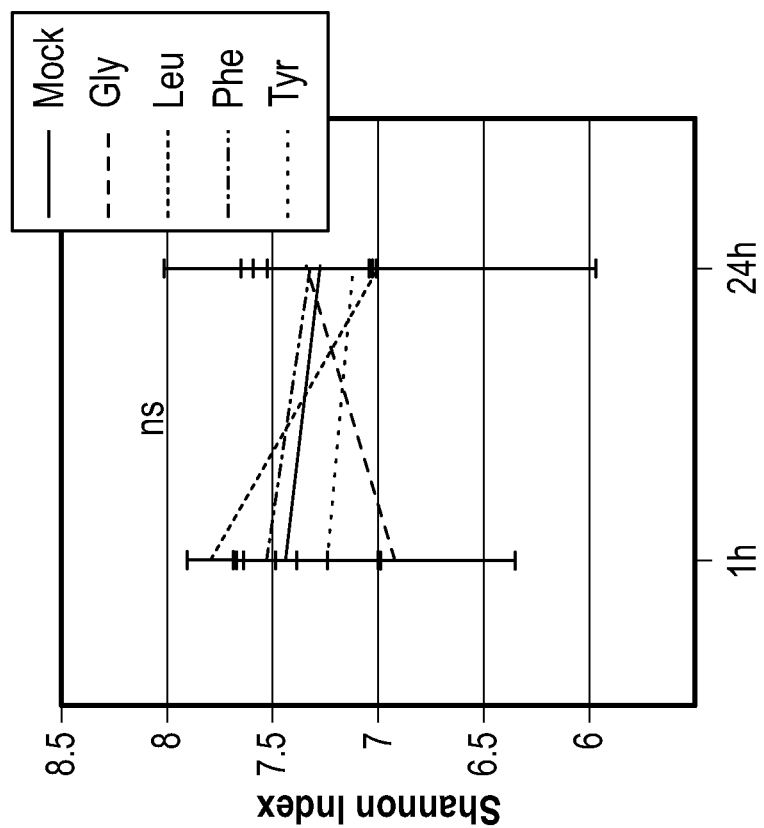
Figure 11B:
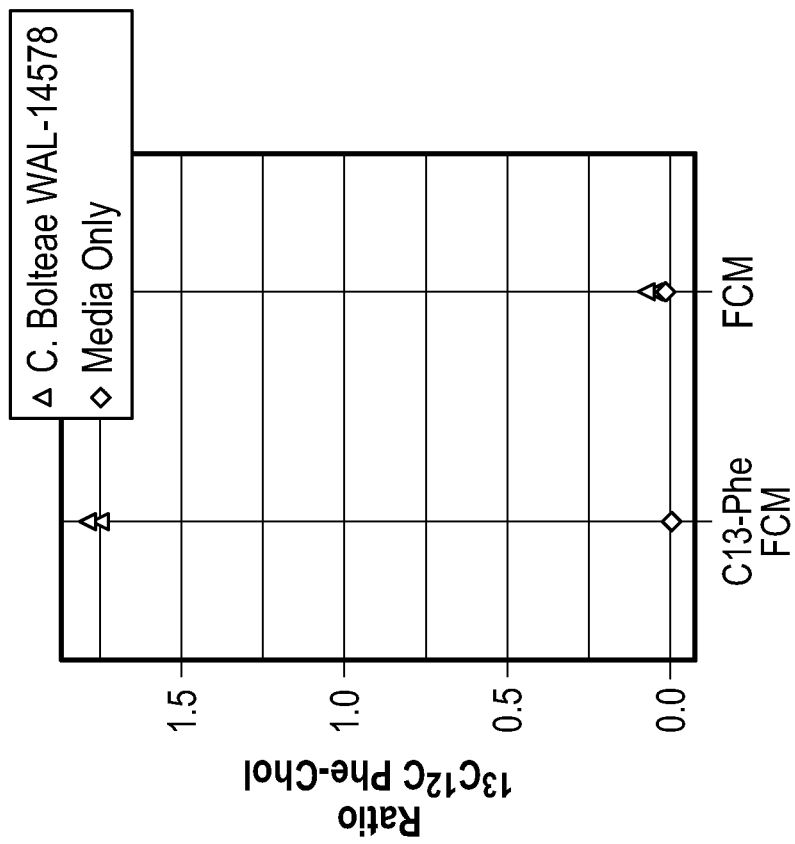
Figure 11D:
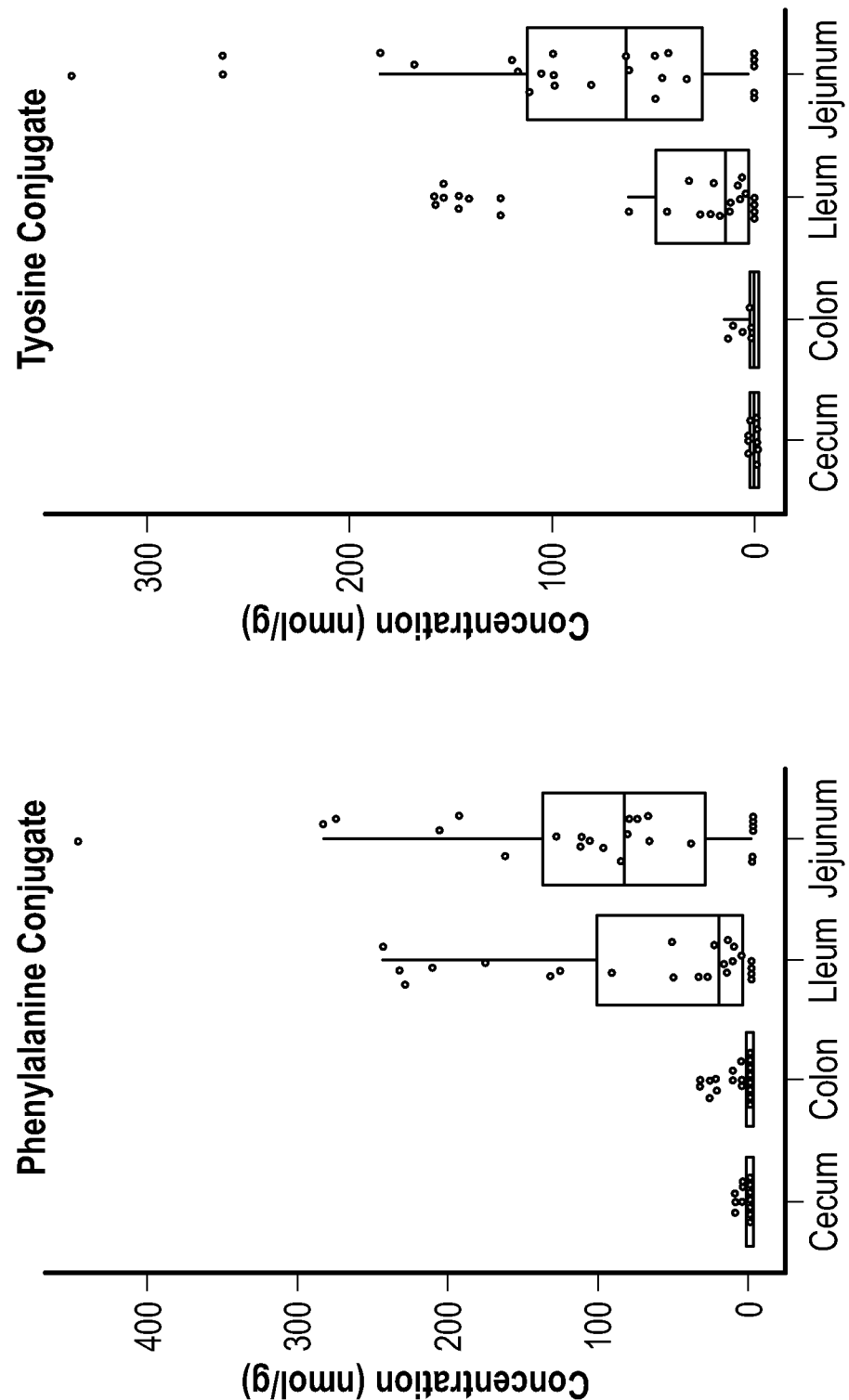

FIGS. 11a-11d. Synthesis of novel conjugated bile acids by *Clostridia* spp. FIG. 11a) Dotplot of the measured production of Phe-chol and Tyr-chol using a targeted LC-MS method for two Clostridium bolteae strains grown in fecal culture media (FCM) with or without labelled Phe (n=2). FIG. 11b) The mean ratio and standard error of $^{13}C:^{12}C$ phenylalanocholic acid from the same C. bolteae strains when grown with fecal culture media (FCM) with $^{13}C$-labelled phenylalanine (bottom left, n=2). FIG. 11c) Mean and standard deviation of the Shannon index of human fecal batch culture (n=3) before and after 24-hour growth exposed to conjugated bile acids or a mock control (NS=not significant by Mann-Whitney U-test). FIG. 11d) Box and whisker plots of concentration of Phe-chol and Tyr-chol in original SPF gut samples. (Boxes represent the IQR, the center is the median, and whiskers are 1.5×the IQR, n=4)

Figures 12A, 12B:
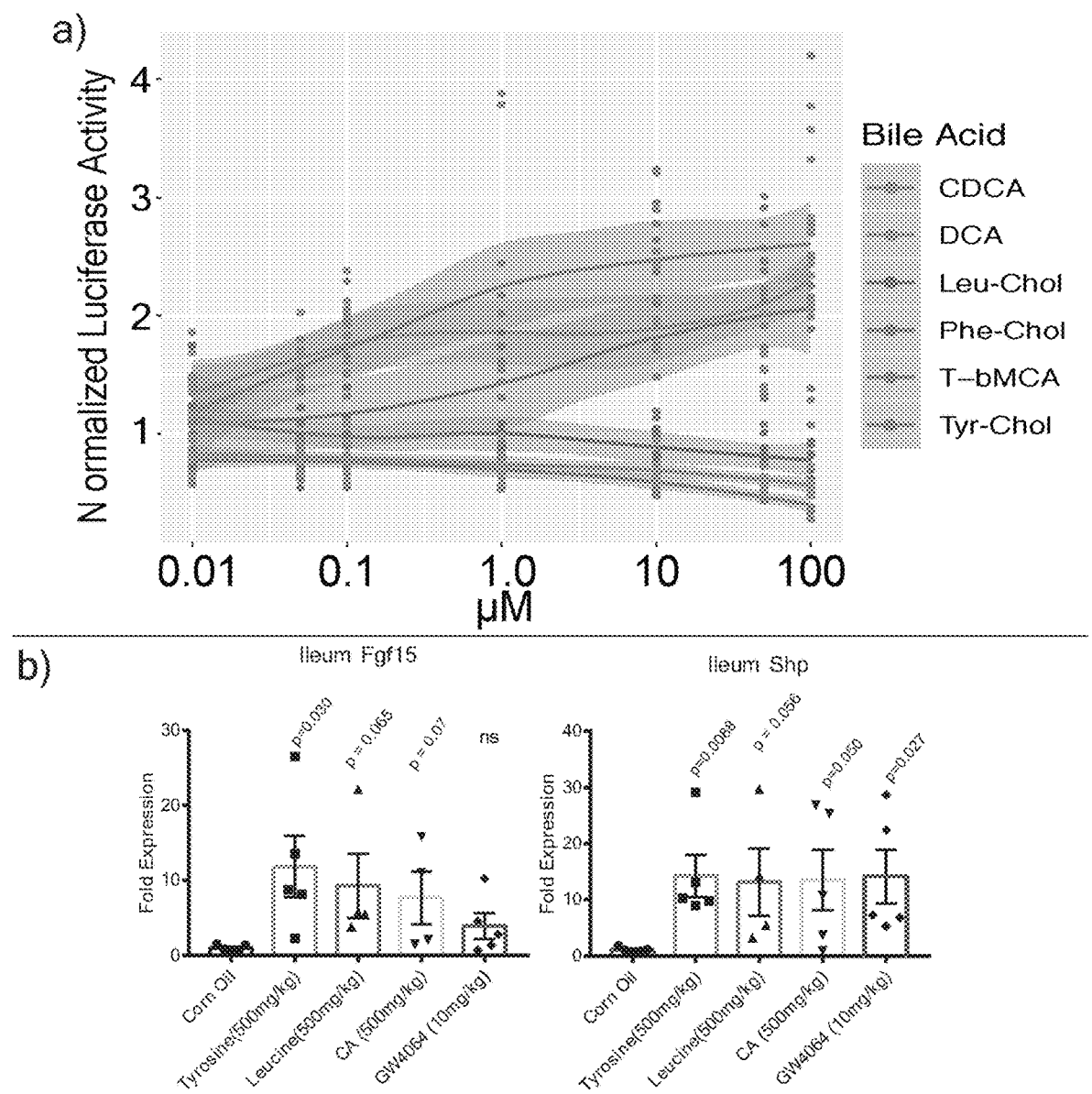
FIGS. 12a-12c show the effect of novel bile acids on FXR.
Figure 12C:
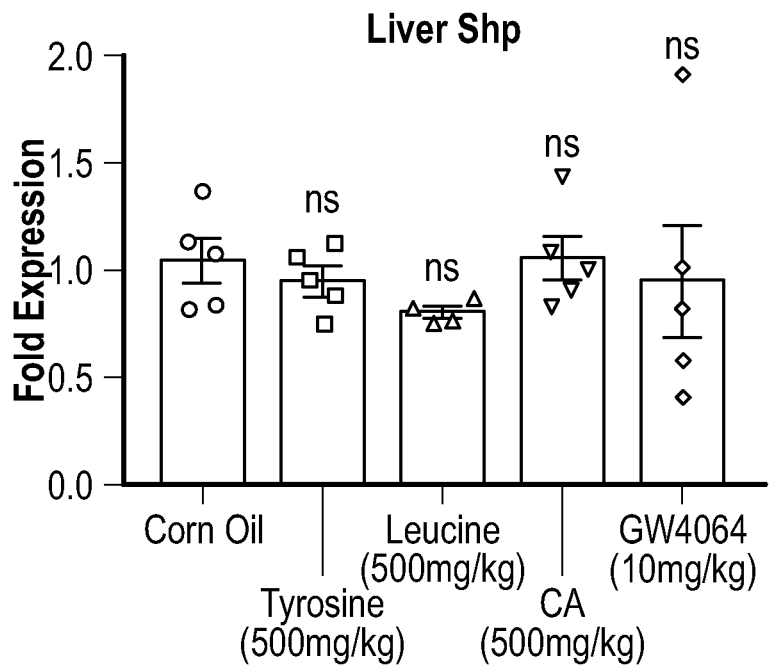
Figure 12C:
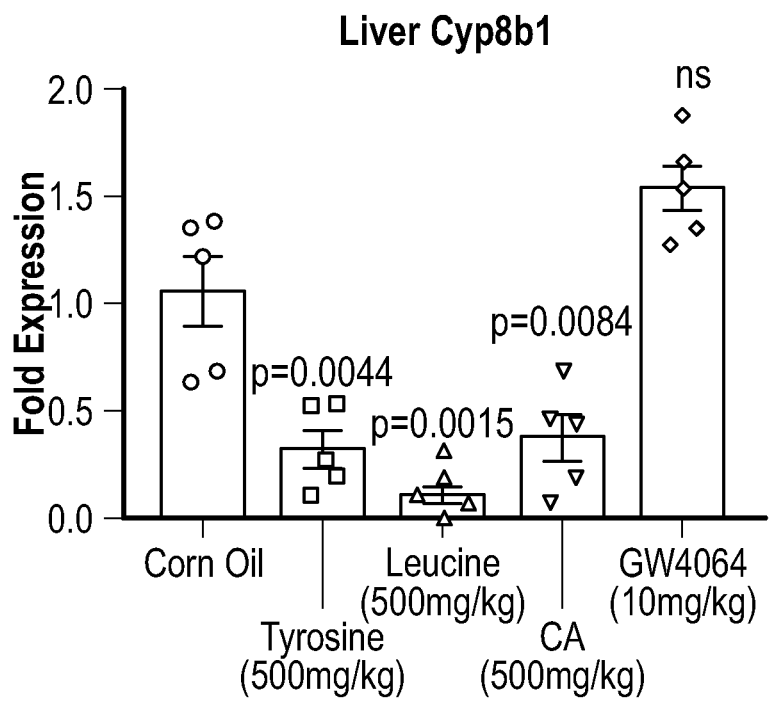
Figure 12C:
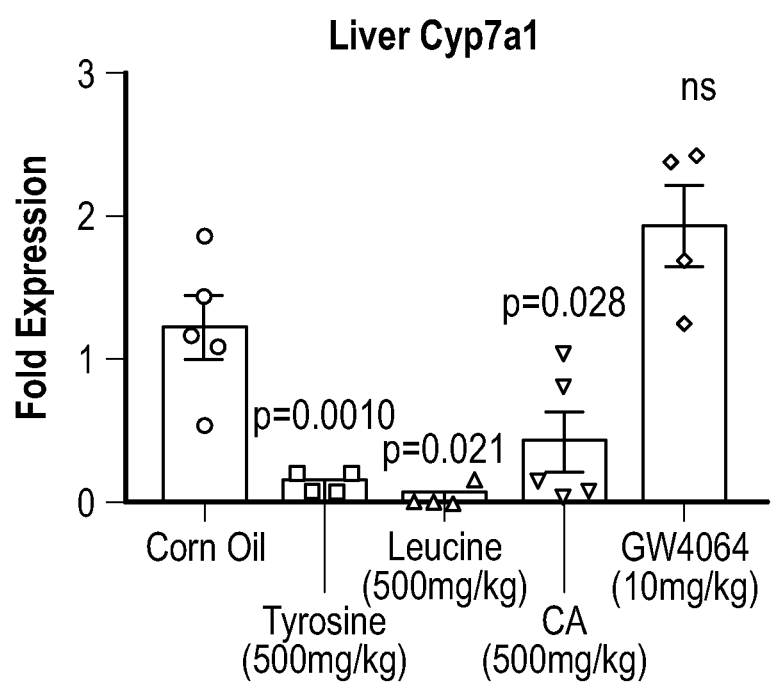

FIGS. 12a-12c. Effect of novel bile acids on FXR. FIG. 12a) Mean normalized luciferase activity as a readout of human FXR stimulation when exposed to various conjugated and unconjugated bile acids as a function of the compound dose (n=8 measurements, +/−SE, DCA=deoxycholic acid, CDCA=chenodeoxycholic acid, T-βMCA=tauro-beta-muricholic acid). FIG. 12b) Ileum mean fold expression change compared to 36B4 control of various bile acids after gavage in mice (error bars are standard error). FIG. 12c) Liver fold expression change compared to 36B4 control of various bile acids after gavage in mice. Significance was tested with the two-tailed t-test compared to the mock corn oil control (error bars are the standard error).

Overall Microbiome and Metabolome Relationships. A broad overview of data relationships was first assessed through principal coordinates analysis (PCoA) using the Bray-Curtis dissimilarity matrix (metabolome) and UniFrac distance (microbiome) (FIG. 4a). The metabolome data was most strongly influenced by organ source (FIGS. 4b-4c). When plotted by organ, four distinct metabolome clusters emerged: the gastrointestinal (GI) tract, epidermal swabs, blood rich organs (lung, heart, spleen, and blood itself), and a cluster of all other visceral organs (FIGS. 4a-4b). We further collected 16S inventories to understand the spatial pattern of bacterial colonization in the mice. As expected, the microbiome data was dictated by colonization status. GF mice and sterile organs in SPF mice clustered tightly with background sequence reads from blanks (reflecting their sterility), whereas colonized organs within the SPF mice clustered apart from these samples (FIGS. 4a-4b). Notable separation of certain organ systems was observed in the microbiome of SPF mice, including a distinct grouping of the GI tract (including the esophagus) and clustering of the vagina and cervix samples (FIGS. 4a-4b). To quantify the effect of microbial colonization on the metabolomic data, the Bray-Curtis dissimilarity was calculated between the $MS^1$ data of GF and SPF mice, then compared to the within group variation for all paired sample locations with statistical significance being determined by Mann-Whitney U-test. The strongest separation between the metabolomic data was present in stool, followed by the cecum, other regions of the GI tract, and samples from the surface of the animals including ears and feet (FIG. 4c). Thus, the major molecular signatures distinguishing colonized and GF mice were present in the gut and epidermis with particularly strong effects in the stool, cecum and ileum. The liver also had signatures suggestive of metabolomic differences between the GF and SPF mice, but this was not significant compared to the within individual variation (FIG. 4c).

The 16S rRNA gene microbiome profiles of the GI tract were dominated by Bacteroidales clade S24-7, Firmicutes, *Lactobacillus* and *Akkermansia muciniphila* (FIG. 4d). Large changes in microbial profiles were observed traversing the GI tract. The esophagus, stomach and duodenum had relatively similar profiles, but a dramatic shift in the jejunum with the expansion of *Lactobacillus* and *A. muciniphila* and a decrease in the relative abundance of Bacteroidales S24-7 was evident. The community transitioned again through the ileum with a further expansion of *Lactobacillus*. At the cecum an abrupt transition was observed with a reduction of *Lactobacillus* and increase in the relative abundance of Firmicutes (FIG. 4d), this community was largely maintained through the colon until the stool, where the Firmicutes were reduced (FIG. 4d).

Unique molecules from the microbiome. Molecular networking paired with statistical analysis enabled identification of molecules unique or enriched between the two groups of mice. These included bile acids, flavonoids, triterpenoid saponins, and urobilins (FIGS. 4-7). The soyasaponins and flavonoids were prevalent, diverse and differentially abundant between the two groups of mice. These compounds were sourced from the mouse chow that had a dominant soybean component. A cluster of 76 connected nodes in the molecular network representing soyasaponins was found in both GF and SPF mice and their food pellets, but these clusters were enriched in nodes from the GI tract of GF mice (FIGS. 5a-5f). This molecular family contained a variety of unique soyasaponins all comprised of the core soyasapogenol triterpenoid backbone, but with different glycosylations and hydroxylations. Soyasaponins were present throughout the GI tract of GF mice, including the stool sample, but in SPF mice they disappeared upon passage into the cecum (FIGS. 5a-5f). Conversely, there was a separate cluster only found in SPF mice that was annotated as soyasapogenols, which represent the triterpenoid backbone of soyasaponin without glycosylation (FIGS. 5a-5f). 3D-molecular cartography showed that soyasaponin I was abundant throughout the GI tract of GF mice, particularly the cecum, colon and stool, but was absent from these organs in SPF animals. In direct contrast, soyasapogenol was not found at all in GF animals, but was detected in the cecum of the SPF mice through to the stool. This differing presence of the glycone and aglycone forms indicates that cecal microbial activity was responsible for the metabolism of soyasaponin into soyasapogenol by removal of the saccharides (FIGS. 5a-5f). The abundance of soyasapogenol E (m/z 457.36) was then regressed against the microbiome data for significant associations between this metabolite and microbial operational taxonomic units (OTUs) (Bonferonni corrected p-value for 195 OTUs $p<2.6\times10^{-4}$). The Firmicute *Allobaculum* sp. (Pearson's r=0.491) was significantly correlated to the abundance of soyasapogenol E; the only cultured representative of this genus contains the β-glucosidase enzyme known to perform deglycosylation of plant natural products.

Microbiome breakdown of plant flavonoids was also observed (FIGS. 6a-6d). In the mouse chow, glucuronides and aglycone flavones and isoflavones were detected, but not their sulfated forms. Because many isomeric forms of flavonoids exist that cannot be differentiated with our MS/MS methods, we focused on molecular changes in the predominant soybean isoflavonoids daidzein, genistein and glycitein, because they have characteristic MS/MS signatures. In the GF mice, 3D-molecular cartography showed that the glucuronidated and sulfated isoflavonoids were detected throughout the GI tract from the stomach through to the stool, indicating they pass through the GI tract intact. In SPF mice, however, these same glucuronides and sulfides were undetectable in the distal GI tract. The aglycones were present in both the GF and SPF mice, but more abundant in the distal GI tract of GF animals (FIGS. 6a-6d, Mann-Whitney U-test, p<0.05). Because the aglycones were detected in both groups, host and microbial enzymes (or chemical processes) could have been responsible for the deglycosylation; however, the complete removal of the sugars and sulfates in the SPF mice indicated that the microbiota significantly enhanced this process. Furthermore, in the cecum of the SPF mice, the aglycone isoflavonoids were depleted and in some cases no longer detectable through to the stool samples, indicating that further metabolism of these compounds was occurring in the cecum and colon due to the presence of bacteria.

The production of secondary bile acids was also prevalent in SPF mice, but not GF mice. Deoxy- and keto-forms (dehydrogenated) of cholic acid were abundant in the distal GI tract of SPF mice but absent from GF mice (FIGS. 7a-7b). In contrast, the primary bile acid tauromuricholic acid was abundant throughout the gut of GF mice but was depleted in the distal GI tract of SPF mice. Muricholic acid was also exclusive to the guts of SPF mice but was found in the liver of sterile animals (FIGS. 7a-7b).

MS/MS Annotation of Novel Conjugated Bile Acids. Analysis of the unique nodes in SPF mice related to glycocholic acid (FIG. 2a) led to the discovery of the unique conjugation with different amino acids. The major core fragment of cholic acid in all conjugated bile acids is shown in FIG. 8d at mass m/z 337.25. This represents the core steroid backbone of cholic acid with loss of the amino acid conjugate and all hydroxyl groups. In the new Tyr, Phe and Leu conjugates the difference in mass of a whole amino acid can be seen from the parent ion and this fragment. Furthermore, this amino acid ion appears in the lower m/z range of the spectrum as the whole amino acid plus a hydrogen ion ($H^+$). Further verification of these molecules comes from the presence of unique immonium ions, a characteristic of peptide fragmentation, which are seen in the lower mass range corresponding to each of the three amino acids (FIG. 8d, Table 1).

Amino Acid Conjugate Synthesis and Validation. Both cholic and muricholic forms of the three novel amino acid conjugates and an isoleucine conjugate were chemically synthesized and verified using nuclear magnetic resonance spectroscopy (NMR spectra below). Polarity and MS/MS fragmentation patters of these compounds were subsequently analyzed and the higher hydrophilicity of muricholic acid forms were validated by earlier retention times for all four synthesized compounds (FIGS. 8b-8c). MS/MS patters of muricholic and cholic acid forms were identical and the spectra from the SPF mouse duodenum were subsequently verified to match these synthetic compounds by molecular networking, retention time analysis and MS/MS matching (FIG. 8d). In the mouse jejunum sample the extracted ion chromatogram for leucocholic acid (m/z 522.3700) contained a single peak that most closely matched leucocholic acid, however, there was a small shoulder on this peak indicating that it cannot be ruled out that some isoleucocholic acid may be present (FIG. 8c). MS/MS patters of synthetic standards and novel bile acids from mouse gut samples showed high similarity (FIG. 9a)

Bile Acids in Murine Portal and Peripheral Blood. An additional 4 SPF and 6 GF female mice of the same strain analyzed for the initial study on the microbial metabolome were raised for analysis of blood. Portal blood and peripheral blood were sampled as described in the methods section and analyzed with the same LC-MS/MS protocols as the original animals. Parent masses for the Phe, Tyr and Leu conjugated microbial bile acids that were searched for in the GNPS molecular network were not found (FIG. 9c). The conjugated bile acid molecular family was further inspected for the presence of these compounds but was also negative for the presence of the novel conjugates in either peripheral or portal blood samples from either mouse group. The host conjugated taurocholic acid and glycocholic acid were however, found in both blood types of both murine groups.

Synthesis of Novel Conjugate Bile Acids by *Clostridium bolteae*. After finding a strong association between all three novel conjugates and a *Clostridium* sp. in mice fed high fat diet[25] (FIG. 10), twenty isolates of human gut bacteria were cultured in fecal culture media and screened for the production of these compounds using the same extraction and LC-MS/MS methods described for the mouse organ analyses. Using GNPS integrated with mzMine feature finding, Phe-chol was detected in the extracts from three separate *Clostridium* strains, but at very low intensity. Only *C. bolteae* had produced the molecule clearly at a level at least 3× the abundance of the background extracted ion chromatogram trace. Thus, using the more sensitive targeted and quantitative assay we subsequently repeated these experiments with two isolates of *C. bolteae* and validated the production of both Phe-chol and Tyr-chol in the culture extracts (FIG. 11). More of the tyrosine conjugate was made than (~20 ng/ml) the phenylalanine conjugate (~7 ng/ml). Further validation was provided using media supplemented with $^{13}C$ labeled phenylalanine added to the media. This labeled amino acid was incorporated into the Phe-chol produced by C. bolteae WAL-14578 demonstrating that free amino acids from the media can be used for the conjugation and providing direct evidence that these bile acids are made by microbes (FIGS. 3a-3e, FIGS. 11a-11d).

Detection of Novel Bile Acid Conjugates in HMP2 dataset. Phe-chol, Leu-chol and Tyr-chol were detected in the HMP2 dataset with negative ion mode (Table 6). The statistical testing for differences between inflammatory bowel disease patients in HMP2 are as follows: IBD patients (FIG. 3c, PRISM dataset, FDR-corrected p-value (q-value) from Wald's test of linear effects model of Leu=0.03, Tyr=0.0074 and Phe=0.004, control non-IBD n=34, CD n=68, and UC n=53). Furthermore, they were enriched in CD dysbiosis (HMP2 dataset q-value, Phe=0.0003, Tyr=0.007, Leu=9.0×10$^{-5}$, n=48 CD-dysbiotic, n=169 CD non-dysbiotic) but not statistically different in UC dysbiosis (q=1.0, 0.8, 0.9 for Phe, Tyr, Leu-cholate amidates, n=12 UC dysbiotic, n=110 UC-non-dysbiotic) and not in non-IBD (q=0.4, 0.5, 0.5 for Phe, Tyr, Leu-cholate amidates, n=15 non-IBD-dysbiotic, n=107 non-IBD-non-dysbiotic, Wald's test).

Sequencing of Fecal Cultures Exposed to Novel Bile Acid Conjugates. In the batch culture experiment where an actively growing fecal culture was exposed to the novel conjugated bile acids and other control molecules, the microbiome of the culture media was sequenced using 16S rRNA amplicon sequencing after 24 hours. The data was processed with the Qiita pipeline and the resultant cultures were analyzed for changes in the microbiome structure due to conjugated bile acid exposure. There was no change in the microbiome alpha-diversity when cultured in the presence of any bile acids added to the media compared to the mock control. The Shannon diversity of the community decreased over time, but this was not different than the mock control with no bile acids added (FIG. 11c).

Quantification of Bile Acids. The concentration of the new bile acids in the mouse gut samples was quantified in negative-mode using the targeted method by comparison to the standard curves measured of each molecule in the various tissue samples spiked into the GF mice samples. The calculation was then normalized to the initial g/tissue collected and the dilution through extraction and mass spectrometry analysis (Table 2, FIGS. 11a-11d).

Matrix Effects on Novel Conjugated Bile Acids. Standards of the novel conjugated bile acids were added to the gut and other samples of germ-free mice to determine the matrix effects on each compound in the targeted method using a triple-quad mass spectrometer (see methods). Although some ion suppression (64% for the phenylalanine conjugated cholic acid in the duodenum) and ion enhancement (135% for the leucine conjugated cholic acid in the duodenum) were observed, the average matrix effects using the positive mode method was 100% (Table 4).

TABLE 4

Matrix effect values for different sample types in positive ionization mode for the conjugated bile acids. The effects are expressed as a percentage from the analyzed chemical standard.

|  | Tyr-Chol | Leu-Chol | Phe-Chol |
|---|---|---|---|
| Stool | 124 | 92 | 95 |
| Jejunum | 99 | 135 | 69 |
| Ileum | 83 | 130 | 87 |
| Duodenum | 124 | 128 | 85 |
| Cecum | 96 | 91 | 64 |

TABLE 4-continued

Matrix effect values for different sample types in positive ionization mode for the conjugated bile acids. The effects are expressed as a percentage from the analyzed chemical standard.

|  | Tyr-Chol | Leu-Chol | Phe-Chol |
|---|---|---|---|
| Colon | 123 | 113 | 95 |
| Stomach | 83 | 96 | 80 |

Calculated matrix effect values were in the range of 80 to 120%, indicating low matrix effects in the ESI positive ion source on these bile acid compounds. Matrix effect was stronger using the negative-mode targeted method, particularly in the blood samples (Table 5) but the limit of detection was 11× lower than positive mode thus it was used for quantification with matrix matched calibration.

TABLE 5

Matrix effect values for different sample types in negative ionization mode using the targeted method for the conjugated bile acids. The effects are expressed as a percentage from the analyzed chemical standard.

|  | Tyr-Chol | Leu-Chol | Phe-Chol |
|---|---|---|---|
| Ileum | 27 | 52 | 48 |
| Cecum | 66 | 79 | 77 |
| Colon | 21 | 23 | 22 |
| Jejunum | 32 | 57 | 55 |
| Fecal | 67 | 83 | 86 |
| Blood | 4 | 22 | 25 |

RT-qPCR analysis of downstream FXR effector genes. The gene expression of Fgf15 and Shp in the ileum and Shp, Cyp8b1 and Cyp7a1 in the liver of mice gavaged with bile acids of interest were analyzed using quantitative reverse transcriptase-PCR analysis. The expression levels were normalized to the cellular housekeeping gene ribosomal phosphoprotein PO (36B4). Mice were sacrificed at both 24 hr (FIGS. 12a-12c) and 72 hr post (FIG. 3e) gavage. At the 24-hr time point expression of the downstream FXR effectors Fgf15 were both significantly elevated (p<0.05) after gavage with Tyr-chol in the ileum, significance was also reached for Shp with cholic acid (CA) and the GW4064 synthetic agonist. In the liver at 24 hrs, Cyp8b1 and Cyp7a1 were significantly reduced in expression in the Tyr-chol, Leu-chol and cholic acid treatments (FIGS. 12a-12c). Shp signaling was not significantly affected at this time point. At 72 hrs post gavage, ileum Fgf15 and Shp signaling were significantly increased for the Tyr-chol, Leu-chol, and CA groups (FIG. 3e). Liver expression of Shp was also significantly elevated, but only in the Tyr and Leu conjugates. The bile acid synthesis enzymes Cyp8b1 and Cyp7a1 were both significantly reduced compared to the corn oil control in Tyr-chol, Leu-chol and CA gavages (FIG. 3e).

Methods

Animals. Germ-free (GF) C57B1/6J mice were generated via caesarian section and microbiologically-sterile animals were cross-fostered by GF Swiss-Webster dams at the California Institute of Technology. GF animals were housed in open-top caging within flexible film isolators (Class Biologically Clean; Madison, WI) and maintained microbiologically sterile, confirmed via 16S rRNA PCR from fecal-derived DNA and culture of fecal pellets on Brucella blood agar or tryptic soy blood agar (Teknova; Hollister, CA)

under anaerobic and aerobic conditions, respectively. The same mice as the GF were grown under non-GF conditions. Conventionally-colonized specific pathogen free (SPF) mice (C57B1/6J) were housed in autoclaved, ventilated, microisolator caging. All animals received autoclaved food (LabDiet Laboratory Autoclavable Diet 5010; St Louis, MO) and water ad libitum, were maintained on the same 12-hour light-dark cycle and housed in the same room of the facility. All animal husbandry and experiments for this component were approved by the California Institute of Technology's Institutional Animal Care and Use Committee (IACUC). All animal dissections and sample collection for the GF and SPF mouse aspect were carried out at University of California at San Diego under IACUC approval, protocol 500227M. For MRI imaging, a female, C57B1/6 mouse, 8 weeks of age, was obtained from Jackson Laboratory and housed with food and water ad libitum. For metabolome and microbiome studies, four germ-free (GF) and four specific-pathogen-free (SPF) female 8-week-old C57B1/6J mice were acquired from the California Institute of Technology's vivarium. Samples of the food the animals were provided were also collected and analyzed (GF were fed LabDiet 5010 and SPF were fed LabDiet 5053, LabDiet, St. Louis, MO).

An additional 24 male ApoE knockout mice in the C57BL/6J background raised for use in a study of hypoxia on the murine microbiome according to the methods of Tripathi et al. 2018[1] were also analyzed in this study for the effects of high-fat-diet and feeding $^{13}$C-Phe on the new bile acids. The fecal samples collected, and the data presented here were not published in that study and approved under IACUC 505534. The source data from this murine experiment is available online.

Human Sample Collection: Fecal samples were collected from two separate pediatric cystic fibrosis patient cohorts for detection of novel bile acids. One sample set was collected from patients at the Rady's Children's Hospital in San Diego, CA using dual fecal swabs according to the procedure outlined in the American Gut Project[2] under IRB approval #160034. The second collection was done on CF patients with pancreatic sufficiency, without pancreatic sufficiency and healthy controls at Yale New Haven Hospital (New Haven, CT) under IRB approval #1206010476 according to the procedure outlined in[3]. Two separate IBD cohorts were also analyzed for the presence of the novel bile acids. The first for detection through GNPS data searching according to the American Gut Project fecal collection protocols and the second for searching a completely different patient cohort with different collection methods and mass spectrometry analysis from the human microbiome project 2 (HMP2) according to the methods of[4]. The UCSD stool sample collections from patients with IBD were collected as part of the UCSD IBD Biobank under IRB #131487. Human infant fecal samples were collected at the University of Michigan under IRB #103575.

3D Model Generation: A female, C57B1/6J mouse, 8 weeks of age, was euthanized using carbon dioxide inhalation and then immediately brought to the UCSD Center for Functional MRI. The MRI images were acquired on a Bruker 7T/20 MRI scanner using a quadrature birdcage transceiver. A 3D FLASH protocol with TE/TR=6 ms/15 ms and matrix size 128×64×156 was used, prescribing a field of view to match the body size. The dicom files from the mouse MRI were imported into the Invesalius software[5]. In Invesalius, the dicom files were visualized as stacked images through the axial, sagittal and coronal slices. Organs of interest were then traced in each slice according to their best visualization in the different viewpoints. The tracing was done using 'create new mask' feature in Invesalius using the manual edition mode. The brush feature was used to trace the outline of each organ of interest in the appropriate slice, stack by stack, until the entire organ was outlined through all slices in each orientation such that its outline was smoothed and did not bleed into other organs. Numerous iterations of this process led to the mapping of each organ through the MRI stacked images. The 'Configure 3D surface' feature was then used to translate the 2D stack tracings into a 3D image of each organ. This was completed for all organs sampled except for blood, fecal and skin samples, successively, until an entire 3D-model of all organs of interest to this study was built. Blender (blender.org) was used to smooth the model and color each organ differently, enabling better visualization of the different organs and organ systems. Blood and skin samples were not mapped onto the model and a representative fecal sample was added after MRI modeling using Invesalius to allow mapping to a theoretical fecal sample.

Sample Collection. Mice were euthanized via carbon dioxide asphyxiation. Prior to dissection, external sites including the skin (left and right flank), ears, mouth and feet were sampled using a cotton swab with vigorous contact for 5 seconds. Blood was collected via cardiac puncture using a 22-gauge needle and 1 ml syringe. Mice were then sterilely dissected under open flame using straight scissors and fine forceps that were cleaned with 70% ethanol (v/v) between handling of each organ. The following organs were dissected: Adrenal gland, bladder, brain, cecum, cervix, colon, duodenum, esophagus, foot, gall bladder, heart, ileum, jejunum, kidney, liver, lung, ovaries, spleen, stomach, thymus, trachea, uterus and vagina. Additional samples were collected using swabs including skin, ear, foot, and mouth. Sections of each organ were made using sterile razor blades. The liver and lung were sectioned into their corresponding lobes (Liver: right and left median lobes, right and left lobes and caudate lobe; Lung: superior lobe, middle lobe, inferior lobe, post-caval lobe and left lung lobe). The heart was sectioned into left and right ventricle and left and right atrium. Each kidney was sub-sectioned by targeting the outer cortex and inner medulla. The uterus was subsampled by collecting each left and right uterine horn and oviduct and a single sample of the uterine fundus. The brain was subsampled by collecting the left and right cerebellum and cerebrum. The GI samples were sectioned into 6 equal length pieces based on the full length of each GI section (including 6 sections of the cecum). Margins of the duodenum and jejunum were determined at the site of the suspensory muscle of the duodenum. The junction of the jejunum and ileum was estimated as 6 cm proximal to the cecum based on previously reported lengths[6]. The GI samples were not cleaned or flushed prior to sample collection. The spleen (4 sections), pancreas (3 sections), adrenal gland (2 sections), and vagina (2 sections) were also sectioned into equal length pieces according to size. It took approximately 45 minutes to fully dissect each mouse immediately after euthanasia. Four stool samples were also collected from each group of mice from the bedding of the sterile shipping containers immediately after arrival in the UCSD analysis laboratory. With such collection method it is not known which mouse produced which stool sample. Food samples fed to both GF and SPF mice were also collected and analyzed. Sample collection for the additional published murine studies were completed according to[1,7]. In addition, fecal samples were collected from mice fed a high-fat diet starting at 10 weeks and compared to animals fed the control normal chow diet according to the methods of[1]. The data from[1] was not published as part of that manuscript.

Sample Processing: All samples were contained in 2 ml sterile Eppendorf® Biopur® Safe-Lock tubes, wet tissue mass recorded, and then frozen at −80° C. until metabolite and DNA extraction. For the swab samples, the wooden end of the swab was cut off with scissors, added to a microcentrifuge tube and 1 ml of PBS was added. After thawing, all of the non-swab samples were diluted in a 1:10 mass:volume in sterile phosphate buffered saline. A Qiagen (Qiagen Inc., Valencia, CA) 5 mm stainless steel bead was added to each tube and the samples were homogenized in a Qiagen TissueLyzer II homogenizer at a frequency of 20/s for 5 min. After homogenization two aliquots of 50 μl of the homogenate or PBS/swab mix was added to separate 96-well deep well plates, one for metabolite extraction and one for DNA extraction. Metabolites were extracted from the samples in the 96-well deep well plate by adding 200 μl of LC-MS grade 70% methanol in LC-MS grade water and vortexing each plate for 5 seconds. Samples were left to extract overnight at 4° C. and then spun down to pellet debris in a 96-well plate Sorvall® Legend centrifuge at 2500 rpm for 1 minute. DNA was extracted from the homogenized tissue according to protocols benchmarked for the Earth Microbiome Project (EMP) found at: earthmicrobiome.org/emp-standard-protocols[8,9].

LC-MS/MS Mass Spectrometry: A 50 μl aliquot of the extracted sample in methanol was added to a 96-well plate and diluted with 150 μl of LC-MS grade methanol containing 2 μl of ampicillin MS internal standard. The chromatographic separation was conducted on a ThermoScientific UltraMate 3000 Dionex UPLC system (Fisher Scientific, Waltham, MA USA) with eluent subsequently electrospray ionized and analyzed with a Bruker Daltonics® MaXis qTOF mass spectrometer (Bruker, Billerica, MA USA). Metabolites were separated using a Kinetex 2.6 μm C18 (30×2.10 mm) UPLC column containing a guard column. Mobile phases A 98:2 and B 2:98 ratio of water and acetonitrile, respectively, containing 0.1% formic acid and a linear gradient from 0 to 100% for a total run time of 840 s at a flow rate of 0.5 mL min$^{-1}$ were used. The mass spectrometer was calibrated daily using Tuning Mix ES-TOF (Agilent Technologies) at a 3 mL min$^{-1}$ flow rate. A lock mass internal calibration was used by soaking a wick with hexakis (1H,1H,3H-tetrafluoropropoxy) phosphazene ions (Synquest Laboratories, m/z 922.0098) located within the source. Full scan MS spectra (m/z 50-2000) were acquired in the qTOF and the top ten most intense ions in a particular scan were fragmented using collision induced dissociation at 35 eV for +1 ions and 25 eV for +2 ions in the collision cell. A data dependent automatic exclusion protocol was used such that an ion was fragmented upon its first detection, then fragmented twice more, but not again unless its intensity was 2.5× the previous fragmentation. The isolation width was dependent on m/z with a 4 m/z isolation for 50 m/z to 8 m/z at 1000 or higher. This exclusion method was cyclical, being restarted after every 30 seconds.

Mass spectrometry data for the mice fed a high-fat diet compared to normal chow for 10 weeks was generated separately from this study on a ThermoScientific™ gExactive™ mass spectrometer according to the procedure of[1]. The mass spectrometry data generation for the HMP2 (PRISM and iHMP datasets) was completed also on a ThermoScientific™ gExactive™, but in negative mode as described in[10]. These methods are less likely to capture known microbiome derived volatiles such as short chain fatty acids.

Metabolomics Data Processing and Analysis. Each LC-MS/MS file in the Bruker format (.d) was converted to mzXML format using the Bruker® DataAnalysis 'Process with Method' batch script. Lock mass calibration was applied during conversion to aid in mass accuracy. The mzXML files were uploaded to the UCSD MassIVE data storage server for GNPS analysis. The entire dataset is publicly available and found under the ID MSV000079949. In addition, the area under curve feature abundances were calculated in batch for all files using the Optimus[11] software based on the OpenMS feature finding algorithms[12]. The Optimus parameters were as follows: m/z tolerance 15.0 ppm, noise threshold of 3000, retention time tolerance of 20 s, intensity factor compared to blanks at 3.0, and a feature observation rate of 0.01. The data was then trimmed to contain information only from 60 s to 550 s of the run during the linear gradient; this removed wash steps programmed into the run at the start and end of the chromatographic program. The feature abundances were normalized to the total ion current (TIC) in each sample for statistical analysis by dividing the area-under-curve abundance for each feature in each sample by the total ion current of that sample (TIC-normalization). For organ-by-organ beta-diversity analysis the features present in individual organs were extracted as separate feature tables and any features not present at all in a particular organ were removed. Additional data for the HFD study[1] was generated with a ThermoScientific™ qExactive™ mass spectrometer, and processed using the mzMine software[13] with the feature table TIC-normalized. Parameters were as follows: MS$^1$ minimum threshold of 10000 counts, MS$^2$ threshold of 5000 counts, a mass tolerance of 0.03 Da and retention time tolerance of 0.2 min. The data was deconvoluted, deisotoped and filtered for compounds present in at least 3 samples. This additional metabolomics dataset is publicly available under MassIVE ID MSV000082480.

Molecular networking was performed on GNPS with the GF and SPF mice samples separated from each other and from blank and quality control samples using the group-mapping feature. The molecular networking and MS-cluster parameters were as follows: parent and fragment ion mass tolerance 0.05 Da, minimum cosine score of 0.7, minimum matched fragment ions of 4, and a minimum cluster size of 4 (to minimize detection of more rare nodes found in few samples). The library search parameters of the molecular networking search were a minimum-matched peaks of 4 and a cosine score of 0.65. Any library hits from the results were inspected directly between the spectrum and query and are considered level two according to the metabolomics standards consortium guidelines[14]. The estimated false discovery rate (FDR) for spectral matching is 4.1% under our search parameters[15]. The full data molecular network used for statistical analysis and annotation is available here: gnps.ucsd.edu/ProteoSAFe/status.jsp?task=9ea760fb819449d7bc7aca8fec07bd8d.

Meta-mass shift chemical profiling of chemical transformations between nodes was done using the method of[16]. Briefly, all nodes unique to either GF or SPF were searched for an edge connection to a node from one or the other groups (GF to SPF, SPF to GF, GF to shared or SPF to shared). This represented a molecule unique in either GF or SPF mice that was related to a molecule in the other group, indicating it was modified in sterile or colonized mice. In each instance, the mass gain or loss relative to the unique node was recorded along with the spectral count for each node as a measure of its abundance. Mass differences were binned into known molecular modifications within a 0.03 Da window as described in[16] with the addition of unique modifications relevant to this dataset, such as saccharides. All other unknown mass shifts were ignored. Mass shifts that were counted included $H_2$ (m/z2.02) acetyl (m/z42.05), methyl (m/z14.02), $H_2O$ (m/z18.01), $C_2H_4$ (m/z28.03) O (m/z16.00), $CH_2O$ (m/z30.91), $NH_3$ (m/z17.03), $C_2H_2$ (m/z26.02), C (m/z12.01), $C_2$ (m/z24.02), $CH_4$ (m/z16.04), $SO_3$ (m/z79.96), $C_4H_8$ (m/z56.06), $2H_2$ (m/z4.03), $C_2H_6$ (m/z30.05), $CH_2O_2$ (m/z46.01), $CO_2$ (m/z43.99), OH (m/z17.01) and sugars corresponding to $C_6H_{10}O_4$ (m/z146.06), $C_6H_{10}O_5$ (m/z162.05), $C_5H_8O_4$ (m/z132.04) and 2 glycone units $C_{12}H_{18}O_{11}$ (m/z338.09). The spectral counts for node representing the specific modification were summed and plotted as total spectral counts for that modification in GF and SPF mice as either mass gains or losses.

16S rRNA Gene Amplicon Sequencing of Mouse Samples: On all murine samples collected both GF and SPF and control samples of solutions and swabs underwent DNA extraction, 16S rRNA gene variable region 4 (V4) PCR and amplicon preparation for sequencing according to protocols benchmarked for the Earth Microbiome Project (EMP) found here: earthmicrobiome.org/emp-standard-protocols[9,17]. The microbiome data was processed through the Qiita software (qiita.ucsd.edu). The data was demultiplexed, reads trimmed to 150 bp, and Deblur[18] was used to de-noise the data into sub-OTUs (sOTUs). The resultant .biom files were used for downstream analysis with QIIME[8]. To create a phylogenetic tree for UniFrac[19] analysis, deblurred sOTU sequences were inserted into the annotated Greengenes[20] tree with SEPP[21] and taxonomy assigned using the corresponding taxonomic label on the internal node where the sequence inserted. The microbiome data is available at (qiita.ucsd.edu, study ID:10801).

3D Mapping in 'ili: Metabolomics and microbiome data were mapped onto the 3-D mouse model by recording the location of the sampling and orientation of each sample in the model according to the methods described in[11]. Some organs only contained one sample (bladder, blood, cervix, gall bladder and thymus) all other organs contained 2-6 samples and the actual location of the dissected sample was mapped to the appropriate point representing that same sample in the 3D model. The point mapping was done using the GeoMagic® Wrap software. The full .stl model of the laboratory mouse was loaded into GeoMagic Wrap and the location of each sampling point was selected with the 'points' tool (available as supplemental data). The x,y,z coordinate information in the model from all points was then exported as a .csv file for matching to its representative sample in the metabolomics or microbiome data (available as supplemental data). Sub models of different organ systems were also created in the same manner to aid visualization, such as the GI tract and liver. Mapping to these models was done as described for the full model. For 'ili visualization, the matching samples for the 4 GF and 4 SPF mice were averaged and a new feature or OTU table created based on these mean abundances. This feature table was then matched to the x,y,z coordinates from the model according to the correct sample. This OTU or metabolite feature table was then uploaded into the 'ili software simultaneously with the mouse model. This enabled automatic mapping of the abundance of a microbial or metabolite variable to the point representing its collection location in the GF and SPF mouse 3D-model. Visualization in 'ili was done using a linear scale with the 'viridis' color map and automatic min/max mapping was selected.

Statistical Analysis Of the Mouse Data: The microbiome .biom table and metabolome feature table were analyzed using principal coordinate analysis after calculation of a distance matrix between all samples. Alpha diversity of the metabolome data was calculated using the Shannon-Weiner index on the TIC-normalized feature table from the murine GI tract in the R statistical software. The microbiome distance matrix was generated using the unweighted UniFrac distance[22] in QIIME and QIIME2. Beta-diversity of the microbiome data was calculated on a feature table rarified to 500 reads per sample to enable visualization of GF and sterile samples which had a low number of 16S rDNA gene reads. Repetition at higher read thresholds produced very similar results for the SPF samples, as expected from prior studies. The metabolomic beta-diversity was calculated using the Bray-Curtis dissimilarity. The resulting distance matrix was visualized using principal coordinates analysis (PCoA) and each sample highlighted by either GF/SPF or organ source for both groups of mice. To assess the overall similarities between the metabolome of murine organs the Bray-Curtis dissimilarity was calculated between all paired samples (compared for the same subsection location for the same organ) between the GF and SPF states for all mice and these dissimilarities were averaged per organ and plotted with notch plots. This same comparison was done within GF and SPF groups to determine the level of variation for mice of the same classification. In addition, the within group variation was compared between GF and SPF mice separately in the same manner.

To determine the number of unique metabolites between GF and SPF in each organ molecular networks were built with the same above parameters for samples from each of the 29 organs. The molecular networking data was then downloaded from GNPS and the source of each node as GF or SPF was tabulated. A spectrum was considered unique to either class of mice only if it was detected in at least 3 out of 4 individual mice sampled per category. Each instance of these unique nodes was counted and reported as a percentage of the total number of nodes from each organ and as the total number of nodes per organ to visualize abundance. This was also done at the level of each individual mouse comparison to obtain a degree of variation in the overall unique metabolite differences.

To visualize the effect of the GF or SPF classification on the gut metabolomic data a random forests classification was run on all GI tract samples (including the esophagus) and the variable importance for classification of each metabolite was determined. The random forest analysis was done using 5000 trees with the R-statistical package 'random forests'. The variable importance plot was then computed for the metabolites most differentiating the GF and SPF states of the animals. These variables of importance were analyzed for known compounds in GNPS and their molecular family memberships. The 30 most differentially abundant metabolites according to their variable importance were then visualized using a stacked bar graph showing their relative abundance to the entire metabolome. This enabled visualization of the changes in the most differential metabolites through the GI tract and an indication of how abundant these differential metabolites were overall. The Shannon-Weiner index of diversity was calculated on the entire metabolome from each GI tract associated sample using the R statistical software. The mean Shannon-Weiner diversity for each sample location was visualized for the two groups of mice through the GI tract. The Mann-Whitney U-test was used to determine a statistically significant difference ($p<0.05$) between the Shannon diversity of each GI tract sample collected at the same location between the GF and SPF mice. The microbiome diversity was calculated using the Faith's phylogenetic diversity index in the Qiita software and mean diversity between the four individual mice was presented only for the SPF mice.

Tests of the differential abundance of the novel bile acids between mice fed antibiotics or high fat were done using the Mann-Whitney U-test with a significance level of p<0.05. Correlations between the feature abundance of the novel bile acids and bacterial OTUs from the HFD experiment were calculated using the Pearson's correlation on deblurred reads. Reads with the highest correlations were assigned by BLAST to the NCBI nucleotide database with only cultured representatives included in the search.

The alpha diversity of the batch culture experiment was calculated using the Shannon-Index on the deblurred OTU table produced through Qiita and the duplicate sequenced samples were averaged.

Synthesis of Novel Conjugated Bile Acids. The procedure was adapted from a previous method by Ezawa et al.[23] Cholic acid (100 mg, 0.25 mmol, 1 eq.) was dissolved in THF (4.9 mL, 0.05 mM) and cooled to 0° C. in an ice water bath with stirring. Ethyl chloroformate (28 μL, 1.2 eq.) was added followed by triethylamine (41 μL, 1.2 eq) and the reaction stirred for 0.5 hours cold. After complete conversion of the starting material by TLC a cold, aqueous solution (4.9 mL) of amino acid (0.37 mmol, 1.5 eq.) and base (0.37 mmol, 1.5 eq.) is added in one portion. The reaction is stirred for 1 hour at 0° C. to completion. THF is removed under reduced pressure and 2 M HCl is added to acidify to pH <2 and a white precipitate appears. The mixture was extracted with ethyl acetate (3×20 mL), the combined organic layers washed with brine (1×50 mL), dried over sodium sulfate, and concentrated. Purification was done by column chromatography with 6%→18% Methanol/DCM+1% acetic acid to give the desired product as a white solid.

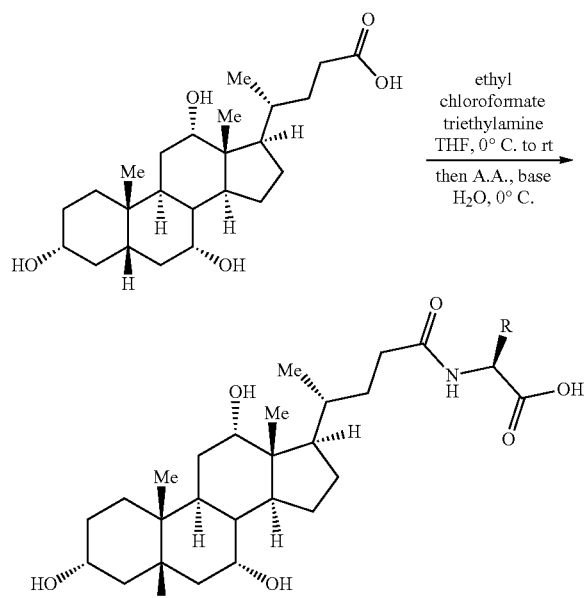

Leucine Conjugate: 62% Yield. Product made using the general procedure. White solid. $^1H$ NMR (600 MHz, MeOD) δ4.37 (s, 1H), 3.96 (s, 1H), 3.80 (d, J=2.6 Hz, 1H), 3.40-3.34 (m, 1H), 2.36-2.22 (m, 3H), 2.21-2.13 (m, 1H), 2.03-1.94 (m, 3H), 1.93-1.78 (m, 4H), 1.78-1.51 (m, 10H), 1.47-1.27 (m, 5H), 1.15-1.06 (m, 1H), 1.04 (d, J=6.5 Hz, 3H), 1.02-0.94 (m, 4H), 0.94-0.89 (m, 6H), 0.71 (s, 3H). $^{13}C$ NMR (151 MHz, MeOD) δ176.80, 74.05, 72.87, 69.04, 48.12, 47.49, 43.18, 42.99, 41.96, 41.00, 40.44, 36.91, 36.48, 35.90, 35.85, 34.02, 33.33, 31.16, 29.56, 28.73, 27.86, 26.13, 24.24, 23.56, 23.16, 21.81, 17.73, 13.00. M.P.=175-178C. IR—3390.24, 2933.2, 2868.59, 2426.01, 1634.38, 1464.67. HRMS (ESI) exact mass calculated for $[M+H]^+$ ($C_{30}H_{52}NO_6$) requires m/z 522.3789, found 522.3793 with a difference of 0.77 ppm.

Isoleucine Conjugate: 58% Yield. Product made using the general procedure. White solid. $^1H$ NMR (599 MHz, MeOD) δ4.32-4.27 (m, 1H), 3.96 (s, 1H), 3.80 (d, J=2.8 Hz, 1H), 3.40-3.34 (m, 1H), 2.38-2.15 (m, 4H), 2.03-1.93 (m, 3H), 1.93-1.78 (m, 4H), 1.78-1.50 (m, 10H), 1.45-1.27 (m, 4H), 1.26-1.19 (m, 1H), 1.11 (qd, J=11.8, 5.6 Hz, 1H), 1.05-1.02 (m, J=7.0, 2.0 Hz, 3H), 1.01-0.90 (m, 10H), 0.71 (s, 3H). $^{13}C$ NMR (151 MHz, MeOD) δ176.86, 74.06, 72.87, 69.04, 48.12, 47.48, 47.48, 43.18, 42.98, 41.00, 40.44, 38.33, 36.93, 36.48, 35.89, 35.84, 33.87, 33.35, 31.16, 29.56, 28.72, 27.86, 26.24, 24.23, 23.17, 17.73, 16.15, 13.00, 11.85. M.P.=144-148C. IR—3392.17, 2933.2, 2871.49, 2483.87, 1639.20, 1461.78. HRMS (ESI) exact mass calculated for $[M+H]^+$ ($C_{30}H_{52}NO_6$) requires m/z 522.3789, found 522.3792 with a difference of 0.57 ppm.

Phenylalanine Conjugate: 63% Yield. Product made using the general procedure. White solid. $^1H$ NMR (599 MHz, MeOD) δ7.28-7.17 (m, 5H), 4.60 (dd, J=8.9, 4.8 Hz, 1H), 3.93 (t, J=2.7 Hz, 1H), 3.80 (d, J=2.8 Hz, 1H), 3.40-3.35 (m, 1H), 3.22 (dd, J=13.9, 4.8 Hz, 1H), 2.94 (dd, J=13.9, 9.1 Hz, 1H), 2.33-2.18 (m, 3H), 2.11-2.04 (m, 1H), 2.01-1.94 (m, 3H), 1.86-1.78 (m, 3H), 1.76-1.63 (m, 3H), 1.62-1.50 (m, 5H), 1.4-1.33 (m, 3H), 1.21 (m, 2H), 1.09 (qd, J=11.9, 5.3 Hz, 1H), 1.02-0.95 (m, 4H), 0.92 (s, 3H), 0.68 (s, 3H). $^{13}C$ NMR (151 MHz, MeOD) δ17138.76, 130.28, 129.38, 127.68, 74.04, 72.87, 69.04, 48.02, 47.44, 43.18, 42.97, 40.99, 40.44, 38.47, 36.84, 36.48, 35.89, 35.84, 33.87, 33.23, 31.16, 29.56, 28.66, 27.86, 24.22, 23.16, 17.66, 13.00. M.P.=142-146C. IR—3395.07, 2934.16, 2865.70, 2494.47, 1638.23, 1455.99. HRMS (ESI) exact mass calculated for $[M+H]^+$($C_{33}H_{50}NO_6$) requires m/z 556.3633, found 556.3637 with a difference of 0.72 ppm.

Tyrosine Conjugate: 57% Yield. Product made using the general procedure. White solid. $^1H$ NMR (599 MHz, MeOD) δ7.03 (d, J=8.5 Hz, 2H), 6.68 (d, J=8.5 Hz, 2H), 4.52 (dd, J=8.6, 4.8 Hz, 1H), 3.94 (t, J=2.7 Hz, 1H), 3.80 (d, J=2.8 Hz, 1H), 3.40-3.34 (m, 1H), 3.11 (dd, J=14.0, 4.8 Hz, 1H), 2.84 (dd, J=13.9, 8.8 Hz, 1H), 2.33-2.20 (m, 3H), 2.07 (m, 1H), 2.02-1.93 (m, 3H), 1.88-1.78 (m, 3H), 1.77-1.63 (m, 3H), 1.62-1.51 (m, 5H), 1.45-1.34 (m, 3H), 1.27-1.18 (m, 2H), 1.10 (qd, J=11.8, 5.4 Hz, 1H), 1.02-0.95 (m, 4H), 0.92 (s, 3H), 0.69 (s, 3H). $^{13}C$ NMR (151 MHz, MeOD) δ176.65, 157.21, 131.26, 129.41, 116.10, 74.05, 72.87, 69.05, 48.05, 47.44, 43.17, 42.97, 40.99, 40.44, 37.73, 36.85, 36.47, 35.89, 35.83, 33.95, 33.26, 31.16, 29.55, 28.67, 27.86, 24.23, 23.16, 17.67, 13.00. M.P.=174-178C. IR—3398.92, 2936.09, 2867.63, 1614.13, 1446.35. HRMS (ESI) exact mass calculated for $[M+H]^+$ ($C_{33}H_{50}NO_7$) requires m/z 572.3582, found 572.3584 with a difference of 0.35 ppm.

$^{13}C_9$, $^{15}N$-labelled Tyrosine Conjugate: 94% yield. Product made using the general procedure with slight modifications. The reaction time for initial activation of the carboxylic acid at 0° C. was extended from 0.5 h to 2 h. Additionally, following addition of the labelled tyrosine and NaOH, the reaction time was extended to 2 h. The product was obtained as a white solid. $^1$H NMR (599 MHz, MeOD) δ7.21-6.86 (m, 2H), 6.85-6.52 (m, 2H), 4.56 (d, J=141.7 Hz, 1H), 3.94 (t, J=3.0 Hz, 1H), 3.80 (q, J=3.1 Hz, 1H), 3.41-3.35 (m, 1H), 3.27-2.97 (m, 1H), 2.97-2.67 (m, 1H), 2.33-2.19 (m, 3H), 2.14-2.04 (m, 1H), 2.03-1.90 (m, 3H), 1.89-1.77 (m, 3H), 1.77-1.62 (m, 3H), 1.62-1.48 (m, 5H), 1.47-1.32 (m, 3H), 1.25-1.16 (m, 2H), 1.09 (qd, J=11.9, 5.6 Hz, 1H), 1.03-0.94 (m, 4H), 0.91 (s, 3H), 0.68 (s, 3H). $^{13}$C NMR (151 MHz, MeOD) δ157.13, 157.06, 131.21 (t, J=55.2 Hz), 128.95, 116.16 (t, J=62.4 Hz), 74.05, 72.82, 69.08, 49.43, 49.28, 49.14, 49.00, 48.86, 48.72, 48.57, 48.00, 47.39, 43.06, 42.90, 40.88, 40.35, 37.56 (dd, J=47.0, 27.7 Hz), 36.77, 36.41, 35.83, 35.75, 33.84, 33.20, 31.08, 29.46, 28.60, 27.78, 24.19, 23.13, 17.66, 12.98.

Novel Bile Conjugates Validation Experiments. To validate the synthetic standards of the tyrosine, phenylalanine, leucine and isoleucine cholic and muricholic acids conjugates, the compounds were dissolved in methanol, diluted to 5 µM and run on the LC-MS/MS method described above. The data is publicly available under MassIVE ID: MSV000082467. Retention times and MS/MS spectra were analyzed to verify the molecular characteristics. To determine the approximate concentration of Phe-chol in the murine GI tract an ileal sample from a GF mouse was spiked with standard curve of concentrations of pure Phe-chol (non-murine form). Final concentrations of 100 µM, 25 µM, 5 µM, 1 µM, 0.1 µM and 0.02 µM, were directly added to the extracted ileal sample and analyzed with mass spectrometry using the same methods as described above. A standard curve of these concentrations was calculated by plotting the known concentrations to their corresponding area-under-curve (AUC) abundance of the Phe-chol peak. The same AUC abundance was then captured for each sample positive for the molecule in the colonized mice. The concentration in the murine samples was then calculated based on the concentrations of the standard curve. Because isoleucine and leucine cannot be distinguished with MS/MS data, the synthetic isoleucocholic acid standard and leucocholic acid standard on an extended gradient HPLC column was analyzed. The two standards were injected with the jejunum3 sample from mouse SPF2 and subjected to a 40% LC gradient of the same solvents described above with ramp to 40% solvent B at 3 minutes followed by 22 min of ramping to 100% B and then wash steps. The MS/MS method was identical to that described above and retention time differences were recorded between the two chemical standards and the murine sample. To determine whether the base bile acid was either cholic or muricholic acids, the muricholic forms were synthesized according to the supplementary methods in place of cholic acids and all 3 amino acid conjugates of each bile acid backbone were analyzed using the original LC-MS/MS with sample SPF2 jejunum 3, which contained the same molecules detected in the murine gut. Retention time analysis was used to identify whether each molecule in the mouse sample was either muricholic or cholic acid forms. Mirror plots showing matches between the novel conjugated bile acids in the murine data and standards are found as follows Leu-chol: gnps.ucsd.edu/ProteoSAFe/result.jsp?task=7ec1a92395c540d78faa34613a64deac&view=view_all_annotations_DB #%7B%22main.Compound_Name_input%22%3A%22leuco%22%7D Phe-chol gnps.ucsd.edu/ProteoSAFe/result.jsp?task=7ec1a92395c540d78faa34613a64deac&view=view_all_annotations_DB #%7B%22main.Compound_Name_input%22%3A%22phenylalano%22%7D Tyrososocholic Acid gnps.ucsd.edu/ProteoSAFe/result.jsp?task=7ec1a92395c540d78faa34613a64deac&view=view_all_annotations_DB #%7B%22main.Compound_Name_input%22%3A%22tyroso%22%7D Mining Public Data Mining on GNPS. The single spectrum search feature in GNPS (MASST, gnps.ucsd.edu/ProteoSAFe/index.jsp?params=%7B %22workflow%22:%22SEARCH_SINGLE_SPECTRUM%22, %22library_on_server%22:%22d.speclibs;%22%7D) that allows one to search public MS/MS data through spectral alignment[11] was used to search for the unique amino acid conjugated bile acids in publicly available data. The parameters of the search were as follows: 0.03 Da window of parent mass and fragment ion matching, 0.7 cosine score and a minimum matched peaks of 4 ions. In datasets with a positive hit, the source organism and % of samples positive for each compound was recorded. Two datasets comprised of LC-MS/MS data analyzed on a Bruker Maxis qTOF from fecal swabs of CF patients (massive IDs MSV000079134 and MSV000082406) were further analyzed according to the metadata of the studies as pancreatic sufficient, insufficient or samples from healthy individuals. The presence of an MS/MS spectrum for each of these classes was tabulated by individual and reported as the percent of subjects positive for each molecule in each class.

Development of UPLC-Triple Quadrupole Mass Spectrometry Method for Bile Acids Quantification and Assessment of Matrix Effects. The above chromatography method used in the murine tissues analysis was transferred to a Thermo Ultimate 3000 UHPLC coupled with a Thermo TSQ Quantum Access Max ESI triple quadrupole (QQQ) system. An identical column, mobile phases, sample injection volume, and column thermostat temperature setting were used as described in the LC-MS/MS section above. However, In order to increase sample throughput, the gradient was slightly modified: gradient elution was set to start with one-minute hold at 5% organic composition, then linearly increase to 90% over four minutes followed by 90% organic content hold for 2 minutes and decrease to 5% and hold for 5 minutes to equilibrate the system before the subsequent injection. The flow rate was set to 0.25 ml/min to match optimal operating regime for the QQQ mass analyzer. The ESI sprayer parameters are summarized in Table 3.

TABLE 3

MRM transitions and mass spectrometry details for targeted method. a) Negative mode b) positive mode. Other details of the mass spectrometry method are also provided

| | a) Negative Mode | | | | |
|---|---|---|---|---|---|
| | Q1 | Q3 | CE | Tube lens | tr (min) |
| Leu | 520.4 | 130.2 | 44 | 100 | 6.31 |
| Leu | 520.4 | 458.2 | 38 | 100 | 6.31 |
| Phe | 554.4 | 147.2 | 42 | 100 | 6.38 |

TABLE 3-continued

MRM transitions and mass spectrometry details for targeted method. a) Negative mode b) positive mode. Other details of the mass spectrometry method are also provided

| | | | | | |
|---|---|---|---|---|---|
| Phe | 554.4 | 164.1 | 42 | 100 | 6.38 |
| PheC13 | 555.4 | 148.2 | 44 | 100 | 6.38 |
| PheC13 | 555.4 | 165 | 42 | 100 | 6.38 |
| Tyr | 570.4 | 119.1 | 48 | 100 | 5.96 |
| Tyr | 570.4 | 179.9 | 38 | 100 | 5.96 |
| Tyr10 | 580.4 | 190 | 41 | 150 | 5.96 |
| Tyr10 | 580.4 | 535.2 | 38 | 150 | 5.96 |

Spray voltage 2500
Vaporizer Temperature 267
Sheath gas pressure 39
Aux gas pressure 33
Capillary temperature 355 b)
Positive Mode

| | Q1 | Q3 | CE | Tube lens | |
|---|---|---|---|---|---|
| Leu | 522.4 | 337 | 25 | 170 | 9.36 |
| Leu | 522.4 | 468.1 | 19 | 170 | 9.36 |
| Phe | 556.4 | 337.1 | 23 | 190 | 9.6 |
| Phe | 556.4 | 389 | 37 | 190 | 9.6 |
| Tyr | 572.4 | 337.1 | 20 | 160 | 8.5 |
| Tyr | 572.4 | 518 | 17 | 160 | 8.5 |

Spray voltage 3000
Vaporizer Temperature 350
Sheath gas pressure 39
Aux gas pressure 33
Capillary temperature 380

Multiple reaction monitoring (MRM) transitions were selected to achieve the highest sensitivity and specificity of the targeted molecules. The optimal MRM transitions were selected independently for both regular and stable $^{13}$C-Phenylalanine isotopic labeled synthetic conjugate and $^{13}C_9$, $^{15}$N-Tyrosine isotopic labeled synthetic conjugate. The Retention Time (RT) and two transitions per molecule were used for the specificity to achieve level 1 annotation[14]. These MRM parameters of all quantified molecules are summarized in Table 3.

Assessment of Matrix Effects and Measuring of Limit of Detection (LOD) in Different Matrices Matrix effects on the novel conjugated bile acids from the murine GI tract samples were evaluated to characterize the interferences observed during the untargeted analysis. For this, sample aliquots for each tissue and sample type of GF mice were pooled together, injected, and quantified using an external standard calibration. The calibration curve was created using standards in the 5 ng/ml to 250 ng/ml range. The same samples were also spiked with the 50 ng/ml of each bile acid conjugate and analyzed in identical fashion. Matrix effect values were calculated by comparing the expected value (50 ng/ml) to the difference observed between the assayed samples and the samples with added standard (Table 3). As the matrix could affect the LODs due to ion suppression or ion enhancement; the GF samples (which do not contain the target compounds) were spiked with different concentrations and injected to the HPLC-MS system. Limit of detection was calculated as three times of the standard error of the fitted regression line divided by the slope for each conjugate separately and for each tissue type.

Quantification of Novel Bile Conjugates in SPF mice with Internal Standard Calibration and Matrix Matched Calibration. The original samples from SPF mice were re-analyzed with the HPLC-ESI-QQQ targeted quantification method described above with two separate quantification approaches. 1) Internal Standard Calibration: all samples were injected with 2 μL of $^{13}$C-Phenylalanine isotopic labeled synthetic bile conjugate and $^{13}C_9$,$^{15}$N-Tyrosine isotopic labeled synthetic bile conjugate as internal standard mixture (250 ng/ml); mixed in the HPLC injector loop. As the Phe-chol internal standard only had one $^{13}$C modification the natural distribution contribution of the M+1 isotope was corrected during the calculation. 2) Matrix-matched calibration: calibration curves were built to cover the range of 2.5 ng/ml to 1 μg/ml for each tissue type by adding external standards into pooled GF mice samples lacking targeted bile conjugates. For both calibrations, linear fitting was used to determine slope and intercept of the calibration curve. These parameters were used to calculate the concentration of unknown samples. The obtained concentrations were then expressed in M/g quantities based on masses of original samples.

Quantification of The Phenylalanine Bile Acid Conjugate Production by Bacterial Strains. Correlations between the novel bile acids were assessed using the Pearson correlation and mmvec[25]. Cultures of C. bolteae CC43 001B and C. bolteae WAL-14578 strains were extracted as previously described for the mouse sample processing method. The bile acids in the extracts were quantified using targeted quantification method described above. Elution gradient was set to start with one-minute hold at 5% organic composition, then linearly increase to 90% over four minutes followed by 90% organic content hold for 2 minutes and decrease to 5% and hold for 5 minutes to equilibrate the system before the subsequent injection. The flow rate was set to 0.25 ml/min throughout. The calibration curves were calculated from a range of 0.25 ng/ml to 100 ng/ml with standards.

Fecal Culture Bioreactor Inoculation. A 4 g stool sample was resuspended in 40 mL modified yeast casitone fatty acids media (mYCFA, DMSZ recipe) with 0.25% Antifoam B Silicon Emulsion (Baker) in a vinyl anaerobic chamber (Coy). The resuspension was centrifuged at 500× g for 5 minutes to pellet solids. The supernatant was decanted through a sterile 70 μM filter. The filtrate was centrifuged at 4450× g for 10 minutes to pellet cells. The supernatant was discarded, and the pellet was resuspended in 40 mL mYCFA. The resuspension was drawn into a 60 mL syringe and injected into a 500 mL vessel of an Infors Multifors 2 bioreactor. The chemostat process parameters was modified from a previous process developed in[26]. The chemostat volume parameters were; 400 mL culture volume, 24-hour retention rate, 50 mL/min nitrogen, stirrer at 250 rpm, and 37° C. temperature. 10 mM stocks of cholic acid, chenodeoxycholic acid, glycocholic acid, Leu-chol, Phe-chol and Tyr-chol were prepared in 100 μL methanol. 15 μL stocks were added to 12 mL mYCFA. After 11 days of continuous culturing, 24 mL bioreactor culture was withdrawn and transferred to the anaerobic chamber. 3 mL culture was added to the 12 mL mYCFA aliquots with the bile acids, for a total volume of 15 mL and final concentration of 10 μM bile acid. The cultures were vortexed and split into three 5 mL aliquots. At time 0 (blanks for each bile acid), 1, 3, 6, 12 and 24 hours, 0.1 mL aliquots were removed from the samples for metabolomics and 16S rRNA gene sequencing.

A separate experiment in 96 deep-well plate format was completed in similar fashion with media formulated according to[26] (designed to mimic human gut contents). A fresh fecal swab (sampled according to methods from the American Gut Project[2]) was first resuspended in 1×PBS and then 20 μL of fecal resuspension was inoculated into 500 μL of media in each well. Conjugated bile acids (Phe-chol, Tyr-Chol, Leu-Chol and Gly-chol) were added to the cultures prior to incubation in triplicate. The cultures were incubated at 37° C. for 48 hours. Both culture experiments (batch culture and 96-well plate format) were extracted with 70% methanol according to the same methods described above and analyzed with LC-MS/MS using the same instrument and methods as described above for GF and SPF mouse studies. The batch culture experiment had microbiome sequencing completed and analyzed.

16S rRNA Gene Amplicon Sequencing of Batch Cultures. DNA was extracted from the bioreactor samples using QIAGEN AllPrep 96 PowerFecal DNA/RNA, (QIAGEN custom product #1114341) with bead-beating on a Tissuelyser II (QIAGEN). 16S rRNA gene libraries targeting the V4 region of the 16S rRNA gene were prepared by first using qPCR to normalize template concentrations and determine optimal cycle number. To ensure minimal over-amplification, each sample was normalized to the lowest concentration sample, amplifying with this sample optimal cycle number for the library construction PCR. Four 25 μL reactions were prepared per sample with 0.5 units of Phusion with 1× High Fidelity buffer, 200 μM of each dNTP, 0.3 μM of 515F and unique reverse barcode primer from the Golay primer set[9]. After amplification, replicates were pooled and cleaned via Agencourt AMPure XP-PCR purification system. Prior to final pooling, purified libraries were diluted 1:100 and quantified again via qPCR (Two 25 μL reactions, 2×iQ SYBR SUPERMix (Bio-Rad, REF: 1708880 with Read 1. Pools were quantified by Qubit (Life Technologies, Inc.). Final pools were sequenced on an Illumina MiSeq 300.

Farnesoid X Receptor Stimulation from Bile Acids. Human kidney cell line HeK-293 was obtained from American Type Culture Collection (ATCC CRL-1573, tested for *Mycoplasma* contamination every 6 months). These cells were chosen due to their high transfectability and low FXR expression which allows for a robust signal to noise ratio. These 293 cells were cultured in Dulbecco's modified Eagle's medium/F-12 (DMEM) supplemented with 10% (V/V heat-inactivated fetal calf serum (FBS) and 100 units/ml penicillin G and 100 μg/ml streptomycin. 10,000 cells were seeded per well in 96-well plates one day before transfection of plasmids. DNA was transiently transfected by Lipofectamine 2000 and Opti-MDM in fasting state. The ratio of plasmid used in per well were 50 ng of FXR response element (FXRE)/luciferase reporter plasmid, 10 ng of pCMV-3flag-FXR (human) plasmid, 10 ng of pCMV-RXR (human) plasmid, and 5 ng of Renilla luciferase reporter plasmid as internal standard for transfection efficiency. After 12 hrs of transfection, 293 cells were treated with the indicated concentration of bile acids (Phe-Chol, Tyr-Chol, Leu-Chol, CDCA, DCA and T-βMCA.) with FXR synthetic agonist GW4064 as control. Cells were harvested 24 hrs later and lysed with passive lysis buffer (Promega). Luciferase activities were measured by the Dual-Luciferase Reporter (DLR™) Assay kit and read by Luminometer (Perkin Elmer). The final Luciferase activities were normalized by dividing the relative light units by Renilla luciferase activity. Statistical analyses were performed using Prism software. Each dosage was done in 12 replicates.

$13_C$-Phenylalanine Feeding of Mice and Analysis of Fecal Samples. ApoE$^{-/-}$ (Jackson Labs Stock No. 002052) females approximately 16 weeks old were used for this experiment. Fecal pellets were collected from each mouse at baseline (mice were fed regular chow (RC) prior to experiment) and each day after for the duration of the experiment HFD feeding (between 9-11 am each day). Each mouse was housed in an individual cage lined with nestlets. The diet was then shifted to HFD containing 1.25% cholesterol and 21% milk fat (TD96121; Envigo, Madison, WI) at day 0. The overall experiment duration was 9 days with the final stool collection being on day 10. On days 1-3, each mouse was fed the HFD alone. On days 4-6, the experimental mouse was shifted to HFD supplemented with the $^{13}$C-labeled phenylalanine (Catalog #490091 Sigma-Aldrich) and the control mouse to HFD supplemented with unlabeled phenylalanine. Both groups of mice were shifted back to the HFD without supplemental phenylalanine on days 7-9. The food was prepared as follows each day: each day the HFD pellets were mixed with water from the mouse bottles at 1.5 mL water per 10 grams of food to make a uniform slush inside a small dish that is placed on the cage bottom. For days 4-6, the amino acid powder at 10 μg/mg was spread on top of the food, water was added and mixed. Fecal samples were collected from these animals and screened for the production of labeled and unlabeled Phe-chol. Fecal samples from the feeding experiment were extracted and prepared with the same protocol as described above for the original GF and SPF mice. Targeted analysis method was used for detection of phenylalanine conjugates for both unlabeled and $C^{13}$ labeled molecules. The areas under the curves were extracted and used for ratio calculations.

LC-MS Metabolomics Data Processing from PRISM and iHMP cohorts from the HMP2 IBD Datasets. The raw LC-MS data were acquired to the data acquisition computer interfaced to each LC-MS system and then stored on a robust and redundant file storage system (Isilon Systems) accessed via the internal network at the Broad Institute. Nontargeted data were processed using Progenesis QIsoftware (v 2.0, Nonlinear Dynamics) to detect and de-isotope peaks, perform chromatographic retention time alignment, and integrate peak areas. Peaks of unknown ID were tracked by method, m/z and retention time. The novel conjugated bile acids were searched for by matching m/z in negative mode and subsequently verified using LC-MS/MS and synthetic standards of Phe-chol, Tyr-chol and Leu-chol from pooled samples (Table 6).

Statistical Analysis of HMP2 Metabolomics Data. Prior to model fitting, raw metabolite abundances were median-normalized within sample and then log-transformed with a pseudocount of 1. We used linear models implemented in R to associate metabolite abundances with IBD phenotype while controlling for clinical covariates. For the cross-sectional PRISM data, we treated categorical IBD diagnosis (UC, CD, and non-IBD control) as the phenotype of interest with "non-IBD" as a reference group. Age was included as a continuous covariate, while antibiotics, immunosuppressants, mesalamine, and steroids use were coded as binary covariates. The model was evaluated as follows using R's /m function:

metabolite~(intercept)+diagnosis+age+antibiotic+
immunosuppressant+mesalamine+steroids.

The nominal p-values of the diagnosis coefficients for each metabolite were adjusted for multiple hypothesis testing using the Benjamini-Hochberg FDR method. A more sophisticated mixed-effects model was applied per-feature to the HMP2 metabolomics data to account for repeated measures over subjects and the multiple recruitment sites within the study. In addition, the transformed abundance of each metabolite was modeled as a function of a combined phenotype: diagnosis (as defined above) and dysbiosis state as a nested binary variable within each diagnosis (with non-dysbiotic as reference). The definition of "dysbiosis state" is presented in detail in the next section. Model results were further adjusted for consent age as a continuous covariate and antibiotics use as a binary covariate. The mixed effects model was evaluated as follows using the lme function in R's nlme package [where (1 | subject) and (1 | recruitment site) indicate random effects for subject and recruitment site, respectively]:

metabolite~(intercept)+diagnosis+diagnosis/dysbiosis+antibiotic use+consent age+(1|recruitment site)+(1|subject)

Statistical significance (p-value) of metabolite-phenotype associations were assessed using Wald's test and corrected for multiple hypothesis testing as described above.

Dysbiosis analyses/Dysbiosis score. To identify samples with highly divergent (dysbiotic) metagenomic microbial compositions in the HMP2 dataset, a "dysbiosis score" was defined as in[10] based on Bray-Curtis dissimilarities to non-IBD metagenomes. First, a "reference set" of samples was constructed from non-IBD subjects by taking all samples after the 20th week after the subject's first stool sample. This was chosen since a subset of the non-IBD subjects at the start of their respective time series may not yet have overcome any gastrointestinal symptoms that triggered the initial visit to a doctor, though ultimately not caused by IBD. The dysbiosis score of a given sample was then defined as the median Bray-Curtis dissimilarity to this reference sample set, excluding samples that came from the same subject. To identify highly divergent samples, we then thresholded the dysbiosis score at the 90th percentile of this score for non-IBD samples. This therefore identifies samples with a feature configuration that has a <10% probability of occurring in a non-IBD subject. By this measure, 272 metagenomes were classified as dysbiotic. Samples from CD and UC subjects are overrepresented in the dysbiotic set, with 24.3% and 11.6% of their samples classified as dysbiotic, respectively. A metabolite measurement was then defined as dysbiotic only if its paired metagenome is defined as dysbiotic according to the above definition. Only metabolomes with matched metagenomes were used in differential abundance testing (for UC, 12 dysbiotic and 110 non-dysbiotic metabolomes; for CD, 48 dysbiotic and 169 non-dysbiotic).

Bile acid Gavage of Mice. Eight-week-old Male C57BL/6J mice (Jackson Laboratory) were acclimated for 14 days and housed in groups of two throughout the duration of the experiment to mitigate cage effects. Mice were then dosed 2 times (24 hour) or 4 times (72 hour) (t=0 hr, t=24 hr, t=48 hr, t=72 hr) by oral gavage with either a mock control of corn oil without bile acids, or corn oil infused Tyr-chol (500 mg/kg body weight), Leu-chol (500 mg/kg body weight), cholic acid (500 mg/kg body weight) or the control FXR agonist GW4064 (10 mg/kg body weight). Starting 3 hours after the last gavage (t=75 hr, 72 hour treatment or t=25, 24 hour treatment), mice were euthanized by $CO_2$ asphyxiation and samples were collected within a 6 hour period and snap frozen in a liquid nitrogen bath and stored at −80° C. prior to analysis. All mice were handled in accordance with guidelines for the humane care and use of experimental animals, and the procedures used were approved by the University of California, San Diego Institutional Animal Care and Use Committee and the Salk Institute for Biological Studies Institutional Animal Care and Use Committee. Ileum and liver samples were used for qPCR.

RT-qPCR Analysis of Downstream FXR Gene Expression. Mouse liver and ileum segments were directly homogenized in TRIzol and total RNA isolated. cDNA was synthesized from 1 µg of DNase-treated total RNA using Bio-Rad iScript Reverse Transcription supermix (#1708841) and mRNA levels of Fgf15, Shp, Cyp7b1 and Cyp7a1 were quantified by quantitative PCR with Advanced Universal SyBr Green Supermix (Bio-Rad, cat #725271). All samples were run in technical triplicates and relative mRNA levels were calculated by using the standard curve methodology and normalized to 36B4.

REFERENCES: BACKGROUND AND EXAMPLES

1. Ridlon, J. M., Kang, D. J., Hylemon, P. B. & Bajaj, J. S. Bile acids and the gut microbiome. *Curr. Opin. Gastroenterol.* 30, 332-8 (2014).
2. Gilbert, J. A. et al. Microbiome-wide association studies link dynamic microbial consortia to disease. *Nature* 535, (2016).
3. Wikoff, W. R. et al. Metabolomics analysis reveals large effects of gut microflora on mammalian blood metabolites. *Proc. Natl. Acad. Sci. U.S.A.* 106, 3698-703 (2009).
4. Marcobal, A. et al. Metabolome progression during early gut microbial colonization of gnotobiotic mice. *Sci. Rep.* 5, 11589 (2015).
5. Miller, T. L. & Wolin, M. J. Pathways of acetate, propionate, and butyrate formation by the human fecal microbial flora. *Appl. Environ. Microbiol.* 62, 1589-92 (1996).
6. Gillner, M., Bergman, J., Cambillau, C., Fernstrom, B. & Gustafsson, J. A. Interactions of indoles with specific binding sites for 2,3,7,8-tetrachlorodibenzo-p-dioxin in rat liver. *Mol. Pharmacol.* 28, 357-63 (1985).
7. Martin, F.-P. J. et al. A top-down systems biology view of microbiome-mammalian metabolic interactions in a mouse model. *Mol. Syst. Biol.* 3, 112 (2007).
8. Moriya, T., Satomi, Y., Murata, S., Sawada, H. & Kobayashi, H. Effect of gut microbiota on host whole metabolome. *Metabolomics* 13, 101 (2017).
9. Swann, J. R. et al. Systemic gut microbial modulation of bile acid metabolism in host tissue compartments. *Proc. Natl. Acad. Sci. U.S.A.* 108 Suppl 1, 4523-30 (2011).
10. Structure, function and diversity of the healthy human microbiome. *Nature* 486, 207-14 (2012).
11. Wang, M. et al. Sharing and community curation of mass spectrometry data with Global Natural Products Social Molecular Networking. *Nat. Biotechnol.* 34, 828-837 (2016).
12. Watrous, J. et al. Mass spectral molecular networking of living microbial colonies. *Proc. Natl. Acad. Sci. U.S.A.* 109, 1743-52 (2012).
13. Protsyuk, I. et al. 3D molecular cartography using LC-MS facilitated by Optimus and 'ili software. *Nat. Protoc.* 13, 134-154 (2017).
14. Hofmann, A. F. & Hagey, L. R. Key discoveries in bile acid chemistry and biology and their clinical applications: history of the last eight decades. *J. Lipid Res.* 55, 1553-95 (2014).
15. Yang, J. Y. et al. Molecular networking as a dereplication strategy. *J Nat Prod* 76, 1686-1699 (2013).
16. Sumner, L. W. et al. Proposed minimum reporting standards for chemical analysis Chemical Analysis Working Group (CAWG) Metabolomics Standards Initiative (MSI). *Metabolomics* 3, 211-221 (2007).
17. Hartmann, A. C. et al. Meta-mass shift chemical profiling of metabolomes from coral reefs. *Proc. Natl. Acad. Sci. U.S.A.* 114, (2017).
18. Hirano, S. & Masuda, N. Characterization of NADP-dependent 7 beta-hydroxysteroid dehydrogenases from 18. Peptostreptococcus productus and Eubacterium aerofaciens. *Appl. Environ. Microbiol.* 43, 1057-63 (1982).
19. Wahlström, A., Sayin, S. I., Marschall, H.-U. & Backhed, F. Intestinal Crosstalk between Bile Acids and Microbiota and Its Impact on Host Metabolism. *Cell Metab.* 24, 41-50 (2016).
20. Huijghebaert, S. M. & Hofmann, A. F. Influence of the amino acid moiety on deconjugation of bile acid amidates by cholylglycine hydrolase or human fecal cultures. *J. Lipid Res.* 27, 742-52 (1986).
21. Myher, J. J., Marai, L., Kuksis, A., Yousef, I. M. & Fisher, M. M. Identification of ornithine and arginine conjugates of cholic acid by mass spectrometry. *Can. J. Biochem.* 53, 583-90 (1975).
22. PERIC-GOLIA, L. & JONES, R. S. Ornithocholanic acids and cholelithiasis in man. *Science* 142, 245-6 (1963).
23. Gordon, B. A., Kuksis, A. & Beveridge, J. M. R. Separation of bile acid conjugates by ion exchange chromatorgraphy. Can. J. Biochem. Physiol. 41, 77-89 (1963).
24. Yousef, I. M. & Fisher, M. M. Bile acid metabolism in mammals VIII. Biliary secretion of cholylarginine by the isolated perfused rat liver. *Can. J. Physiol. Pharmacol.* 53, 880-7 (1975).
25. Tamari, M., Ogawa, M. & Kametaka, M. A new bile acid conjugate, ciliatocholic acid, from bovine gall bladder bile. *J. Biochem.* 80, 371-7 (1976).
26. Hagey, L. R., Schteingart, C. D., Rossi, S. S., Ton-Nu, H. T. & Hofmann, A. F. An N-acyl glycyltaurine conjugate of deoxycholic acid in the biliary bile acids of the rabbit. *J. Lipid Res.* 39, 2119-24 (1998).
27. Nair, P. P., Solomon, R., Bankoski, J. & Plapinger, R. Bile acids in tissues: binding of lithocholic acid to protein. *Lipids* 13, 966-78 (1978).
28. McDonald, D. et al. American Gut: an Open Platform for Citizen Science Microbiome Research. *mSystems* 3, e00031-18 (2018).
29. Shalapour, S. et al. Inflammation-induced IgA+ cells dismantle anti-liver cancer immunity. *Nature* 551, 340-345 (2017).
30. Manor, 0. et al. Metagenomic evidence for taxonomic dysbiosis and functional imbalance in the gastrointestinal tracts of children with cystic fibrosis. *Sci. Rep.* 6, 22493 (2016).
31. Lloyd-Price, J. et al. Multi-omics of the gut microbial ecosystem in inflammatory bowel diseases. *Nature* 569, 655-662 (2019).
32. Hirano, S., Masuda, N., Oda, H. & Mukai, H. Transformation of bile acids by Clostridium perfringens. *Appl. Environ. Microbiol.* 42, 394-9 (1981).
33. Winston, J. A. & Theriot, C. M. Impact of microbial derived secondary bile acids on colonization resistance against Clostridium difficile in the gastrointestinal tract. *Anaerobe* 41, 44-50 (2016).
34. McDonald, J. A. K. et al. Evaluation of microbial community reproducibility, stability and composition in a human distal gut chemostat model. *J. Microbiol. Methods* 95, 167-174 (2013).
35. Finegold, S. M. et al. Pyrosequencing study of fecal microflora of autistic and control children. *Anaerobe* 16, 444-453 (2010).
36. Dehoux, P. et al. Comparative genomics of Clostridium bolteae and Clostridium clostridioforme reveals species-specific genomic properties and numerous putative antibiotic resistance determinants. *BMC Genomics* 17, 819 (2016).
37. Caballero, S. et al. Cooperating Commensals Restore Colonization Resistance to Vancomycin-Resistant Enterococcus faecium. *Cell Host Microbe* 21, 592-602.e4 (2017).
38. Sayin, S. I. et al. Gut Microbiota Regulates Bile Acid Metabolism by Reducing the Levels of Tauro-beta-muricholic Acid, a Naturally Occurring FXR Antagonist. *Cell Metab.* 17, 225-235 (2013).
39. Downes, M. et al. A Chemical, Genetic, and Structural Analysis of the Nuclear Bile Acid Receptor FXR. *Mol. Cell* 11, 1079-1092 (2003).
40. Gustafsson, B. E., Gustafsson, J. A. & Sjövall, J. Intestinal and fecal sterols in germfree and conventional rats. Bile acids and steroids 172. *Acta Chem. Scand.* 20, 1827-35 (1966).
41. Midtvedt, T. Microbial bile acid transformation. *Am. J. Clin. Nutr.* 27, 1341-1347 (1974).
42. Gérard, P. & Philippe. Metabolism of Cholesterol and Bile Acids by the Gut Microbiota. *Pathogens* 3, 14-24 (2013).

REFERENCES: METHODS

1. Tripathi, A. et al. Intermittent Hypoxia and Hypercapnia, a Hallmark of Obstructive Sleep Apnea, Alters the Gut Microbiome and Metabolome. *mSystems* 3, e00020-18 (2018).
2. McDonald, D. et al. American Gut: an Open Platform for Citizen Science Microbiome Research. *mSystems* 3, e00031-18 (2018).
3. Cullen, T. W. et al. Antimicrobial peptide resistance mediates resilience of prominent gut commensals during inflammation. *Science* (80-.). 347, 170-175 (2015).
4. Integrative HMP (iHMP) Research Network Consortium, T. I. H. (iHMP) R. N. The Integrative Human Microbiome Project: dynamic analysis of microbiome-host omics profiles during periods of human health and disease. *Cell Host Microbe* 16, 276-89 (2014).
5. Amorim, P., Moraes, T., Silva, J. & Pedrini, H. InVesalius: An Interactive Rendering Framework for Health Care Support. in 45-54 (Springer, Cham, 2015). doi: 10.1007/978-3-319-27857-5_5
6. Casteleyn, C., Rekecki, A., Van der Aa, A., Simoens, P. & Van den Broeck, W. Surface area assessment of the murine intestinal tract as a prerequisite for oral dose translation from mouse to man. *Lab. Anim.* 44, 176-83 (2010).
7. Shalapour, S. et al. Inflammation-induced IgA+ cells dismantle anti-liver cancer immunity. *Nature* 551, 340-345 (2017).
8. Caporaso, J. G. et al. QIIME allows analysis of high-throughput community sequencing data. *Nat. Methods* 7, 335-6 (2010).
9. Caporaso, J. G. et al. Ultra-high-throughput microbial community analysis on the Illumina HiSeq and MiSeq platforms. *ISME J.* 6, 1621-4 (2012).
10. Lloyd-Price, J. et al. Multi-omics of the gut microbial ecosystem in inflammatory bowel diseases. *Nature* 569, 655-662 (2019).
11. Protsyuk, I. et al. 3D molecular cartography using LC-MS facilitated by Optimus and 'ili software. *Nat. Protoc.* 13, 134-154 (2017).
12. Kenar, E. et al. Automated Label-free Quantification of Metabolites from Liquid Chromatography—Mass Spectrometry Data. *Mol. Cell. Proteomics* 13, 348-359 (2014).

13. Pluskal, T., Castillo, S., Villar-Briones, A. & Orešič, M. MZmine 2: Modular framework for processing, visualizing, and analyzing mass spectrometry-based molecular profile data. *BMC Bioinformatics* 11, 395 (2010).
14. Sumner, L. W. et al. Proposed minimum reporting standards for chemical analysis Chemical Analysis Working Group (CAWG) Metabolomics Standards Initiative (MSI). *Metabolomics* 3, 211-221 (2007).
15. Scheubert, K. et al. Significance estimation for large scale metabolomics annotations by spectral matching. *Nat. Commun.* 8, 1494 (2017).
16. Hartmann, A. C. et al. Meta-mass shift chemical profiling of metabolomes from coral reefs. *Proc. Natl. Acad. Sci. U.S.A.* 114, (2017).
17. Caporaso, J. G. et al. Global patterns of 16S rRNA diversity at a depth of millions of sequences per sample. *Proc. Natl. Acad. Sci. U.S.A.* 108 Suppl, 4516-22 (2011).
18. Amir, A. et al. Deblur Rapidly Resolves Single-Nucleotide Community Sequence Patterns. *mSystems* 2, (2017).
19. Lozupone, C. & Knight, R. UniFrac: a New Phylogenetic Method for Comparing Microbial Communities UniFrac: a New Phylogenetic Method for Comparing Microbial Communities. *Appl. Environ. Microbiol.* 71, 8228-8235 (2005).
20. DeSantis, T. Z. et al. Greengenes, a chimera-checked 16S rRNA gene database and workbench compatible with ARB. *Appl. Environ. Microbiol.* 72, 5069-72 (2006).
21. Mirarab, S., Nguyen, N. & Warnow, T. SEPP: SATe-enabled phylogenetic placement. *Pac. Symp. Biocomput.* 247-58 (2012).
22. Lozupone, C. & Knight, R. UniFrac: a new phylogenetic method for comparing microbial communities. *Appl. Environ. Microbiol.* 71, 8228-35 (2005).
23. Ezawa, T., Jung, S., Kawashima, Y., Noguchi, T. & Imai, N. Ecological Base-Conditioned Preparation of Dipeptides Using Unprotected α-Amino Acids Containing Hydrophilic Side Chains. *Bull. Chem. Soc. Jpn.* 90, 689-696 (2017).
24. Wang, M. et al. Sharing and community curation of mass spectrometry data with Global Natural Products Social Molecular Networking. *Nat. Biotechnol.* 34, (2016).
25. Morton, J. T. et al. Learning representations of microbe-metabolite interactions. *Nat. Methods* 1-9 (2019). doi:10.1038/s41592-019-0616-3
26. McDonald, J. A. K. et al. Evaluation of microbial community reproducibility, stability and composition in a human distal gut chemostat model. *J. Microbiol. Methods* 95, 167-174 (2013).

What is claimed is:

1. A method of treating a subject having inflammatory bowel disease (IBD), Crohn's disease (CD), ulcerative colitis (UC), cystic fibrosis (CF), liver cancer, colorectal cancer, diabetes, non-alcoholic fatty liver disease or atherosclerosis in need comprising administering to the subject an effective amount of a pharmaceutical composition comprising one or more microbially conjugated bile acids that modulate levels of a bile acid conjugate in the subject wherein the one or more microbially conjugated bile acids are conjugated with amino acids other than glycine or taurine.

2. The method of claim 1, wherein the one or more microbially conjugated bile acids are selected from phenylalanocholic acid, tyrosocholic acid and leucocholic acid.

3. The method of claim 1, wherein the composition comprises Clostridia microbes that increase levels of the bile acid conjugate in vivo.

4. The method of claim 1, wherein the composition stimulates farnesoid X receptor (FXR) in the subject.

5. A method of regulating bile acid levels in a subject in need comprising administering to the subject an effective amount of a pharmaceutical composition comprising one or more microbially conjugated bile acids that modulate levels of a bile acid conjugate in the subject wherein the one or more microbially conjugated bile acids are conjugated with amino acids other than glycine or taurine.

6. The method of claim 5, wherein the one or more microbially conjugated bile acids are selected from phenylalanocholic acid, tyrosocholic acid and leucocholic acid.

7. The method of claim 5, wherein the composition comprises Clostridia microbes that increase levels of the bile acid conjugate in vivo.

8. The method of claim 5, wherein the subject has inflammatory bowel disease (IBD), Crohn's disease (CD), ulcerative colitis (UC), cystic fibrosis (CF), liver cancer, colorectal cancer, diabetes, non-alcoholic fatty liver disease or atherosclerosis.

9. The method of claim 5, wherein the composition stimulates farnesoid X receptor (FXR) in the subject.

10. A method of regulating acylcarnitine levels in a subject in need comprising administering to the subject an effective amount of a pharmaceutical composition comprising one or more microbially conjugated bile acids that modulate levels of a bile acid conjugate in the subject wherein the one or more microbially conjugated bile acids are conjugated with amino acids other than glycine or taurine.

11. The method of claim 10, wherein the one or more microbially conjugated bile acids are selected from phenylalanocholic acid, tyrosocholic acid and leucocholic acid.

12. The method of claim 10, wherein the composition comprises Clostridia microbes that increase levels of the bile acid conjugate in vivo.

13. The method of claim 10, wherein the subject has inflammatory bowel disease (IBD), Crohn's disease (CD), ulcerative colitis (UC), cystic fibrosis (CF), liver cancer, colorectal cancer, diabetes, non-alcoholic fatty liver disease or atherosclerosis.

14. The method of claim 10, wherein the composition stimulates farnesoid X receptor (FXR) in the subject.

* * * * *